(12) United States Patent
Kamath et al.

(10) Patent No.: US 8,160,671 B2
(45) Date of Patent: *Apr. 17, 2012

(54) CALIBRATION TECHNIQUES FOR A CONTINUOUS ANALYTE SENSOR

(75) Inventors: Apurv Ullas Kamath, San Diego, CA (US); Peter C. Simpson, Encinitas, CA (US); James H. Brauker, Addison, MI (US); Paul V. Goode, Jr., Cherry Hill, NJ (US)

(73) Assignee: DexCom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/874,031

(22) Filed: Sep. 1, 2010

(65) Prior Publication Data

US 2010/0331655 A1 Dec. 30, 2010

Related U.S. Application Data

(63) Continuation of application No. 12/619,502, filed on Nov. 16, 2009, now Pat. No. 7,917,186, which is a continuation of application No. 11/004,561, filed on Dec. 3, 2004, now Pat. No. 7,715,893.

(60) Provisional application No. 60/527,323, filed on Dec. 5, 2003, provisional application No. 60/587,787, filed on Jul. 13, 2004, provisional application No. 60/614,683, filed on Sep. 30, 2004.

(51) Int. Cl.
*A61B 5/05* (2006.01)

(52) U.S. Cl. .......... 600/347; 600/345; 600/365

(58) Field of Classification Search .......... 600/345–347, 600/365; 435/7.4, 14; 422/50, 52, 400–404, 422/412, 420–430, 68.1, 69, 70, 82.01–82.13, 422/83

See application file for complete search history.

(56) References Cited

U.S. PATENT DOCUMENTS

| | | |
|---|---|---|
| 1,564,641 A | 12/1925 | St. James |
| 2,402,306 A | 6/1946 | Turkel |
| 2,719,797 A | 10/1955 | Rosenblatt et al. |
| 3,210,578 A | 10/1965 | Sherer |
| 3,219,533 A | 11/1965 | Mullins |
| 3,381,371 A | 5/1968 | Russell |
| 3,539,455 A | 11/1970 | Clark |
| 3,652,475 A | 3/1972 | Wada et al. |
| 3,775,182 A | 11/1973 | Patton et al. |
| 3,780,727 A | 12/1973 | Kind |

(Continued)

FOREIGN PATENT DOCUMENTS

DE 26 58 734 6/1978

(Continued)

OTHER PUBLICATIONS

Assolant-Vinet et al. 1986. New Immoblized Enzyme Membranes for Tailor-Made Biosensors, Anal Letters 19(7&8): 875-885.

(Continued)

*Primary Examiner* — Patricia Mallari
*Assistant Examiner* — Michael D'Angelo
(74) *Attorney, Agent, or Firm* — Knobbe Martens Olson & Bear LLP

(57) ABSTRACT

Disclosed herein are systems and methods for calibrating a continuous analyte sensor, such as a continuous glucose sensor. One such system utilizes one or more electrodes to measure an additional analyte. Such measurements may provide a baseline or sensitivity measurement for use in calibrating the sensor. Furthermore, baseline and/or sensitivity measurements may be used to trigger events such as digital filtering of data or suspending display of data.

16 Claims, 6 Drawing Sheets

U.S. PATENT DOCUMENTS

| | | |
|---|---|---|
| 3,791,871 A | 2/1974 | Rowley |
| 3,826,244 A | 7/1974 | Salcman et al. |
| 3,838,033 A | 9/1974 | Mindt et al. |
| 3,898,984 A | 8/1975 | Mandel et al. |
| 3,929,971 A | 12/1975 | Roy |
| 3,933,593 A | 1/1976 | Sternberg |
| 3,943,918 A | 3/1976 | Lewis |
| 3,957,613 A | 5/1976 | Macur |
| 3,979,274 A | 9/1976 | Newman |
| 3,982,530 A | 9/1976 | Storch |
| 4,037,563 A | 7/1977 | Pflueger et al. |
| 4,052,754 A | 10/1977 | Homsy |
| 4,067,322 A | 1/1978 | Johnson |
| 4,076,656 A | 2/1978 | White et al. |
| 4,197,840 A | 4/1980 | Beck et al. |
| 4,240,889 A | 12/1980 | Yoda et al. |
| 4,253,469 A | 3/1981 | Aslan |
| 4,255,500 A | 3/1981 | Hooke |
| 4,319,578 A | 3/1982 | Enger |
| 4,324,257 A | 4/1982 | Albarda et al. |
| 4,353,368 A | 10/1982 | Slovak et al. |
| 4,374,013 A | 2/1983 | Enfors |
| 4,378,016 A | 3/1983 | Loeb |
| 4,402,694 A | 9/1983 | Ash et al. |
| 4,403,847 A | 9/1983 | Chrestensen |
| 4,403,984 A | 9/1983 | Ash et al. |
| 4,415,666 A | 11/1983 | D'Orazio et al. |
| 4,418,148 A | 11/1983 | Oberhardt |
| 4,419,535 A | 12/1983 | O'Hara |
| 4,431,004 A | 2/1984 | Bessman et al. |
| 4,431,507 A | 2/1984 | Nankai et al. |
| 4,436,094 A | 3/1984 | Cerami |
| 4,442,841 A | 4/1984 | Uehara et al. |
| 4,454,295 A | 6/1984 | Wittmann et al. |
| 4,477,314 A | 10/1984 | Richter et al. |
| 4,494,950 A | 1/1985 | Fischell |
| 4,506,680 A | 3/1985 | Stokes |
| RE31,916 E | 6/1985 | Oswin et al. |
| 4,554,927 A | 11/1985 | Fussell |
| 4,561,963 A | 12/1985 | Owen et al. |
| 4,571,292 A | 2/1986 | Liu et al. |
| 4,577,642 A | 3/1986 | Stokes |
| 4,579,120 A | 4/1986 | MacGregor |
| 4,583,976 A | 4/1986 | Ferguson |
| 4,603,152 A | 7/1986 | Laurin et al. |
| RE32,361 E | 2/1987 | Duggan |
| 4,650,547 A | 3/1987 | Gough |
| 4,655,880 A | 4/1987 | Liu |
| 4,671,288 A | 6/1987 | Gough |
| 4,672,970 A | 6/1987 | Uchida et al. |
| 4,675,346 A | 6/1987 | Lin et al. |
| 4,680,268 A | 7/1987 | Clark, Jr. |
| 4,703,756 A | 11/1987 | Gough et al. |
| 4,721,677 A | 1/1988 | Clark |
| 4,731,726 A | 3/1988 | Allen |
| 4,750,496 A | 6/1988 | Reinhart et al. |
| 4,752,935 A | 6/1988 | Beck |
| 4,757,022 A | 7/1988 | Shults et al. |
| 4,759,828 A | 7/1988 | Young et al. |
| 4,776,944 A | 10/1988 | Janata et al. |
| 4,781,798 A | 11/1988 | Gough |
| 4,787,398 A | 11/1988 | Garcia et al. |
| 4,795,435 A | 1/1989 | Steer |
| 4,795,542 A | 1/1989 | Ross et al. |
| 4,805,624 A | 2/1989 | Yao et al. |
| 4,805,625 A | 2/1989 | Wyler |
| 4,810,470 A | 3/1989 | Burkhardt et al. |
| 4,813,424 A | 3/1989 | Wilkins |
| 4,831,070 A | 5/1989 | McInally et al. |
| 4,849,458 A | 7/1989 | Reed et al. |
| 4,852,573 A | 8/1989 | Kennedy |
| 4,858,615 A | 8/1989 | Meinema |
| 4,861,454 A | 8/1989 | Ushizawa et al. |
| 4,871,440 A | 10/1989 | Nagata et al. |
| 4,883,057 A | 11/1989 | Broderick |
| 4,890,620 A | 1/1990 | Gough |
| 4,890,621 A | 1/1990 | Hakky |
| 4,919,141 A | 4/1990 | Zier et al. |
| 4,927,407 A | 5/1990 | Dorman |
| 4,927,516 A | 5/1990 | Yamaguchi et al. |
| 4,944,299 A | 7/1990 | Silvian |
| 4,953,552 A | 9/1990 | DeMarzo |
| 4,955,861 A | 9/1990 | Enegren et al. |
| 4,958,148 A | 9/1990 | Olson |
| 4,974,929 A | 12/1990 | Curry |
| 4,975,175 A | 12/1990 | Karube et al. |
| 4,975,636 A | 12/1990 | Desautels |
| 4,986,671 A | 1/1991 | Sun et al. |
| 4,988,341 A | 1/1991 | Columbus et al. |
| 4,988,758 A | 1/1991 | Fukuda et al. |
| 4,992,794 A | 2/1991 | Brouwers |
| 4,994,167 A | 2/1991 | Shults et al. |
| 5,002,572 A | 3/1991 | Picha |
| 5,019,096 A | 5/1991 | Fox, Jr. et al. |
| 5,030,333 A | 7/1991 | Clark, Jr. |
| 5,034,112 A | 7/1991 | Murase et al. |
| 5,050,612 A | 9/1991 | Matsumura |
| 5,068,536 A | 11/1991 | Rosenthal |
| 5,077,476 A | 12/1991 | Rosenthal |
| 5,089,112 A | 2/1992 | Skotheim et al. |
| 5,097,834 A | 3/1992 | Skrabal |
| 5,101,814 A | 4/1992 | Palti |
| 5,108,819 A | 4/1992 | Heller et al. |
| 5,137,028 A | 8/1992 | Nishimura |
| 5,140,985 A | 8/1992 | Schroeder et al. |
| 5,160,418 A | 11/1992 | Mullen |
| 5,165,407 A | 11/1992 | Wilson et al. |
| 5,171,689 A | 12/1992 | Kawaguri et al. |
| 5,190,041 A | 3/1993 | Palti |
| 5,198,771 A | 3/1993 | Fidler et al. |
| 5,202,261 A | 4/1993 | Musho et al. |
| 5,208,147 A | 5/1993 | Kagenow et al. |
| 5,243,696 A | 9/1993 | Carr et al. |
| 5,243,983 A | 9/1993 | Tarr et al. |
| 5,249,576 A | 10/1993 | Goldberger et al. |
| 5,262,305 A | 11/1993 | Heller et al. |
| 5,264,103 A | 11/1993 | Yoshioka et al. |
| 5,264,104 A | 11/1993 | Gregg et al. |
| 5,266,179 A | 11/1993 | Nankai et al. |
| 5,269,891 A | 12/1993 | Colin |
| 5,281,319 A | 1/1994 | Kaneko et al. |
| 5,282,848 A | 2/1994 | Schmitt |
| 5,284,140 A | 2/1994 | Allen et al. |
| 5,287,753 A | 2/1994 | Routh et al. |
| 5,298,144 A | 3/1994 | Spokane |
| 5,299,571 A | 4/1994 | Mastrototaro |
| 5,307,263 A | 4/1994 | Brown |
| 5,310,469 A | 5/1994 | Cunningham et al. |
| 5,312,361 A | 5/1994 | Zadini et al. |
| 5,316,008 A | 5/1994 | Suga et al. |
| 5,322,063 A | 6/1994 | Allen et al. |
| 5,324,322 A | 6/1994 | Grill, Jr. et al. |
| 5,328,451 A | 7/1994 | Davis et al. |
| 5,330,634 A | 7/1994 | Wong et al. |
| 5,331,555 A | 7/1994 | Hashimoto et al. |
| 5,337,747 A | 8/1994 | Neftel |
| 5,352,351 A | 10/1994 | White |
| 5,354,449 A | 10/1994 | Band et al. |
| 5,356,786 A | 10/1994 | Heller et al. |
| 5,368,224 A | 11/1994 | Richardson et al. |
| 5,372,133 A | 12/1994 | Hogen Esch |
| 5,376,070 A | 12/1994 | Purvis et al. |
| 5,384,028 A | 1/1995 | Ito |
| 5,387,327 A | 2/1995 | Khan |
| 5,390,671 A | 2/1995 | Lord et al. |
| 5,391,250 A | 2/1995 | Cheney, II et al. |
| 5,411,647 A | 5/1995 | Johnson et al. |
| 5,411,866 A | 5/1995 | Luong |
| 5,425,717 A | 6/1995 | Mohiuddin |
| 5,429,735 A | 7/1995 | Johnson et al. |
| 5,431,160 A | 7/1995 | Wilkins |
| 5,434,412 A | 7/1995 | Sodickson et al. |
| 5,448,992 A | 9/1995 | Kuperschmidt |
| 5,462,051 A | 10/1995 | Oka et al. |
| 5,462,064 A | 10/1995 | D'Angelo et al. |
| 5,462,645 A | 10/1995 | Albery et al. |
| 5,466,356 A | 11/1995 | Schneider et al. |

| | | | | | | |
|---|---|---|---|---|---|---|
| 5,474,552 A | 12/1995 | Palti | | 5,882,494 A | 3/1999 | Van Antwerp |
| 5,476,776 A | 12/1995 | Wilkins | | 5,895,235 A | 4/1999 | Droz |
| 5,482,008 A | 1/1996 | Stafford et al. | | 5,897,578 A | 4/1999 | Wiklund et al. |
| 5,482,473 A | 1/1996 | Lord et al. | | 5,899,855 A | 5/1999 | Brown |
| 5,486,776 A | 1/1996 | Chiang | | 5,904,708 A | 5/1999 | Goedeke |
| 5,494,562 A | 2/1996 | Maley et al. | | 5,913,998 A | 6/1999 | Butler et al. |
| 5,496,453 A | 3/1996 | Uenoyama et al. | | 5,914,026 A | 6/1999 | Blubaugh, Jr. et al. |
| 5,497,772 A * | 3/1996 | Schulman et al. ............ 600/347 | | 5,919,215 A | 7/1999 | Wiklund et al. |
| 5,502,396 A | 3/1996 | Desarzens et al. | | 5,928,130 A | 7/1999 | Schmidt |
| 5,507,288 A | 4/1996 | Bocker et al. | | 5,931,814 A | 8/1999 | Alex et al. |
| 5,508,509 A | 4/1996 | Yafuso et al. | | 5,932,175 A | 8/1999 | Knute et al. |
| 5,513,636 A | 5/1996 | Palti | | 5,933,136 A | 8/1999 | Brown |
| 5,518,601 A | 5/1996 | Foos et al. | | 5,944,661 A | 8/1999 | Swette et al. |
| 5,529,676 A | 6/1996 | Maley et al. | | 5,954,643 A | 9/1999 | Van Antwerp et al. |
| 5,531,878 A | 7/1996 | Vadgama et al. | | 5,954,954 A | 9/1999 | Houck et al. |
| 5,540,828 A | 7/1996 | Yacynych | | 5,957,854 A | 9/1999 | Besson et al. |
| 5,553,616 A | 9/1996 | Ham et al. | | 5,961,451 A | 10/1999 | Reber et al. |
| 5,564,439 A | 10/1996 | Picha | | 5,963,132 A | 10/1999 | Yoakum |
| 5,568,806 A | 10/1996 | Cheney, II et al. | | 5,964,993 A | 10/1999 | Blubaugh et al. |
| 5,569,186 A | 10/1996 | Lord et al. | | 5,965,125 A | 10/1999 | Mineau-Hanschke |
| 5,569,462 A | 10/1996 | Martinson et al. | | 5,965,380 A | 10/1999 | Heller et al. |
| 5,571,395 A | 11/1996 | Park et al. | | 5,971,922 A | 10/1999 | Arita et al. |
| 5,575,293 A | 11/1996 | Miller et al. | | 5,972,199 A | 10/1999 | Heller et al. |
| 5,575,930 A | 11/1996 | Tietje-Girault et al. | | 5,976,085 A | 11/1999 | Kimball et al. |
| 5,582,184 A | 12/1996 | Ericson et al. | | 5,985,129 A | 11/1999 | Gough et al. |
| 5,582,497 A | 12/1996 | Noguchi | | 5,989,409 A | 11/1999 | Kurnik et al. |
| 5,582,697 A | 12/1996 | Ikeda et al. | | 5,995,860 A | 11/1999 | Sun et al. |
| 5,584,813 A | 12/1996 | Livingston et al. | | 5,999,848 A | 12/1999 | Gord et al. |
| 5,586,553 A | 12/1996 | Halili et al. | | 6,001,067 A | 12/1999 | Shults et al. |
| 5,588,560 A | 12/1996 | Benedict et al. | | 6,011,984 A | 1/2000 | Van Antwerp et al. |
| 5,589,133 A | 12/1996 | Suzuki | | 6,013,113 A | 1/2000 | Mika |
| 5,593,852 A | 1/1997 | Heller et al. | | 6,016,448 A | 1/2000 | Busacker et al. |
| 5,605,152 A | 2/1997 | Slate et al. | | 6,027,445 A | 2/2000 | Von Bahr |
| 5,607,565 A | 3/1997 | Azarnia et al. | | 6,036,924 A | 3/2000 | Simons et al. |
| 5,611,900 A | 3/1997 | Worden | | 6,049,727 A | 4/2000 | Crothall |
| 5,624,537 A | 4/1997 | Turner et al. | | 6,051,389 A | 4/2000 | Ahl et al. |
| 5,628,890 A | 5/1997 | Carter et al. | | 6,059,946 A | 5/2000 | Yukawa et al. |
| 5,640,954 A | 6/1997 | Pfeiffer | | 6,065,154 A | 5/2000 | Hulings et al. |
| 5,653,863 A | 8/1997 | Genshaw et al. | | 6,066,083 A | 5/2000 | Slater et al. |
| 5,660,163 A | 8/1997 | Schulman et al. | | 6,066,448 A | 5/2000 | Wohlstadter et al. |
| 5,676,820 A | 10/1997 | Wang et al. | | 6,074,775 A | 6/2000 | Gartstein et al. |
| 5,682,884 A | 11/1997 | Hill et al. | | 6,081,735 A | 6/2000 | Diab et al. |
| 5,683,562 A | 11/1997 | Schaffar et al. | | 6,081,736 A | 6/2000 | Colvin et al. |
| 5,686,829 A | 11/1997 | Girault | | 6,083,523 A | 7/2000 | Dionne et al. |
| 5,695,623 A | 12/1997 | Michel et al. | | 6,083,710 A | 7/2000 | Heller et al. |
| 5,696,314 A | 12/1997 | McCaffrey et al. | | 6,088,608 A | 7/2000 | Schulman et al. |
| 5,704,354 A | 1/1998 | Priedel et al. | | 6,091,975 A | 7/2000 | Daddona et al. |
| 5,706,807 A | 1/1998 | Picha | | 6,093,156 A | 7/2000 | Cunningham et al. |
| 5,707,502 A | 1/1998 | McCaffrey et al. | | 6,093,172 A | 7/2000 | Funderburk et al. |
| 5,711,861 A | 1/1998 | Ward et al. | | 6,107,083 A | 8/2000 | Collins et al. |
| 5,730,654 A | 3/1998 | Brown | | 6,117,290 A | 9/2000 | Say et al. |
| 5,735,273 A | 4/1998 | Kurnik et al. | | 6,119,028 A | 9/2000 | Schulman et al. |
| 5,741,330 A | 4/1998 | Brauker et al. | | 6,120,676 A | 9/2000 | Heller et al. |
| 5,741,634 A | 4/1998 | Nozoe et al. | | 6,121,009 A | 9/2000 | Heller et al. |
| 5,743,262 A | 4/1998 | Lepper, Jr. et al. | | 6,122,536 A | 9/2000 | Sun et al. |
| 5,749,832 A | 5/1998 | Vadgama et al. | | 6,123,827 A | 9/2000 | Wong et al. |
| 5,749,907 A | 5/1998 | Mann | | 6,134,461 A | 10/2000 | Say et al. |
| 5,766,151 A | 6/1998 | Valley et al. | | 6,135,978 A | 10/2000 | Houben et al. |
| 5,776,324 A | 7/1998 | Usala | | 6,144,869 A | 11/2000 | Berner et al. |
| 5,781,455 A | 7/1998 | Hyodo et al. | | 6,144,871 A | 11/2000 | Saito et al. |
| 5,791,344 A | 8/1998 | Schulman et al. | | 6,162,611 A | 12/2000 | Heller et al. |
| 5,795,774 A | 8/1998 | Matsumoto et al. | | 6,168,568 B1 | 1/2001 | Gavriely |
| 5,800,420 A | 9/1998 | Gross | | 6,169,155 B1 | 1/2001 | Alvarez et al. |
| 5,806,517 A | 9/1998 | Gerhardt et al. | | 6,175,752 B1 | 1/2001 | Say et al. |
| 5,807,375 A | 9/1998 | Gross et al. | | 6,175,753 B1 | 1/2001 | Menkes et al. |
| 5,814,599 A | 9/1998 | Mitragotri et al. | | 6,180,416 B1 | 1/2001 | Kurnik et al. |
| 5,820,622 A | 10/1998 | Gross et al. | | 6,201,980 B1 | 3/2001 | Darrow et al. |
| 5,822,715 A | 10/1998 | Worthington et al. | | 6,201,993 B1 | 3/2001 | Kruse et al. |
| 5,823,802 A | 10/1998 | Barley | | 6,208,894 B1 | 3/2001 | Schulman et al. |
| 5,833,603 A | 11/1998 | Kovacs et al. | | 6,212,416 B1 | 4/2001 | Ward et al. |
| 5,836,887 A | 11/1998 | Oka et al. | | 6,212,417 B1 | 4/2001 | Ikeda et al. |
| 5,836,989 A | 11/1998 | Shelton | | 6,212,424 B1 | 4/2001 | Robinson |
| 5,840,148 A | 11/1998 | Campbell et al. | | 6,214,185 B1 | 4/2001 | Offenbacher et al. |
| 5,851,197 A | 12/1998 | Marano et al. | | 6,219,574 B1 | 4/2001 | Cormier et al. |
| 5,861,019 A | 1/1999 | Sun et al. | | 6,223,083 B1 | 4/2001 | Rosar |
| 5,863,400 A | 1/1999 | Drummond et al. | | 6,230,059 B1 | 5/2001 | Duffin |
| 5,871,499 A | 2/1999 | Hahn et al. | | 6,233,080 B1 | 5/2001 | Brenner et al. |
| 5,871,514 A | 2/1999 | Wiklund et al. | | 6,233,471 B1 | 5/2001 | Berner et al. |
| 5,879,373 A | 3/1999 | Roper et al. | | 6,248,067 B1 | 6/2001 | Causey, III et al. |

| Patent No. | Date | Inventor |
|---|---|---|
| 6,256,522 B1 | 7/2001 | Schultz |
| 6,259,937 B1 | 7/2001 | Schulman et al. |
| 6,264,825 B1 | 7/2001 | Blackburn et al. |
| 6,268,161 B1 | 7/2001 | Han et al. |
| 6,272,364 B1 | 8/2001 | Kurnik |
| 6,272,480 B1 | 8/2001 | Tresp et al. |
| 6,274,285 B1 | 8/2001 | Gries et al. |
| 6,275,717 B1 | 8/2001 | Gross et al. |
| 6,284,478 B1 | 9/2001 | Heller et al. |
| 6,285,897 B1 | 9/2001 | Kilcoyne et al. |
| 6,293,925 B1 | 9/2001 | Safabash et al. |
| 6,294,281 B1 | 9/2001 | Heller |
| 6,299,578 B1 | 10/2001 | Kurnik et al. |
| 6,300,002 B1 | 10/2001 | Webb et al. |
| 6,302,855 B1 | 10/2001 | Lav et al. |
| 6,309,351 B1 | 10/2001 | Kurnik et al. |
| 6,309,526 B1 | 10/2001 | Fujiwara et al. |
| 6,309,884 B1 | 10/2001 | Cooper et al. |
| 6,325,979 B1 | 12/2001 | Hahn et al. |
| 6,326,160 B1 | 12/2001 | Dunn et al. |
| 6,329,161 B1 | 12/2001 | Heller et al. |
| 6,329,929 B1 | 12/2001 | Weijand et al. |
| 6,330,464 B1 | 12/2001 | Colvin, Jr. et al. |
| 6,343,225 B1 | 1/2002 | Clark, Jr. |
| 6,356,776 B1 | 3/2002 | Berner et al. |
| 6,360,888 B1 | 3/2002 | Melver et al. |
| 6,366,794 B1 | 4/2002 | Moussy et al. |
| 6,368,141 B1 | 4/2002 | Van Antwerp et al. |
| 6,368,274 B1 | 4/2002 | Van Antwerp et al. |
| 6,370,941 B2 | 4/2002 | Nakamura et al. |
| 6,379,301 B1 | 4/2002 | Worthington et al. |
| 6,406,066 B1 | 6/2002 | Uegane |
| 6,406,426 B1 | 6/2002 | Reuss et al. |
| 6,409,674 B1 | 6/2002 | Brockway et al. |
| 6,413,393 B1 | 7/2002 | Van Antwerp et al. |
| 6,413,396 B1 | 7/2002 | Yang et al. |
| 6,416,651 B1 | 7/2002 | Miller |
| 6,418,332 B1 | 7/2002 | Mastrototaro et al. |
| 6,424,847 B1 | 7/2002 | Mastrototaro et al. |
| 6,447,448 B1 | 9/2002 | Ishikawa et al. |
| 6,454,710 B1 | 9/2002 | Ballerstadt et al. |
| 6,459,917 B1 | 10/2002 | Gowda et al. |
| 6,461,496 B1 | 10/2002 | Feldman et al. |
| 6,465,066 B1 | 10/2002 | Rule et al. |
| 6,466,810 B1 | 10/2002 | Ward et al. |
| 6,471,689 B1 | 10/2002 | Joseph et al. |
| 6,475,372 B1 | 11/2002 | Ohara et al. |
| 6,475,750 B1 | 11/2002 | Han et al. |
| 6,477,392 B1 | 11/2002 | Honigs et al. |
| 6,477,395 B2 | 11/2002 | Schulman et al. |
| 6,484,045 B1 | 11/2002 | Holker et al. |
| 6,484,046 B1 | 11/2002 | Say et al. |
| 6,494,830 B1 | 12/2002 | Wessel |
| 6,498,043 B1 | 12/2002 | Schulman et al. |
| 6,498,941 B1 | 12/2002 | Jackson |
| 6,510,329 B2 | 1/2003 | Heckel |
| 6,512,939 B1 | 1/2003 | Colvin et al. |
| 6,514,718 B2 | 2/2003 | Heller et al. |
| 6,520,326 B2 | 2/2003 | McIvor et al. |
| 6,526,298 B1 | 2/2003 | Khalil et al. |
| 6,527,729 B1 | 3/2003 | Turcott |
| 6,534,711 B1 | 3/2003 | Pollack |
| 6,542,765 B1 | 4/2003 | Guy et al. |
| 6,544,212 B2 | 4/2003 | Galley et al. |
| 6,546,268 B1 | 4/2003 | Ishikawa et al. |
| 6,546,269 B1 | 4/2003 | Kurnik |
| 6,547,839 B2 | 4/2003 | Zhang et al. |
| 6,551,496 B1 | 4/2003 | Moles et al. |
| 6,553,241 B2 | 4/2003 | Mannheimer et al. |
| 6,553,244 B2 | 4/2003 | Lesho et al. |
| 6,558,320 B1 | 5/2003 | Causey et al. |
| 6,558,321 B1 | 5/2003 | Burd et al. |
| 6,558,351 B1 | 5/2003 | Steil et al. |
| 6,560,471 B1 | 5/2003 | Heller et al. |
| 6,561,978 B1 | 5/2003 | Conn et al. |
| 6,565,509 B1 | 5/2003 | Say et al. |
| 6,569,309 B2 | 5/2003 | Otsuka et al. |
| 6,572,545 B2 | 6/2003 | Knobbe et al. |
| 6,572,579 B1 | 6/2003 | Raghavan et al. |
| 6,574,490 B2 | 6/2003 | Abbink et al. |
| 6,575,905 B2 | 6/2003 | Knobbe et al. |
| 6,579,498 B1 | 6/2003 | Eglise |
| 6,579,690 B1 | 6/2003 | Bonnecaze et al. |
| 6,585,644 B2 | 7/2003 | Lebel et al. |
| 6,585,763 B1 | 7/2003 | Keilman et al. |
| 6,587,705 B1 | 7/2003 | Kim et al. |
| 6,589,229 B1 | 7/2003 | Connelly et al. |
| 6,591,125 B1 | 7/2003 | Buse et al. |
| 6,594,514 B2 | 7/2003 | Berner et al. |
| 6,595,919 B2 | 7/2003 | Berner et al. |
| 6,605,072 B2 | 8/2003 | Struys et al. |
| 6,607,658 B1 | 8/2003 | Heller et al. |
| 6,612,984 B1 | 9/2003 | Kerr, II |
| 6,613,379 B2 | 9/2003 | Ward et al. |
| 6,615,078 B1 | 9/2003 | Burson et al. |
| 6,618,934 B1 | 9/2003 | Feldman et al. |
| 6,633,772 B2 | 10/2003 | Ford et al. |
| 6,641,533 B2 | 11/2003 | Causey et al. |
| 6,642,015 B2 | 11/2003 | Vachon et al. |
| 6,653,091 B1 | 11/2003 | Dunn et al. |
| 6,654,625 B1 | 11/2003 | Say et al. |
| 6,673,022 B1 | 1/2004 | Bobo et al. |
| 6,673,596 B1 | 1/2004 | Sayler et al. |
| 6,689,265 B2 | 2/2004 | Heller et al. |
| 6,695,958 B1 | 2/2004 | Adam et al. |
| 6,699,188 B2 | 3/2004 | Wessel |
| 6,699,383 B2 | 3/2004 | Lemire et al. |
| 6,702,857 B2 | 3/2004 | Brauker et al. |
| 6,702,972 B1 | 3/2004 | Markle |
| 6,721,587 B2 | 4/2004 | Gough |
| 6,730,200 B1 | 5/2004 | Stewart et al. |
| 6,733,655 B1 | 5/2004 | Davies et al. |
| 6,737,158 B1 | 5/2004 | Thompson |
| 6,741,877 B1 | 5/2004 | Shults et al. |
| 6,743,635 B2 | 6/2004 | Neel et al. |
| 6,773,565 B2 | 8/2004 | Kunimoto et al. |
| 6,793,632 B2 | 9/2004 | Sohrab |
| 6,793,802 B2 | 9/2004 | Lee et al. |
| 6,801,041 B2 | 10/2004 | Karinka et al. |
| 6,802,957 B2 | 10/2004 | Jung et al. |
| 6,809,507 B2 | 10/2004 | Morgan et al. |
| 6,809,653 B1 | 10/2004 | Mann et al. |
| 6,862,465 B2 | 3/2005 | Shults et al. |
| 6,869,413 B2 | 3/2005 | Langley et al. |
| 6,892,085 B2 | 5/2005 | McIvor et al. |
| 6,893,552 B1 | 5/2005 | Wang et al. |
| 6,895,263 B2 | 5/2005 | Shin et al. |
| 6,925,393 B1 | 8/2005 | Kalatz et al. |
| 6,931,327 B2 | 8/2005 | Goode et al. |
| 6,932,894 B2 | 8/2005 | Mao et al. |
| 6,952,604 B2 | 10/2005 | DeNuzzio et al. |
| 6,965,791 B1 | 11/2005 | Hitchcock et al. |
| 6,972,080 B1 | 12/2005 | Tomioka et al. |
| 6,998,247 B2 | 2/2006 | Monfre et al. |
| 7,003,336 B2 | 2/2006 | Holker et al. |
| 7,003,341 B2 | 2/2006 | Say et al. |
| 7,011,630 B2 | 3/2006 | Desai et al. |
| 7,025,743 B2 | 4/2006 | Mann et al. |
| 7,029,444 B2 | 4/2006 | Shin et al. |
| 7,058,437 B2 | 6/2006 | Buse et al. |
| 7,060,059 B2 | 6/2006 | Keith et al. |
| 7,070,580 B2 | 7/2006 | Nielsen |
| 7,074,307 B2 | 7/2006 | Simpson et al. |
| 7,078,582 B2 | 7/2006 | Stebbings et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,115,884 B1 | 10/2006 | Walt et al. |
| 7,134,999 B2 | 11/2006 | Brauker et al. |
| 7,153,265 B2 | 12/2006 | Vachon |
| 7,166,074 B2 | 1/2007 | Reghabit et al. |
| 7,169,289 B2 | 1/2007 | Schulein et al. |
| 7,190,988 B2 | 3/2007 | Say et al. |
| 7,207,974 B2 | 4/2007 | Safabash et al. |
| 7,225,535 B2 | 6/2007 | Feldman et al. |
| 7,229,288 B2 | 6/2007 | Stuart et al. |
| 7,261,690 B2 | 8/2007 | Teller et al. |
| 7,267,665 B2 | 9/2007 | Steil et al. |

| | | | | | | |
|---|---|---|---|---|---|---|
| 7,276,029 B2 | 10/2007 | Goode et al. | | 2003/0036773 A1 | 2/2003 | Whitehurst et al. |
| 7,278,983 B2 | 10/2007 | Ireland et al. | | 2003/0050537 A1 | 3/2003 | Wessel |
| 7,295,867 B2 | 11/2007 | Berner et al. | | 2003/0050546 A1 | 3/2003 | Desai et al. |
| 7,310,544 B2 | 12/2007 | Brister et al. | | 2003/0060765 A1 | 3/2003 | Campbell et al. |
| 7,329,239 B2 | 2/2008 | Safabash et al. | | 2003/0065254 A1 | 4/2003 | Schulman et al. |
| 7,344,499 B1 | 3/2008 | Prausnitz et al. | | 2003/0070548 A1 | 4/2003 | Clausen |
| 7,354,420 B2 | 4/2008 | Steil et al. | | 2003/0076082 A1 | 4/2003 | Morgan et al. |
| 7,359,723 B2 | 4/2008 | Jones | | 2003/0078481 A1 | 4/2003 | McIvor et al. |
| 7,366,556 B2 | 4/2008 | Brister et al. | | 2003/0078560 A1 | 4/2003 | Miller et al. |
| 7,381,184 B2 | 6/2008 | Funderburk et al. | | 2003/0097082 A1 | 5/2003 | Purdy et al. |
| 7,399,277 B2 | 7/2008 | Saidara et al. | | 2003/0100040 A1 | 5/2003 | Bonnecaze et al. |
| 7,402,153 B2 | 7/2008 | Steil et al. | | 2003/0100821 A1 | 5/2003 | Heller et al. |
| 7,417,164 B2 | 8/2008 | Suri | | 2003/0114735 A1 | 6/2003 | Silver et al. |
| 7,424,318 B2 | 9/2008 | Brister et al. | | 2003/0117296 A1 | 6/2003 | Seely |
| 7,426,408 B2 | 9/2008 | DeNuzzio et al. | | 2003/0119208 A1 | 6/2003 | Yoon et al. |
| 7,460,898 B2 | 12/2008 | Brister et al. | | 2003/0125612 A1 | 7/2003 | Fox et al. |
| 7,467,003 B2 | 12/2008 | Brister et al. | | 2003/0125613 A1 | 7/2003 | Enegren et al. |
| 7,471,972 B2 | 12/2008 | Rhodes et al. | | 2003/0130616 A1 | 7/2003 | Steil et al. |
| 7,494,465 B2 | 2/2009 | Brister et al. | | 2003/0134347 A1 | 7/2003 | Heller et al. |
| 7,497,827 B2 | 3/2009 | Brister et al. | | 2003/0138674 A1 | 7/2003 | Zeikus et al. |
| 7,519,408 B2 | 4/2009 | Rasdal et al. | | 2003/0181794 A1 | 9/2003 | Rini et al. |
| 7,519,478 B2 | 4/2009 | Bartkowiak et al. | | 2003/0187338 A1 | 10/2003 | Say et al. |
| 7,523,004 B2 | 4/2009 | Bartkowiak et al. | | 2003/0188427 A1 | 10/2003 | Say et al. |
| 7,525,298 B2 | 4/2009 | Morgan et al. | | 2003/0199744 A1 | 10/2003 | Buse et al. |
| 7,583,990 B2 | 9/2009 | Goode, Jr. et al. | | 2003/0203498 A1 | 10/2003 | Neel et al. |
| 7,587,287 B2 | 9/2009 | Connolly et al. | | 2003/0208113 A1 | 11/2003 | Mault et al. |
| 7,591,801 B2 | 9/2009 | Brauker et al. | | 2003/0211625 A1 | 11/2003 | Cohan |
| 7,599,726 B2 | 10/2009 | Goode et al. | | 2003/0212317 A1 | 11/2003 | Kovatchev et al. |
| 7,618,368 B2 | 11/2009 | Brown | | 2003/0212346 A1 | 11/2003 | Yuzhakov et al. |
| 7,624,028 B1 | 11/2009 | Brown | | 2003/0212347 A1 | 11/2003 | Sohrab |
| 7,636,602 B2 | 12/2009 | Baru Fassio et al. | | 2003/0225437 A1 | 12/2003 | Ferguson |
| 7,637,868 B2 | 12/2009 | Saint et al. | | 2003/0228681 A1 | 12/2003 | Ritts et al. |
| 7,640,032 B2 | 12/2009 | Jones | | 2003/0235817 A1 | 12/2003 | Bartkowiak et al. |
| 7,640,048 B2 | 12/2009 | Dobbles et al. | | 2004/0011671 A1 | 1/2004 | Shults et al. |
| 7,654,956 B2 | 2/2010 | Brister et al. | | 2004/0015063 A1 | 1/2004 | DeNuzzio et al. |
| 7,657,297 B2 | 2/2010 | Simpson et al. | | 2004/0018486 A1 | 1/2004 | Dunn et al. |
| 7,711,402 B2 | 5/2010 | Shults et al. | | 2004/0023253 A1 | 2/2004 | Kunwar et al. |
| 7,771,352 B2 | 8/2010 | Shults et al. | | 2004/0023317 A1 | 2/2004 | Motamedi et al. |
| 7,774,145 B2 | 8/2010 | Brauker et al. | | 2004/0024327 A1 | 2/2004 | Brodnick |
| 7,792,562 B2 | 9/2010 | Shults et al. | | 2004/0039298 A1 | 2/2004 | Abreu |
| 7,831,287 B2 | 11/2010 | Brister et al. | | 2004/0045879 A1 | 3/2004 | Shults et al. |
| 7,896,809 B2 | 3/2011 | Simpson et al. | | 2004/0074785 A1 | 4/2004 | Holker |
| 7,917,186 B2 | 3/2011 | Kamath et al. | | 2004/0078219 A1 | 4/2004 | Kaylor |
| 2001/0016682 A1 | 8/2001 | Berner et al. | | 2004/0106857 A1 | 6/2004 | Gough |
| 2001/0020546 A1 | 9/2001 | Eldridge | | 2004/0106859 A1 | 6/2004 | Say et al. |
| 2001/0041830 A1 | 11/2001 | Varalli et al. | | 2004/0133131 A1 | 7/2004 | Kuhn et al. |
| 2001/0051768 A1 | 12/2001 | Schulman et al. | | 2004/0133164 A1 | 7/2004 | Funderburk et al. |
| 2002/0016535 A1 | 2/2002 | Martin et al. | | 2004/0143173 A1 | 7/2004 | Reghabi et al. |
| 2002/0019022 A1 | 2/2002 | Dunn et al. | | 2004/0152187 A1 | 8/2004 | Haight et al. |
| 2002/0023852 A1 | 2/2002 | McIvor et al. | | 2004/0152622 A1 | 8/2004 | Keith et al. |
| 2002/0026111 A1 | 2/2002 | Ackerman | | 2004/0158138 A1 | 8/2004 | Kilcoyne et al. |
| 2002/0042090 A1 | 4/2002 | Heller et al. | | 2004/0167801 A1 | 8/2004 | Say et al. |
| 2002/0042561 A1 | 4/2002 | Schulman et al. | | 2004/0173472 A1 | 9/2004 | Jung et al. |
| 2002/0045808 A1 | 4/2002 | Ford et al. | | 2004/0186362 A1 | 9/2004 | Brauker et al. |
| 2002/0055673 A1 | 5/2002 | Van Antwerp et al. | | 2004/0186365 A1 | 9/2004 | Jin et al. |
| 2002/0065453 A1 | 5/2002 | Lesho et al. | | 2004/0199059 A1 | 10/2004 | Brauker et al. |
| 2002/0068860 A1 | 6/2002 | Clark, Jr. | | 2004/0204687 A1 | 10/2004 | Morgensen |
| 2002/0084196 A1 | 7/2002 | Liamos et al. | | 2004/0236200 A1 | 11/2004 | Say et al. |
| 2002/0099282 A1 | 7/2002 | Knobbe et al. | | 2004/0236251 A1 | 11/2004 | Roe et al. |
| 2002/0099997 A1 | 7/2002 | Piret | | 2004/0242982 A1 | 12/2004 | Sakata et al. |
| 2002/0111547 A1 | 8/2002 | Knobbe et al. | | 2004/0248282 A1 | 12/2004 | Sobha et al. |
| 2002/0119711 A1 | 8/2002 | Van Antwerp et al. | | 2004/0254433 A1 | 12/2004 | Bandis |
| 2002/0123048 A1 | 9/2002 | Gau | | 2005/0006122 A1 | 1/2005 | Burnette |
| 2002/0155615 A1 | 10/2002 | Novikov et al. | | 2005/0008671 A1 | 1/2005 | Van Antwerp |
| 2002/0160722 A1 | 10/2002 | Terranova et al. | | 2005/0026689 A1 | 2/2005 | Marks |
| 2002/0161288 A1 | 10/2002 | Shin et al. | | 2005/0027180 A1 | 2/2005 | Goode et al. |
| 2002/0169369 A1 | 11/2002 | Ward et al. | | 2005/0027181 A1* | 2/2005 | Goode et al. .................. 600/365 |
| 2002/0177763 A1 | 11/2002 | Burns et al. | | 2005/0027182 A1 | 2/2005 | Siddiqui et al. |
| 2002/0177764 A1 | 11/2002 | Sohrab et al. | | 2005/0027462 A1 | 2/2005 | Goode et al. |
| 2002/0188185 A1 | 12/2002 | Sohrab | | 2005/0027463 A1 | 2/2005 | Goode et al. |
| 2002/0188216 A1 | 12/2002 | Kayyali et al. | | 2005/0031689 A1 | 2/2005 | Shults et al. |
| 2002/0198513 A1 | 12/2002 | Lebel et al. | | 2005/0033132 A1 | 2/2005 | Shults et al. |
| 2003/0003524 A1 | 1/2003 | Taniike et al. | | 2005/0038332 A1 | 2/2005 | Saidara et al. |
| 2003/0004457 A1 | 1/2003 | Andersson | | 2005/0043598 A1 | 2/2005 | Goode et al. |
| 2003/0006669 A1 | 1/2003 | Pei et al. | | 2005/0051427 A1 | 3/2005 | Brauker et al. |
| 2003/0023171 A1 | 1/2003 | Sato et al. | | 2005/0051440 A1 | 3/2005 | Simpson et al. |
| 2003/0023317 A1 | 1/2003 | Brauker et al. | | 2005/0054909 A1 | 3/2005 | Petisce et al. |
| 2003/0028089 A1 | 2/2003 | Galley et al. | | 2005/0056551 A1 | 3/2005 | White et al. |
| 2003/0032874 A1 | 2/2003 | Rhodes et al. | | 2005/0056552 A1 | 3/2005 | Simpson et al. |

| | | | | | | |
|---|---|---|---|---|---|---|
| 2005/0090607 A1 | 4/2005 | Tapsak et al. | | 2007/0038044 A1 | 2/2007 | Dobbles et al. |
| 2005/0096519 A1 | 5/2005 | DeNuzzio et al. | | 2007/0045902 A1 | 3/2007 | Brauker et al. |
| 2005/0101847 A1 | 5/2005 | Routt et al. | | 2007/0049873 A1 | 3/2007 | Hansen et al. |
| 2005/0103625 A1 | 5/2005 | Rhodes et al. | | 2007/0066873 A1 | 3/2007 | Kamath et al. |
| 2005/0112169 A1 | 5/2005 | Brauker et al. | | 2007/0073129 A1 | 3/2007 | Shah et al. |
| 2005/0113653 A1 | 5/2005 | Fox et al. | | 2007/0093704 A1 | 4/2007 | Brister et al. |
| 2005/0115832 A1 | 6/2005 | Simpson et al. | | 2007/0173709 A1 | 7/2007 | Petisce et al. |
| 2005/0121322 A1 | 6/2005 | Say | | 2007/0173710 A1 | 7/2007 | Petisce et al. |
| 2005/0133368 A1 | 6/2005 | Davies et al. | | 2007/0173711 A1 | 7/2007 | Shah et al. |
| 2005/0139489 A1 | 6/2005 | Davies et al. | | 2007/0200254 A1 | 8/2007 | Curry |
| 2005/0143635 A1 | 6/2005 | Kamath et al. | | 2007/0202672 A1 | 8/2007 | Curry |
| 2005/0143675 A1 | 6/2005 | Neel et al. | | 2007/0203410 A1 | 8/2007 | Say et al. |
| 2005/0154271 A1 | 7/2005 | Rasdal et al. | | 2007/0203966 A1 | 8/2007 | Brauker et al. |
| 2005/0176136 A1 | 8/2005 | Burd et al. | | 2007/0208244 A1 | 9/2007 | Brauker et al. |
| 2005/0177036 A1 | 8/2005 | Shults et al. | | 2007/0208245 A1 | 9/2007 | Brauker et al. |
| 2005/0181012 A1 | 8/2005 | Saint et al. | | 2007/0208246 A1 | 9/2007 | Brauker et al. |
| 2005/0182451 A1 | 8/2005 | Griffin et al. | | 2007/0213610 A1 | 9/2007 | Say et al. |
| 2005/0183954 A1 | 8/2005 | Hitchcock et al. | | 2007/0213611 A1 | 9/2007 | Simpson et al. |
| 2005/0187720 A1 | 8/2005 | Goode, Jr. et al. | | 2007/0232876 A1 | 10/2007 | Otto et al. |
| 2005/0192557 A1 | 9/2005 | Brauker et al. | | 2007/0232879 A1 | 10/2007 | Brister et al. |
| 2005/0195930 A1 | 9/2005 | Spital et al. | | 2007/0235331 A1 | 10/2007 | Simpson et al. |
| 2005/0203360 A1 | 9/2005 | Brauker et al. | | 2007/0259217 A1 | 11/2007 | Logan |
| 2005/0211571 A1 | 9/2005 | Schulein et al. | | 2008/0021666 A1 | 1/2008 | Goode et al. |
| 2005/0215871 A1 | 9/2005 | Feldman et al. | | 2008/0033254 A1 | 2/2008 | Kamath et al. |
| 2005/0215872 A1 | 9/2005 | Berner et al. | | 2008/0154101 A1 | 6/2008 | Jain et al. |
| 2005/0239154 A1 | 10/2005 | Feldman et al. | | 2008/0183061 A1 | 7/2008 | Goode et al. |
| 2005/0242479 A1 | 11/2005 | Petisce et al. | | 2008/0183399 A1 | 7/2008 | Goode et al. |
| 2005/0245795 A1 | 11/2005 | Goode et al. | | 2008/0187655 A1 | 8/2008 | Markle et al. |
| 2005/0245799 A1 | 11/2005 | Brauker et al. | | 2008/0188722 A1 | 8/2008 | Markle et al. |
| 2005/0258037 A1 | 11/2005 | Hajizadeh et al. | | 2008/0188725 A1 | 8/2008 | Markle et al. |
| 2005/0261563 A1 | 11/2005 | Zhou et al. | | 2008/0188731 A1 | 8/2008 | Brister et al. |
| 2005/0271546 A1 | 12/2005 | Gerber et al. | | 2008/0189051 A1 | 8/2008 | Goode et al. |
| 2005/0272989 A1 | 12/2005 | Shah et al. | | 2008/0194936 A1 | 8/2008 | Goode et al. |
| 2006/0015020 A1 | 1/2006 | Neale et al. | | 2008/0194937 A1 | 8/2008 | Goode et al. |
| 2006/0015024 A1 | 1/2006 | Brister et al. | | 2008/0195967 A1 | 8/2008 | Goode et al. |
| 2006/0016700 A1 | 1/2006 | Brister et al. | | 2008/0208025 A1 | 8/2008 | Shults et al. |
| 2006/0019327 A1 | 1/2006 | Brister et al. | | 2008/0214915 A1 | 9/2008 | Brister et al. |
| 2006/0020186 A1 | 1/2006 | Brister et al. | | 2008/0214918 A1 | 9/2008 | Brister et al. |
| 2006/0020187 A1 | 1/2006 | Brister et al. | | 2008/0242961 A1 | 10/2008 | Brister et al. |
| 2006/0020188 A1 | 1/2006 | Kamath et al. | | 2008/0262334 A1 | 10/2008 | Dunn et al. |
| 2006/0020189 A1 | 1/2006 | Brister et al. | | 2008/0275313 A1 | 11/2008 | Brister et al. |
| 2006/0020190 A1 | 1/2006 | Kamath et al. | | 2008/0287764 A1 | 11/2008 | Rasdal et al. |
| 2006/0020191 A1 | 1/2006 | Brister et al. | | 2008/0287765 A1 | 11/2008 | Rasdal et al. |
| 2006/0020192 A1 | 1/2006 | Brister et al. | | 2008/0287766 A1 | 11/2008 | Rasdal et al. |
| 2006/0036139 A1 | 2/2006 | Brister et al. | | 2008/0296155 A1 | 12/2008 | Shults et al. |
| 2006/0036140 A1 | 2/2006 | Brister et al. | | 2008/0305009 A1 | 12/2008 | Gamsey et al. |
| 2006/0036141 A1 | 2/2006 | Kamath et al. | | 2008/0305506 A1 | 12/2008 | Suri |
| 2006/0036142 A1 | 2/2006 | Brister et al. | | 2008/0306368 A1 | 12/2008 | Goode et al. |
| 2006/0036143 A1 | 2/2006 | Brister et al. | | 2008/0306434 A1 | 12/2008 | Dobbles et al. |
| 2006/0036144 A1 | 2/2006 | Brister et al. | | 2008/0306435 A1 | 12/2008 | Kamath et al. |
| 2006/0036145 A1 | 2/2006 | Brister et al. | | 2008/0306444 A1 | 12/2008 | Brister et al. |
| 2006/0040402 A1 | 2/2006 | Brauker et al. | | 2009/0005666 A1 | 1/2009 | Shin et al. |
| 2006/0047215 A1 | 3/2006 | Newman et al. | | 2009/0012379 A1 | 1/2009 | Goode et al. |
| 2006/0100588 A1 | 5/2006 | Brunnberg et al. | | 2009/0018418 A1 | 1/2009 | Markle et al. |
| 2006/0142651 A1 | 6/2006 | Brister et al. | | 2009/0018426 A1 | 1/2009 | Markle et al. |
| 2006/0155180 A1 | 7/2006 | Brister et al. | | 2009/0030297 A1 | 1/2009 | Miller et al. |
| 2006/0173444 A1 | 8/2006 | Choy et al. | | 2009/0036758 A1 | 2/2009 | Brauker et al. |
| 2006/0183984 A1 | 8/2006 | Dobbles et al. | | 2009/0043181 A1 | 2/2009 | Brauker et al. |
| 2006/0183985 A1 | 8/2006 | Brister et al. | | 2009/0043182 A1 | 2/2009 | Brauker et al. |
| 2006/0189856 A1 | 8/2006 | Petisce et al. | | 2009/0043525 A1 | 2/2009 | Brauker et al. |
| 2006/0195029 A1 | 8/2006 | Shults et al. | | 2009/0043541 A1 | 2/2009 | Brauker et al. |
| 2006/0200020 A1 | 9/2006 | Brister et al. | | 2009/0043542 A1 | 2/2009 | Brauker et al. |
| 2006/0200022 A1 | 9/2006 | Brauker et al. | | 2009/0045055 A1 | 2/2009 | Rhodes et al. |
| 2006/0211921 A1 | 9/2006 | Brauker et al. | | 2009/0061528 A1 | 3/2009 | Suri |
| 2006/0222566 A1 | 10/2006 | Brauker et al. | | 2009/0062633 A1 | 3/2009 | Brauker et al. |
| 2006/0224108 A1 | 10/2006 | Brauker et al. | | 2009/0062635 A1 | 3/2009 | Brauker et al. |
| 2006/0229512 A1 | 10/2006 | Petisce et al. | | 2009/0062645 A1 | 3/2009 | Brauker et al. |
| 2006/0235285 A1 | 10/2006 | Brister et al. | | 2009/0076356 A1 | 3/2009 | Simpson |
| 2006/0258761 A1 | 11/2006 | Boock et al. | | 2009/0076361 A1 | 3/2009 | Kamath et al. |
| 2006/0258929 A1 | 11/2006 | Goode, Jr. et al. | | 2009/0081803 A1 | 3/2009 | Gamsey et al. |
| 2006/0270922 A1 | 11/2006 | Brauker et al. | | 2009/0099434 A1 | 4/2009 | Liu et al. |
| 2006/0270923 A1 | 11/2006 | Brauker et al. | | 2009/0099436 A1 | 4/2009 | Brister et al. |
| 2006/0281985 A1 | 12/2006 | Ward et al. | | 2009/0124877 A1 | 5/2009 | Goode, Jr. et al. |
| 2007/0016381 A1 | 1/2007 | Kamath et al. | | 2009/0124878 A1 | 5/2009 | Goode, Jr. et al. |
| 2007/0017805 A1 | 1/2007 | Hodges et al. | | 2009/0124879 A1 | 5/2009 | Brister et al. |
| 2007/0027385 A1 | 2/2007 | Brister et al. | | 2009/0143660 A1 | 6/2009 | Brister et al. |
| 2007/0032706 A1 | 2/2007 | Kamath et al. | | 2009/0156924 A1 | 6/2009 | Shariati et al. |
| 2007/0032717 A1 | 2/2007 | Brister et al. | | 2009/0177143 A1 | 7/2009 | Markle et al. |
| 2007/0032718 A1 | 2/2007 | Shults et al. | | 2009/0182217 A1 | 7/2009 | Li et al. |

| | | | | | |
|---|---|---|---|---|---|
| 2009/0192366 A1 | 7/2009 | Mensinger et al. | EP | 0 885 932 | 12/1998 |
| 2009/0192380 A1 | 7/2009 | Shariati et al. | EP | 0 967 788 | 12/1999 |
| 2009/0192722 A1 | 7/2009 | Shariati et al. | EP | 1 077 634 | 2/2001 |
| 2009/0192724 A1 | 7/2009 | Brauker et al. | EP | 1 078 258 | 2/2001 |
| 2009/0192745 A1 | 7/2009 | Kamath et al. | EP | 0 958 495 | 11/2002 |
| 2009/0192751 A1 | 7/2009 | Kamath et al. | EP | 2 226 086 | 8/2010 |
| 2009/0203981 A1 | 8/2009 | Brauker et al. | FR | 2656423 | 6/1991 |
| 2009/0204341 A1 | 8/2009 | Brauker et al. | FR | 2760962 | 9/1998 |
| 2009/0216103 A1 | 8/2009 | Brister et al. | GB | 1 442 303 | 7/1976 |
| 2009/0240120 A1 | 9/2009 | Mensinger et al. | GB | 1 556 969 | 12/1979 |
| 2009/0240128 A1 | 9/2009 | Mensinger et al. | GB | 2149918 | 6/1985 |
| 2009/0240193 A1 | 9/2009 | Mensinger et al. | JP | 62058154 | 3/1987 |
| 2009/0242399 A1 | 10/2009 | Kamath et al. | JP | 62083649 | 4/1987 |
| 2009/0242425 A1 | 10/2009 | Kamath et al. | JP | 63067560 | 3/1988 |
| 2009/0247857 A1 | 10/2009 | Harper et al. | JP | 02002913 | 1/1990 |
| 2009/0264719 A1 | 10/2009 | Markle et al. | JP | 3-293556 | 12/1991 |
| 2009/0264856 A1 | 10/2009 | Lebel et al. | JP | 62083849 | 4/1997 |
| 2009/0287074 A1 | 11/2009 | Shults et al. | JP | 2002513602 | 5/2002 |
| 2009/0299162 A1 | 12/2009 | Brauker et al. | JP | 2002-189015 | 7/2002 |
| 2009/0299276 A1 | 12/2009 | Brauker et al. | WO | WO 87/63242 | 10/1987 |
| 2010/0010324 A1 | 1/2010 | Brauker et al. | WO | WO 89/02720 | 4/1989 |
| 2010/0010331 A1 | 1/2010 | Brauker et al. | WO | WO 90/00738 | 1/1990 |
| 2010/0010332 A1 | 1/2010 | Brauker et al. | WO | WO 90/10861 | 9/1990 |
| 2010/0016687 A1 | 1/2010 | Brauker et al. | WO | WO 91/09302 | 6/1991 |
| 2010/0022855 A1 | 1/2010 | Brauker et al. | WO | WO 92/07525 | 5/1992 |
| 2010/0030053 A1 | 2/2010 | Goode, Jr. et al. | WO | WO 92/13271 | 8/1992 |
| 2010/0030484 A1 | 2/2010 | Brauker et al. | WO | WO 93/05701 | 4/1993 |
| 2010/0030485 A1 | 2/2010 | Brauker et al. | WO | WO 93/14693 | 8/1993 |
| 2010/0036215 A1 | 2/2010 | Goode, Jr. et al. | WO | WO 93/23744 | 11/1993 |
| 2010/0036216 A1 | 2/2010 | Goode, Jr. et al. | WO | WO 93/25898 | 12/1993 |
| 2010/0036222 A1 | 2/2010 | Goode, Jr. et al. | WO | WO 94/22367 | 10/1994 |
| 2010/0036223 A1 | 2/2010 | Goode, Jr. et al. | WO | WO 96/14026 | 5/1996 |
| 2010/0036224 A1 | 2/2010 | Goode, Jr. et al. | WO | WO 96/25089 | 8/1996 |
| 2010/0036225 A1 | 2/2010 | Goode, Jr. et al. | WO | WO 96/30431 | 10/1996 |
| 2010/0041971 A1 | 2/2010 | Goode, Jr. et al. | WO | WO 97/01986 | 1/1997 |
| 2010/0045465 A1 | 2/2010 | Brauker et al. | WO | WO 97/06727 | 2/1997 |
| 2010/0049024 A1 | 2/2010 | Saint et al. | WO | WO 97/28737 | 8/1997 |
| 2010/0081908 A1 | 4/2010 | Dobbles et al. | WO | WO 98/19159 | 5/1998 |
| 2010/0161269 A1 | 6/2010 | Kamath et al. | WO | WO 98/24358 | 6/1998 |
| 2010/0174158 A1 | 7/2010 | Kamath et al. | WO | WO 98/38906 | 9/1998 |
| 2010/0174167 A1 | 7/2010 | Kamath et al. | WO | WO 99/56613 | 4/1999 |
| 2010/0174168 A1 | 7/2010 | Goode et al. | WO | WO 99/48419 | 9/1999 |
| 2010/0179399 A1 | 7/2010 | Goode et al. | WO | WO 99/58051 | 11/1999 |
| 2010/0179405 A1 | 7/2010 | Goode et al. | WO | WO 99/58709 | 11/1999 |
| 2010/0179406 A1 | 7/2010 | Goode et al. | WO | WO 99/58973 | 11/1999 |
| 2010/0185065 A1 | 7/2010 | Goode et al. | WO | WO 00/12720 | 3/2000 |
| 2010/0185070 A1 | 7/2010 | Brister et al. | WO | WO 00/19887 | 4/2000 |
| 2010/0185071 A1 | 7/2010 | Simpson et al. | WO | WO 00/32098 | 6/2000 |
| 2010/0185072 A1 | 7/2010 | Goode et al. | WO | WO 00/33065 | 6/2000 |
| 2010/0185073 A1 | 7/2010 | Goode et al. | WO | WO 00/59373 | 10/2000 |
| 2010/0185074 A1 | 7/2010 | Goode et al. | WO | WO 00/74753 | 12/2000 |
| 2010/0198035 A1 | 8/2010 | Kamath et al. | WO | WO 00/78210 | 12/2000 |
| 2010/0198036 A1 | 8/2010 | Kamath et al. | WO | WO 00/79258 | 12/2000 |
| 2010/0204555 A1 | 8/2010 | Shults et al. | WO | WO 01/16579 | 3/2001 |
| 2010/0214104 A1 | 8/2010 | Goode et al. | WO | WO 01/20334 | 3/2001 |
| 2010/0217106 A1 | 8/2010 | Goode et al. | WO | WO 01/34243 | 5/2001 |
| 2010/0217555 A1 | 8/2010 | Goode et al. | WO | WO 01/58348 | 8/2001 |
| 2010/0234796 A1 | 9/2010 | Kamath et al. | WO | WO 01/68901 | 9/2001 |
| 2010/0286496 A1 | 11/2010 | Simpson et al. | WO | WO 01/69222 | 9/2001 |
| 2010/0331648 A1 | 12/2010 | Kamath et al. | WO | WO 01/88524 | 11/2001 |
| 2011/0046467 A1 | 2/2011 | Simpson et al. | WO | WO 01/88534 | 11/2001 |
| FOREIGN PATENT DOCUMENTS | | | WO | WO 02/05702 | 1/2002 |
| EP | 0 098 592 | 1/1984 | WO | WO 02/24065 | 3/2002 |
| EP | 0 127 958 | 12/1984 | WO | WO 02/082989 | 10/2002 |
| EP | 0 284 518 | 9/1988 | WO | WO 02/097414 | 12/2002 |
| EP | 0 286 118 | 10/1988 | WO | WO 02/100266 | 12/2002 |
| EP | 0 320 109 | 6/1989 | WO | WO 03/011131 | 2/2003 |
| EP | 0 353 328 | 2/1990 | WO | WO 03/012422 | 2/2003 |
| EP | 0 390 390 | 10/1990 | WO | WO 03/032411 | 4/2003 |
| EP | 0 396 788 | 11/1990 | WO | WO 03/082091 | 9/2003 |
| EP | 0 476 980 | 3/1992 | WO | WO 2005/011489 | 2/2005 |
| EP | 0 534 074 | 3/1993 | WO | WO 2005/012873 | 2/2005 |
| EP | 0 539 625 | 5/1993 | WO | WO 2005/057168 | 6/2005 |
| EP | 0 563 795 | 10/1993 | WO | WO 2005/057173 | 6/2005 |
| EP | 0 690 134 | 1/1996 | WO | WO 2005/057175 | 6/2005 |
| EP | 0 817 809 | 1/1998 | WO | WO 2005/026689 | 10/2005 |
| EP | 0 838 230 | 4/1998 | WO | WO 2005/122296 | 12/2005 |
| EP | 0 880 936 | 12/1998 | | | |

| WO | WO 2006/017358 | 2/2006 |
| WO | WO 2006/105146 | 10/2006 |
| WO | WO 2008/076868 | 6/2008 |

OTHER PUBLICATIONS

Bardeletti et al. 1986. A Reliable L-Lactate Electrode with a New Membrane for Enzyme Immobilization for Amperometric Assay of Lactate. Analyt Chim Acta, 187: 47-54.
Bertrand et al. 1981 Multipurpose Electrode with Different Enzyme Systems Bound to Collagen Films. Anal Chim Acta 126: 23-34.
Coulet et al. (1981) Enzymes immobilized on collagen membranes: A tool for fundamental research and enzyme engineering. J Chromatography 215: 65-72.
Coulet, P.R. 1992. Polymeric membranes and coupled enzymes in the design of biosensors. J Membr Science 68: 217-228.
Peguin et al. 1989. Pyruvate Oxidase and Oxaloacetate Decarbozylase Enzyme Electrodes-Simultaneous Determination of Transaminases with a Two-electrode-based Analyzer, Anal Chim Acta 222: 83-93.
Schaffar, Bernhard P.H. (Dec. 2001). Thick film biosensors for metabolites in undiluted whole blood and plasma samples, Anal Bioanal Chem. 372: 254-260.
Takatsu et al. 1987. Solid State Biosensors Using Thin-Film Electrodes. Sens Actuators 11: 309-317.
Yang et al. 1995. Glucose Biosensors with enzyme entrapped in polymer coating, Biomed Instrum Technol. 29(2): 125-133.
EPO Notice of Opposition dated Jun. 20, 2011 by Roche Diagnostics GmbH against EP Patent No. 1711790, issued Oct. 18, 2006.
Roche Diagnostics GmbH Grounds of Opposition dated Jun. 6, 2011 against EP 1711790, issued Sep. 8, 2010.
Abbott Diabetes Care Inc. Grounds of Opposition dated Mar. 30, 2011 against EP 1711790, issued Sep. 8, 2010.
Electronic File History of Reissue U.S. Appl. No. 12/839,260, filed Jul. 19, 2010 containing Office Action(s) dated Aug. 9, 2010, Feb. 28, 2011, and Jul. 25, 2011 and Applicant Response(s) filed Jul. 19, 2010, Apr. 1, 2011 as of Jul. 25, 2011.
Armour et al. Dec. 1990. Application of Chronic Intravascular Blood Glucose Sensor in Dogs. Diabetes 39:1519-1526.
Atanasov et al. 1994. Biosensor for continuous glucose monitoring. Biotechnology and Bioengineering 43:262-266.
Aussedat et al. 1997. A user-friendly method for calibrating a subcutaneous glucose sensor-based hypoglycaemic alarm. Biosensors & Bioelectronics 12(11):1061-1071.
Bani Amer, M. M. 2002. An accurate amperometric glucose sensor based glucometer with eliminated cross-sensitivity. J Med Eng Technol 26(5):208-213.
Bard et al. 1980. Electrochemical Methods. John Wiley & Sons, pp. 173-175.
Bellucci et al. Jan. 1986. Electrochemical behaviour of graphite-epoxy composite materials (GECM) in aqueous salt solutions, Journal of Applied Electrochemistry, 16(1):15-22.
Bindra et al. 1991. Design and In Vitro Studies of a Needle-Type Glucose Senso for Subcutaneous Monitoring. Anal. Chem 63:1692-96.
Bland et al. 1986. Statistical methods for assessing agreement between two methods of clinical measurement. Lancet 1:307-310.
Bobbioni-Harsch et al. 1993. Lifespan of subcutaneous glucose sensors and their performances during dynamic glycaemia changes in rats, J. Biomed. Eng. 15:457-463.
Bott, A. W. 1997. A Comparison of Cyclic Voltammetry and Cyclic Staircase Voltammetry Current Separations 16:1, 23-26.
Brooks et al. "Development of an on-line glucose sensor for fermentation monitoring," Biosensors, 3:45-56 (1987/88).
Candas et al (1994). "An adaptive plasma glucose controller basedon a nonlinear insulin/glucose model." *IEEE Transactions on Biomedical Engineering*, 41(2): 116-124.
Cass et al. "Ferrocene-mediated enzyme electrodes for amperometric determination of glucose," Anal. Chem., 36:667-71 (1984).
Chia et al. 2004. Glucose sensors: toward closed loop insulin delivery. Endocrinol Metab Clin North Am 33:175-95.
Choleau et al. 2002. Calibration of a subcutaneous amperometric glucose sensor implanted for 7 days in diabetic patients. Part 1. Effect of measurement uncertainties on the determination of sensor sensitivity and background current. Biosensors and Bioel.
Choleau et al. 2002. Calibration of a subcutaneous amperometric glucose sensor implanted for 7 days in diabetic patients. Part 2. Superiority of the one-point calibration method. Biosensors and Bioelectronics 17:647-654.
Csöregi et al. 1994. Amperometric microbiosensors for detection of hydrogen peroxide and glucose based on peroxidase-modified carbon fibers. Electroanalysis 6:925-933.
Davies, et al. 1992. Polymer membranes in clinical sensor applications. I. An overview of membrane function, Biomaterials, 13(14):971-978.
El-Khatib et al. 2007. Adaptive closed-loop control provides blood-glucose regulation using dual subcutaneous insulin and glucagon infusion in diabetic swine, Journal of Diabetes Science and Technology, 1(2):181-192.
Ernst et al. 2002. Reliable glucose monitoring through the use of microsystem technology. Anal. Bioanal. Chem. 373:758-761.
Fabietti et al. 2007. Clinical validation of a new control-oriented model of insulin and glucose dynamcs in subjects with type 1 diabetes, Diabetes Technology & Therapeutics, 9(4):327-338.
Fare et al. 1998. Functional characterization of a conducting polymer-based immunoassay system. Biosensors & Bioelectronics 13(3-4):459-470.
Feldman et al. 2003. A continuous glucose sensor based on wired enzyme technology—results from a 3-day trial in patients with type 1 diabetes. Diabetes Technol Ther 5(5):769-779.
Frohnauer et al. 2001. Graphical human insulin time-activity profiles using standardized definitions. Diabetes Technology & Therapeutics 3(3):419-429.
Gilligan et al. 1994. Evaluation of a subcutaneous glucose sensor out to 3 months in a dog model. Diabetes Care 17(8):882-887.
Gilligan et al. 2004, Feasibility of continuous long-term glucose monitoring from a subcutaneous glucose sensor in humans. Diabetes Technol Ther 6:378-386.
Gouda et al., Jul. 4, 2003. Thermal inactiviation of glucose oxidase, The Journal of Biological Chemistry, 278(27):24324-24333.
Guerci et al., Clinical performance of CGMS in type 1 diabetic patents treated by continuous subcutaneous insulin infusion using insulin analogs, Diabetes Care, 26:582-589, 2003.
Harrison et al. 1988. Characterization of perfluorosulfonic acid polymer coated enzyme electrodes and a miniaturized integrated potentiostat for glucose analysis in whole blood. Anal. Chem. 60:2002-2007.
Heller, "Electrical wiring of redox enzymes," Acc. Chem. Res., 23:128-134 (1990).
Heller, A. 1992. Electrical Connection of Enzyme Redox Centers to Electrodes. J. Phys. Chem. 96:3579-3587.
Hicks, 1985. In Situ Monitoring, Clinical Chemistry, 31(12):1931-1935.
Hu, et al. 1993. A needle-type enzyme-based lactate sensor for in vivo monitoring, Analytica Chimica Acta, 281:503-511.
Hunter et al. 2000. Minimally Invasive Glucose Sensor and Insulin Delivery System. MIT Home Automation and Healthcare Consortium. Progress Report No. 25.
Jeong et al. 2003. In vivo calibration of the subcutaneous amperometric glucose sensors using a non-enzyme electrode. Biosensors and Bioelectronics 19:313-319.
Johnson et al. 1992. In vivo evaluation of an electroenzymatic glucose sensor implanted in subcutaneous tissue. Biosensors & Bioelectronics, 7:709-714.
Kamath et al. Calibration of a continuous glucose monitor: effect of glucose rate of change, Eighth Annual Diabetes Technology Meeting, Nov. 13-15, 2008, p. A88.
Kawagoe et al. 1991. Enzyme-modified organic conducting salt microelectrode, Anal. Chem. 63:2961-2965.
Kerner et al. "The function of a hydrogen peroxide-detecting electroenzymatic glucose electrode is markedly impaired in human sub-cutaneous tissue and plasma," Biosensors & Bioelectronics, 8:473-482 (1993).
Koschinsky et al. 1988. New approach to technical and clinical evaluation of devices for self-monitoring of blood glucose. Diabetes Care 11(8): 619-619.

Kurnik et al. 1999. Application of the mixtures of experts algorithm for signal processing in a noninvasive glucose monitoring system. Sensors and Actuators B, 60:19-26.

Lohn et al., A knowledge-based system for real-time validation of calibrations and measurements, Chemometrics and Intelligent Laboratory Systems, 1999 46, 57-66.

Maidan et al. 1992. Elimination of Electrooxidizable Interferent-Produced Currents in Amperometric Biosensors, Analytical Chemistry, 64:2889-2896.

Martin, R. F. 2000. General Deming regression for estimating systematic bias and its confidence interval in method-comparison studies. *Clinical Chemistry*, 46(1):100-104.

Mastrototaro et al. "An electroenzymatic glucose sensor fabricated on a flexible substrate," Sensors and Actuators B, 5:139-44 (1991).

Matsumoto et al. 1998. A micro-planar amperometeric glucose sensor unsusceptible to interference species. Sensors and Actuators B 49:68-72.

Matsumoto et al. 2001. A long-term lifetime amperometric glucose sensor with a perfluorocarbon polymer coating. Biosens Bioelectron 16:271-276.

McGrath et al. 1995. The use of differential measurements with a glucose biosensor for interference compensation during glucose determinations by flow injection analysis. Biosens Bioelectron 10:937-943.

McKean, et al. Jul. 7, 1988. A Telemetry Instrumentation System for Chronically Implanted Glucose and Oxygen Sensors. Transactions on Biomedical Engineering 35:526-532.

Memoli et al. 2002. A comparison between different immobilised glucoseoxidase-based electrodes. J Pharm Biomed Anal 29:1045-1052.

Moatti-Sirat et al. 1992. Evaluating in vitro and in vivo the interference of ascorbate and acetaminophen on glucose detection by a needle-type glucose sensor, Biosensors & Bioelectronics 7:345-352.

Moatti-Sirat et al. 1992. Towards continuous glucose monitoring: in vivo evaluation of a miniaturized glucose sensor implanted for several days in rat subcutaneous tissue. Diabetologia 35:224-230.

Murphy, et al. 1992. Polymer membranes in clinical sensor applications. II. The design and fabrication of permselective hydrogels for electrochemical devices, Biomaterials, 13(14):979-990.

Ohara et al. 1994. "Wired" enzyme electrodes for amperometric determination of glucose or lactate in the presence of interfering substances. Anal Chem 66:2451-2457.

Ohara, et al. Dec. 1993. Glucose electrodes based on cross-linked bis(2,2'-bipyridine)chloroosmium(+/2+) complexed poly(1-vinylimidazole) films, Analytical Chemistry, 65:3512-3517.

Palmisano et al. 2000. Simultaneous monitoring of glucose and lactate by an interference and cross-talk free dual electrode amperometric biosensor based on electropolymerized thin films. Biosensors & Bioelectronics 15:531-539.

Pickup et al. "Implantable glucose sensors: choosing the appropriate sensing strategy," Biosensors, 3:335-346 (1987/88).

Pickup et al. "In vivo molecular sensing in diabetes mellitus: an implantable glucose sensor with direct electron transfer," Diabetologia, 32:213-217 (1989).

Pishko et al. "Amperometric glucose microelectrodes prepared through immobilization of glucose oxidase in redox hydrogels," Anal. Chem., 63:2268-72 (1991).

Poitout et al. 1993. A glucose monitoring system for on line estimation in man of blood glucose concentration using a miniaturized glucose sensor implanted in the subcutaneous tissue and a wearable control unit. Diabetologia 36:658-663.

Poitout, et al. 1991. In Vitro and In Vivo Evaluation in Dogs of a Miniaturized Glucose Sensor, ASAIO Transactions, 37:M298-M300.

Postlethwaite et al. 1996. Interdigitated array electrode as an alternative to the rotated ring-disk electrode for determination of the reaction products of dioxygen reduction. Analytical Chemistry 68:2951-2958.

Prabhu et al. 1981. Electrochemical studies of hydrogen peroxide at a platinum disc electrode, Electrochimica Acta 26(6):725-729.

Reach et al. 1992. Can continuous glucose monitoring be used for the treatment of diabetes? Analytical Chemistry 64(5):381-386.

Rebrin et al. "Automated feedback control of subcutaneous glucose concentration in diabetic dogs," Diabetologia, 32:573-76 (1989).

Rhodes et al. 1994. Prediction of pocket-portable and implantable glucose enzyme electrode performance from combined species permeability and digital simulation analysis. Analytical Chemistry 66(9):1520-1529.

Rinken et al. 1998. Calibration of glucose biosensors by using pre-steady state kinetic data. Biosensors & Bioelectronics, 13:801-807.

Sakakida et al. 1993. Ferrocene-Mediated Needle Type Glucose Sensor Covered with Newly Designed Biocompatible Membran, Sensors and Actuators B 13-14:319-322.

Service et al. 1970. Mean amplitude of glycemic excursions, a measure of diabetic instability. Diabetes, 19: 644-655.

Shaw et al. "In vitro testing of a simply constructed, highly stable glucose sensor suitable for implantation in diabetic patients," Biosensors & Bioelectronics, 6:401-406 (1991).

Shichiri et al. 1985. Needle-type Glucose Sensor for Wearable Artificial Endocrine Pancreas in Implantable Sensors 197-210.

Shichiri et al. 1986. Telemetry Glucose Monitoring Device with Needle-Type Glucose Sensor: A Useful Tool for Blood Glucose Monitoring in Diabetic Individuals. Diabetes Care, Inc. 9(3):298-301.

Shichiri et al. 1989. Membrane Design For Extending the Long-Life of an Implantable Glucose Sensor. Diab. Nutr. Metab. 2:309-313.

Shults et al. 1994. A telemetry-instrumentation system for monitoring multiple subcutaneously implanted glucose sensors. IEEE Transactions on Biomedical Engineering 41(10):937-942.

Sokol et al. 1980, Immobilized-enzyme rate-determination method for glucose analysis, Clin. Chem. 26(1):89-92.

Sternberg et al. 1988. Study and Development of Multilayer Needle-type Enzyme-based Glucose Microsensors. Biosensors 4:27-40.

Thompson et al., In Vivo Probes: Problems and Perspectives, Department of Chemistry, University of Toronto, Canada, pp. 255-261, 1986.

Tierney et al. 2000. Effect of acetaminophen on the accuracy of glucose measurements obtained with the GlucoWatch biographer. Diabetes Technol Ther 2:199-207.

Turner and Pickup, "Diabetes mellitus: biosensors for research and management," *Biosensors*, 1:85-115 (1985).

Turner, A.P.F. 1988. Amperometric biosensor based on mediator-modified electrodes. Methods in Enzymology 137:90-103.

Updike et al. 1979. Continuous glucose monitor based on an immobilized enzyme electrode detector. J Lab Clin Med, 93(4):518-527.

Updike et al. 1982. Implanting the glucose enzyme electrode: Problems, progress, and alternative solutions. Diabetes Care, 5(3):207-212.

Updike et al. 1994. Enzymatic glucose sensor: Improved long-term performance in vitro and in vivo. ASAIO Journal, 40(2):157-163.

Updike et al. 1997. Principles of long-term fully implanted sensors with emphasis on radiotelemetric monitoring of blood glucose form inside a subcutaneous foreign body capsule (FBC). In Fraser, ed., Biosensors in the Body. New York. John Wiley & Sons.

Velho et al. 1989. Strategies for calibrating a subcutaneous glucose sensor. Biomed Biochim Acta 48(11/12):957-964.

von Woedtke et al. 1989. In situ calibration of implanted electrochemical glucose sensors. Biomed Biochim. Acta 48(11/12):943-952.

Wagner et al. 1998. Continuous amperometric monitoring of glucose in a brittle diabetic chimpanzee with a miniature subcutaneous electrode. Proc. Natl. Acad. Sci. A, 95:6379-6382.

Ward et al. 1999. Assessment of chronically implanted subcutaneous glucose sensors in dogs: The effect of surrounding fluid masses. ASAIO Journal, 45:555-561.

Ward et al. 2000. Understanding Spontaneous Output Fluctuations of an Amperometric Glucose Sensor: Effect of Inhalation Anesthesia and e of a Nonenzyme Containing Electrode. ASAIO Journal 540-546.

Ward et al. 2000. Rise in background current over time in a subcutaneous glucose sensor in the rabbit: Relevance to calibration and accuracy. Biosensors & Bioelectronics, 15:53-61.

Wilkins et al. 1995. Glucose monitoring: state of the art and future possibilities. Med Eng Phys 18:273-288.

Wilson et al. 1992. Progress toward the development of an implantable sensor for glucose. Clin. Chem. 38(9):1613-1617.

Yang et al (1996). "A glucose biosensor based on an oxygen electrode: In-vitro performances in a model buffer solution and in blood plasma," Biomedical Instrumentation & Technology, 30:55-61.

Zhang et al. 1994. Elimination of the acetaminophen interference in an implantable glucose sensor. Analytical Chemistry 66(7):1183-1188.

Zhu et al. 2002. Planar amperometric glucose sensor based on glucose oxidase immobilized by chitosan film on prussian blue layer. Sensors, 2:127-136.

English translation of Office Action in Japanese App. No. 10/538680.

European Search Report for App. No. 98908875.2 dated Apr. 29, 2004.

IPRP for PCT/US04/40476.

IPRP for PCT/US06/38820 filed Oct. 4, 2006.

IPRP for PCT/US07/080228, filed Oct. 2, 2007.

ISR and WO for PCT/US06/38820 filed Oct. 4, 2006.

ISR and WO for PCT/US07/080228, filed Oct. 2, 2007.

ISR and WO PCT/US04/40476.

Office Action dated Sep. 24, 2003 in U.S. Appl. No. 09/916,711.
Office Action dated Feb. 11, 2004 in U.S. Appl. No. 09/916,711.
Office Action dated Jul. 23, 2004 in U.S. Appl. No. 09/916,711.
Office Action dated Dec. 23, 2004 in U.S. Appl. No. 09/916,711.
Office Action dated Jul. 1, 2005 in U.S. Appl. No. 09/916,711.
Office Action dated Feb. 14, 2006 in U.S. Appl. No. 09/916,711.
Office Action dated Sep. 5, 2006 in U.S. Appl. No. 09/916,711.
Office Action dated Jun. 19, 2008 in U.S. Appl. No. 11/021,162.
Office Action dated Dec. 7, 1998 in U.S. Appl. No. 08/811,473.
Office Action dated Aug. 15, 2001 in U.S. Appl. No. 09/447,227.
Office Action dated Jan. 17, 2002 in U.S. Appl. No. 09/447,227.
Office Action dated Jul. 15, 2002 in U.S. Appl. No. 09/447,227.
Office Action dated Jan. 16, 2003 in U.S. Appl. No. 09/447,227.
Office Action dated Jul. 9, 2003 in U.S. Appl. No. 09/447,227.
Office Action dated Nov. 28, 2003 in U.S. Appl. No. 09/447,227.
Office Action dated Sep. 22, 2005 in U.S. Appl. No. 09/447,227.
Office Action dated Apr. 4, 2006 in U.S. Appl. No. 09/447,227.
Office Action dated Aug. 1, 2006 in U.S. Appl. No. 09/447,227.
Office Action dated Mar. 9, 2007 in U.S. Appl. No. 09/447,227.
Office Action dated Jul. 17, 2007 in U.S. Appl. No. 09/447,227.
Office Action dated Jan. 23, 2008 in U.S. Appl. No. 09/447,227.
Office Action dated Jun. 12, 2008 in U.S. Appl. No. 09/447,227.
Office Action dated Dec. 11, 2008 in U.S. Appl. No. 09/447,227.
Office Action dated May 26, 2009 in U.S. Appl. No. 09/447,227.
Office Action dated Dec. 26, 2007 in U.S. Appl. No. 11/021,046.
Office Action dated Jun. 23, 2008 in U.S. Appl. No. 11/021,046.
Office Action dated Feb. 4, 2009 in U.S. Appl. No. 11/021,046.
Office Action dated Sep. 30, 2002 in U.S. Appl. No. 09/636,369.
Office Action dated Sep. 22, 2004 in U.S. Appl. No. 10/646,333.
Office Action dated Jun. 6, 2005 in U.S. Appl. No. 10/646,333.
Office Action dated Feb. 24, 2006 in U.S. Appl. No. 10/646,333.
Office Action dated Jun. 11, 2009 in U.S. Appl. No. 10/633,367.
Office Action dated Dec. 23, 2008 in U.S. Appl. No. 12/102,745.
Office Action dated Oct. 8, 2008 in U.S. Appl. No. 10/896,637.
Office Action dated Mar. 5, 2009 in U.S. Appl. No. 10/896,637.
Office Action dated Jul. 20, 2009 in U.S. Appl. No. 10/896,637.
Office Action dated Jan. 11, 2005 in U.S. Appl. No. 10/896,772.
Office Action dated Jul. 19, 2005 in U.S. Appl. No. 10/896,772.
Office Action dated Dec. 14, 2005 in U.S. Appl. No. 10/896,772.
Office Action dated May 22, 2006 in U.S. Appl. No. 10/896,772.
Office Action dated Oct. 18, 2005 in U.S. Appl. No. 10/897,377.
Office Action dated May 11, 2006 in U.S. Appl. No. 10/897,377.
Office Action dated Feb. 9, 2006 in U.S. Appl. No. 10/897,312.
Office Action dated Oct. 20, 2004 in U.S. Appl. No. 10/632,537.
Office Action dated Dec. 21, 2004 in U.S. Appl. No. 10/632,537.
Office Action dated May 29, 2008 in U.S. Appl. No. 95/001,039.
Office Action dated Jun. 17, 2008 in U.S. Appl. No. 11/038,340.
Office Action dated Feb. 12, 2007 in U.S. Appl. No. 10/633,404.
Office Action dated Jun. 17, 2008 in U.S. Appl. No. 95/001,038.
Office Action dated Oct. 5, 2006 in U.S. Appl. No. 10/633,329.
Office Action dated Mar. 26, 2007 in U.S. Appl. No. 10/633,329.
Office Action dated Jul. 30, 2007 in U.S. Appl. No. 10/633,329.
Office Action dated Feb. 4, 2008 in U.S. Appl. No. 10/633,329.
Office Action dated Jun. 12, 2008 in U.S. Appl. No. 10/633,329.
Office Action dated Dec. 18, 2008 in U.S. Appl. No. 10/633,329.
Office Action dated Jun. 11, 2009 in U.S. Appl. No. 10/633,329.
Office Action dated Jun. 23, 2009 in U.S. Appl. No. 10/648,849.
Office Action dated Jun. 24, 2008 n U.S. Appl. No. 11/007,920.
Office Action dated Jan. 27, 2006 in U.S. Appl. No. 11/007,635.
Office Action dated Nov. 28, 2007 in U.S. Appl. No. 10/991,966.
Office Action dated Jul. 22, 2008 in U.S. Appl. No. 10/991,966.
Office Action dated Nov. 27, 2006 in U.S. Appl. No. 10/789,359.
Office Action dated Mar. 20, 2008 in U.S. Appl. No. 10/789,359.
Office Action dated Oct. 3, 2008 in U.S. Appl. No. 10/789,359.
Office Action dated Jan. 15, 2008 in U.S. Appl. No. 11/034,344.
Office Action dated Nov. 1, 2007 in U.S. Appl. No. 11/034,343.
Office Action dated Jul. 10, 2008 in U.S. Appl. No. 11/034,343.
Office Action dated Dec. 30, 2008 in U.S. Appl. No. 11/034,343.
Office Action dated Sep. 21, 2007 in U.S. Appl. No. 10/838,912.
Office Action dated Mar. 24, 2008 in U.S. Appl. No. 10/838,912.
Office Action dated Jul. 16, 2008 in U.S. Appl. No. 10/838,912.
Office Action mailed Jun. 5, 2008 in U.S. Appl. No. 10/838,909.
Office Action mailed Mar. 16, 2009 in U.S. Appl. No. 10/838,909.
Office Action dated Dec. 24, 2008 in U.S. Appl. No. 10/885,476.
Office Action dated Jun. 23, 2009 in U.S. Appl. No. 10/885,476.
Office Action dated Mar. 31, 2008 in U.S. Appl. No. 11/077,759.
Office Action dated Jul. 10, 2008 in U.S. Appl. No. 11/077,759.
Office Action dated May 26, 2009 in U.S. Appl. No. 11/077,759.
Office Action dated Jul. 21, 2009 in U.S. Appl. No. 11/077,739.
Office Action dated Jun. 1, 2007 in U.S. Appl. No. 11/077,740.
Office Action dated Nov. 1, 2007 in U.S. Appl. No. 11/077,740.
Office Action dated Feb. 7, 2008 in U.S. Appl. No. 11/077,740.
Office Action dated Jul. 25, 2008 in U.S. Appl. No. 11/077,740.
Office Action dated Apr. 28, 2009 in U.S. Appl. No. 11/077,740.
Office Action dated Dec. 31, 2007 in U.S. Appl. No. 11/077,765.
Office Action dated May 16, 2008 in U.S. Appl. No. 11/077,765.
Office Action dated Sep. 19, 2008 in U.S. Appl. No. 11/077,765.
Office Action dated Jan. 23, 2009 in U.S. Appl. No. 11/077,765.
Office Action dated Jun. 26, 2008 in U.S. Appl. No. 11/157,365.
Office Action dated Jan. 7, 2009 in U.S. Appl. No. 11/157,365.
Office Action dated Jul. 21, 2009 in U.S. Appl. No. 11/157,365.
Office Action dated Oct. 4, 2006 in U.S. Appl. No. 11/334,876.
Office Action dated Sep. 25, 2007 in U.S. Appl. No. 11/334,876.
Office Action dated May 2, 2008 in U.S. Appl. No. 11/334,876.
Office Action dated Jun. 30, 2008 in U.S. Appl. No. 11/360,252.
Office Action dated Jan. 29, 2009, in U.S. Appl. No. 11/360,252.
Office Action dated Jul. 23, 2009 in U.S. Appl. No. 11/360,252.
Office Action dated Aug. 11, 2008 in U.S. Appl. No. 11/360,819.
Office Action dated Dec. 26, 2008 in U.S. Appl. No. 11/360,819.

Supplementary European Search Report for App. No. 04812899.5, dated May 29, 2008.

U.S. Appl. No. 09/447,227, filed Nov. 22, 1999.

Aalders et al. 1991. Development of a wearable glucose sensor; studies in healthy volunteers and in diabetic patients. The International Journal of Artificial Organs 14(2):102-108.

Abe et al. 1992. Characterization of glucose microsensors for intracellular measurements. Anal. Chem. 64(18):2160-2163.

Abel et al. 1984. Experience with an implantable glucose sensor as a prerequisite of an artificial beta cell, Biomed. Biochim. Acta 43(5):577-584.

Abel et al. 2002. Biosensors for in vivo glucose measurement: can we cross the experimental stage. Biosens Bioelectron 17:1059-1070.

Adilman, Glenn, Videogames: Knowing the Score, Creative Computing, V9, p. 224(5), Dec. 1983, Dialog: File 148, Acc# 01891055.

Alcock & Turner. 1994. Continuous Analyte Monitoring to Aid Clinical Practice. IEEE Engineering in Med. & Biol. Mag. 13:319-325.

American Heritage Dictionary, 4th Edition. 2000. Houghton Mifflin Company, p. 82.

Amin et al. 2003. Hypoglycemia prevalence in prepubertal children with type 1 diabetes on standard insulin regimen: Use of continuous glucose monitoring system. Diabetes Care 26(3):662-667.

Answers.com. "xenogenic." The American Heritage Stedman's Medical Dictionary. Houghton Mifflin Company, 2002. Answers. com Nov. 7, 2006 http://www. Answers.com/topic/xenogenic.

Atanasov et al. 1997. Implantation of a refillable glucose monitoring-telemetry device. Biosens Bioelectron 12:669-680.

Bailey et al. 2007. Reduction in hemoglobin A1c with real-time continuous glucose monitoring: results from a 12-week observational study. Diabetes Technology & Therapeutics 9(3):203-210.
Baker et al. 1993. Dynamic concentration challenges for biosensor characterization. Biosensors & Bioelectronics 8:433-441.
Baker et al. 1996. Dynamic delay and maximal dynamic error in continuous biosensors. Anal Chem 68(8):1292-1297.
Beach et al. 1999. Subminiature implantable potentiostat and modified commercial telemetry device for remote glucose monitoring. IEEE Transactions on Instrumentation and Measurement 48(6):1239-1245.
Bessman et al., Progress toward a glucose sensor for the artificial pancreas, Proceedings of a Workshop on Ion-Selective Microelectrodes, Jun. 4-5, 1973, Boston, MA, 189-197.
Biermann et al. 2008. How would patients behave if they were continually informed of their blood glucose levels? A simulation study using a "virtual" patient. Diab. Thechnol. & Therapeut., 10:178-187.
Bisenberger et al. 1995. A triple-step potential waveform at enzyme multisensors with thick-film gold electrodes for detection of glucose and sucrose. Sensors and Actuators, B 28:181-189.
Bland et al. 1990. A note on the use of the intraclass correlation coefficient in the evaluation of agreement between two methods of measurement. Comput. Biol. Med. 20(5):337-340.
Bode et al. 1999. Continuous glucose monitoring used to adjust diabetes therapy improves glycosylated hemoglobin: A pilot study. Diabetes Research and Clinical Practice 46:183-190.
Bode et al. 2000. Using the continuous glucose monitoring system to improve the management of type 1 diabetes. Diabetes Technology & Therapeutics, 2(Suppl 1):S43-48.
Bode, B. W. 2000. Clinical utility of the continuous glucose monitoring system. Diabetes Technol Ther, 2(Suppl 1):S35-41.
Boedeker Plastics, Inc. 2009. Polyethylene Specifications Data Sheet, http://www.boedeker.com/polye_p.htm [Aug. 19, 2009 3:36:33 PM].
Boland et al. 2001. Limitations of conventional methods of self-monitoring of blood glucose. Diabetes Care 24(11):1858-1862.
Bolinder et al. 1992. Microdialysis measurement of the absolute glucose concentration in subcutaneous adipose tissue allowing glucose monitoring in diabetic patients. Diabetologia 35:1177-1180.
Bolinder et al. 1997. Self-monitoring of blood glucose in type 1 diabetic patients: Comparison with continuous microdialysis measurements of glucose in subcutaneous adipose tissue during ordinary life conditions. Diabetes Care 20(1):64-70.
Bott, A. 1998. Electrochemical methods for the determination of glucose. Current Separations 17(1):25-31.
Bowman, L.; Meindl, J. D. 1986. The packaging of implantable integrated sensors. IEEE Trans Biomed Eng BME33(2):248-255.
Brauker et al. 1996. Local Inflammatory Response Around Diffusion Chambers Containing Xenografts Transplantation 61(12):1671-1677.
Braunwald, 2008. Biomarkers in heart failure. *N. Engl. J. Med.*, 358: 2148-2159.
Bremer et al. 1999. Is blood glucose predictable from previous values? A solicitation for data. Diabetes 48:445-451.
Bremer et al. 2001. Benchmark data from the literature for evaluation of new glucose sensing technologies. Diabetes Technology & Therapeutics 3(3):409-418.
Bruckel et al. 1989. In vivo measurement of subcutaneous glucose concentrations with an enzymatic glucose sensor and a wick method. Klin Wochenschr 67:491-495.
Brunstein et al. 1989. Preparation and validation of implantable electrodes for the measurement of oxygen and glucose. Biomed Biochim. Acta 48(11/12):911-917.
Cai et al. 2004. A wireless, remote query glucose biosensor based on a pH-sensitive polymer. Anal Chem 76(4):4038-4043.
Cameron et al. 1997. Micromodular Implants to provide electrical stimulation of paralyzed muscles and limbs. IEEE Transactions on Biomedical Engineering 44(9):781-790.
Campanella et al. 1993. Biosensor for direct determination of glucose and lactate in undiluted biological fluids. Biosensors & Bioelectronics 8:307-314.
Cassidy et al., Apr. 1993. Novel electrochemical device for the detection of cholesterol or glucose, Analyst, 118:415-418.

Chase et al. 2001. Continuous subcutaneous glucose monitoring in children with type 1 diabetes. Pediatrics 107:222-226.
Chen et al. 2006. A noninterference polypyrrole glucose biosensor. Biosensors and Bioelectronics 22:639-643.
Ciba® Irgacure® 2959 Photoinitiator, Product Description, Ciba Specialty Chemicals Inc., Basel, Switzerland, Apr. 2, 1998.
Claremont et al. 1986. Subcutaneous implantation of a ferrocene-mediated glucose sensor in pigs. Diabetologia 29:817-821.
Claremont et al. Jul. 1986. Potentially-implantable, ferrocene-mediated glucose sensor. J. Biomed. Eng. 8:272-274.
Clark et al. 1981. One-minute electrochemical enzymic assay for cholesterol in biological materials, Clin. Chem. 27(12):1978-1982.
Clark et al. 1987. Configurational cyclic voltammetry: increasing the specificity and reliablity of implanted electrodes, IEEE/Ninth Annual Conference of the Engineering in Medicine and Biology Society, pp. 0782-0783.
Clark et al. 1988. Long-term stability of electroenzymatic glucose sensors implanted in mice. Trans Am Soc Artif Intern Organs 34:259-265.
Clarke et al. Sep.-Oct. 1987. Evaluating Clinical Accuracy of Systems for Self-Monitoring of Blood Glucose. Diabetes Care 10(5):622-628.
CLSI. Performance metrics for continuous interstitial glucose monitoring; approved guideline, CLSI document POCT05-A. Wayne, PA: Clinical and Laboratory Standards Institute: 2008 28(33), 72 pp.
Colangelo et al. 1967. Corrosion rate measurements in vivo, Journal of Biomedical Materials Research, 1:405-414.
Colowick et al. 1976. Methods in Enzymlology, vol. XLIV, Immobilized Enzymes. New York: Academic Press. 11 pages.
Cox et al. 1985. Accuracy of perceiving blood glucose in IDDM. Diabetes Care 8(6):529-536.
Csöregi et al., 1994. Design, characterization, and one-point in vivo calibration of a subcutaneously implanted glucose electrode. Anal Chem. 66(19):3131-3138.
Currie et al., Novel non-intrusive trans-dermal remote wireless micro-fluidic monitoring systme applied to continuous glucose and lactate assays for casualty care and combat readiness assessment, RTO HFM Symposium, St. Pete Beach, RTO-MP-HFM-109, Aug. 16-18, 2004, 18 pp.
Danielsson et al. 1988. Enzyme thermistors, Methods in Enzymology, 137:181-197.
Dassau et al., In silico evaluation platform for artificial pancreatic β-cell development—a dynamic simulator for closed loop control with hardware-in-the-loop, Diabetes Technology & Therapeutics, 11(3):1-8, 2009.
Davis et al. 1983. Bioelectrochemical fuel cell and sensor based on a quinoprotein, alcohol dehydrogenase. *Enzyme Microb. Technol.*, vol. 5, September, 383-388.
Deutsch et al., "Time series analysis and control of blood glucose levels in diabetic patients". Computer Methods and Programs in Biomedicine 41 (1994) 167-182.
Diabetes Educational Video Game Recognized by Software Publishers Association, Press Release, Novo Nordisk, Mar. 14, 1994.
Direct 30/30® Blood Glucose Sensor, (Markwell Medical) Catalog, © 1990, ELCO Diagnostics Company. 1 page.
Dixon et al. 2002. Characterization in vitro and in vivo of the oxygen dependence of an enzyme/polymer biosensor for monitoring brain glucose. Journal of Neuroscience Methods 119:135-142.
DuPont[1] Dimension AR®. 1998. The chemistry analyzer that makes the most of your time, money and effort. Catalog. Dade International, Chemistry Systems. Newark, DE. 18 pages.
Durliat et al. 1976. Spectrophotometric and electrochemical determinations of L(+)-lactate in blood by use of lactate dehydrogenase from yeast, Clin. Chem. 22(11):1802-1805.
Edwards Lifesciences. Accuracy for your and your patients. Marketing materials, 4 pp. 2002.
El Degheidy et al. 1986. Optimization of an implantable coated wire glucose sensor. J. Biomed Eng. 8: 121-129.
El-Sa'ad et al. 1990. Moisture Absorption by Epoxy Resins: the Reverse Thermal Effect. Journal of Materials Science 25:3577-3582.
Fahy et al., An analysis: hyperglycemic intensive care patients need continuous glucose monitoring—easier said than done, Journal of Diabetese Science and Technology, 2(2):201-204, Mar. 2008.

Fischer et al. 1987. Assessment of subcutaneous glucose concentration: validation of the wick technique as a reference for implanted electrochemical sensors in normal and diabetic dogs, Diabetologia 30:940-945.

Fischer et al. 1989. Oxygen Tension at the Subcutaneous Implantation Site of Glucose Sensors. Biomed. Biochem 11/12:965-972.

Fischer et al. 1995. Abstract: Hypoglycemia-warning by means of subcutaneous electrochemical glucose sensors: an animal study, Horm. Metab. Rese. 27:53.

Freedman et al. 1991. Statistics, Second Edition, W.W. Norton & Company, p. 74.

Freiberger, Paul, Video Game Takes on Diabetes Superhero 'Captain Novolin' Offers Treatment Tips, San Francisco Examiner, Jun. 26, 1992, Fourth Edition, Business Sec. B1.

Frost et al. 2002. Implantable chemical sensors for real-time clinical monitoring: Progress and challenges. Current Opinion in Chemical Biology 6:633-641.

Gabbay et al. 2008. Optical coherence tomography-based continuous noninvasive glucose monitoring in patients with diabetes. Diab. Thechnol. & Therapeut., 10:188-193.

Ganesan et al., Gold layer-based dual crosslinking procedure of glucose oxidase with ferrocene monocarboxylic acid provides a stable biosensor, Analytical Biochemistry 343:188-191, 2005.

Ganesh et al., Evaluation of the VIA® blood chemistry monitor for glucose in healthy and diabetic volunteers, Journal of Diabetese Science and Technology, 2(2):182-193, Mar. 2008.

Gao et al. 1989. Determination of Interfacial parameters of cellulose acetate membrane materials by HPLC, *J. Liquid Chromatography*, VI. 12, n. 11, 2083-2092.

Garg et al. 1999. Correlation of fingerstick blood glucose measurements with GlucoWatch biographer glucose results in young subjects with type 1 diabetes. Diabetes Care 22(10):1708-1714.

Garg et al. 2004. Improved Glucose Excursions Using an Implantable Real-Time continuous Glucose Sensor in Adults with Type I Diabetes. Diabetes Care 27:734-738.

Geller et al. 1997. Use of an immunoisolation device for cell transplantation and tumor immunotherapy. Ann NY Acad Sci 831:438-451.

Gerritsen et al. 1999. Performance of subcutaneously implanted glucose sensors for continuous monitoring. The Netherlands Journal of Medicine 54:167-179.

Gerritsen, M. 2000. Problems associated with subcutaneously implanted glucose sensors. Diabetes Care 23(2):143-145.

Godsland et al. 2001. Maximizing the Success Rate of Minimal Model Insulin Sensitivity Measurement in Humans: The Importance of Basal Glucose Levels. The Biochemical Society and the Medical Research Society, 1-9.

Gough et al. 2000. Immobilized glucose oxidase in implantable glucose sensor technology. Diabetes Technology & Therapeutics 2(3):377-380.

Gough et al. 2003. Frequency characterization of blood glucose dynamics. Annals of Biomedical Engineering 31:91-97.

Gross et al. 2000. Efficacy and reliability of the continuous glucose monitoring system. Diabetes Technology & Therapeutics, 2(Suppl 1):S19-26.

Gross et al. 2000. Performance evaluation of the MiniMed® continuous glucose monitoring system during patient home use. Diabetes Technology & Therapeutics 2(1):49-56.

Hall et al. 1998. Electrochemical oxidation of hydrogen peroxide at platinum electrodes. Part I: An adsorption-controlled mechanism. Electrochimica Acta, 43(5-6):579-588.

Hall et al. 1998. Electrochemical oxidation of hydrogen peroxide at platinum electrodes. Part II: Effect of potential. Electrochimica Acta 43(14-15):2015-2024.

Hall et al. 1999. Electrochemical oxidation of hydrogen peroxide at platinum electrodes. Part III: Effect of temperature. Electrochimica Acta, 44:2455-2462.

Hall et al. 1999. Electrochemical oxidation of hydrogen peroxide at platinum electrodes. Part IV: Phosphate buffer dependence. Electrochimica Acta, 44:4573-4582.

Hall et al. 2000. Electrochemical oxidation of hydrogen peroxide at platinum electrodes. Part V: Inhibition by chloride. Electrochimica Acta, 45:3573-3579.

Hamilton Syringe Selection Guide. 2006. Syringe Selection. www.hamiltoncompany.com.

Hashiguchi et al. (1994). "Development of a miniaturized glucose monitoring system by combining a needle-type glucose sensor with microdialysis sampling method: Long-term subcutaneous tissue glucose monitoring in ambulatory diabetic patients," *Diabetes Care*, 17(5): 387-396.

Heise et al. 2003. Hypoglycemia warning signal and glucose sensors: Requirements and concepts. Diabetes Technology & Therapeutics 5:563-571.

Heller, A. 1999. Implanted electrochemical glucose sensors for the management of diabetes. Annu Rev Biomed Eng 1:153-175.

Heller, A. 2003. Plugging metal connectors into enzymes. Nat Biotechnol 21:631-2.

Hitchman, M. L. 1978. Measurement of Dissolved Oxygen. In Elving et al. (Eds.). Chemical Analysis, vol. 49, Chap. 3, pp. 34-49, 59-123. New York: John Wiley & Sons.

Hoel, Paul G. 1976. Elementary Statistics, Fourth Edition. John Wiley & Sons, Inc.. pp. 113-114.

Hrapovic et al. 2003. Picoamperometric detection of glucose at ultrasmall platinum-based biosensors: preparation and characterization. Anal Chem 75:3308-3315.

http://www.merriam-webster.com/dictionary, definition for "aberrant," Aug. 19, 2008, p. 1.

Hu, et al. 1993. A needle-type enzyme-based lactate sensor for in vivo monitoring, Analytica Chimica Acta, 281:503-511.

Huang et al. Aug. 1975. Electrochemical Generation of Oxygen. 1: The Effects of Anions and Cations on Hydrogen Chemisorption and Aniodic Oxide Film Formation on Platinum Electrode. 2: The Effects of Anions and Cations on Oxygen Generation on Platinum Electrode, pp. 1-116.

Huang et al., Sep. 1997, A 0.5mW Passive Telemetry IC for Biomedical Applications, Proceedings of the 23rd European Solid-State Circuits Conference (ESSCIRC '97), pp. 172-175, Southampton, UK.

Ishikawa et al. 1998. Initial evaluation of a 290-mm diameter subcutaneous glucose sensor: Glucose monitoring with a biocompatible, flexible-wire, enzyme-based amperometric microsensor in diabetic and nondiabetic humans. Journal of Diabetes and Its Complications, 12:295-301.

Jablecki et al. 2000. Simulations of the frequency response of implantable glucose sensors. Analytical Chemistry 72:1853-1859.

Jaffari et al. 1995. Recent advances in amperometric glucose biosensors for in vivo monitoring, Physiol. Meas. 16: 1-15.

Jaremko et al. 1998. Advances toward the implantable artificial pancreas for treatment of diabetes. Diabetes Care 21(3):444-450.

Jensen et al. 1997. Fast wave forms for pulsed electrochemical detection of glucose by incorporation of reductive desorption of oxidation products. Analytical Chemistry 69(9):1776-1781.

Jeutter, D. C. 1982. A transcutaneous implanted battery recharging and biotelemeter power switching system. IEEE Trans Biomed Eng 29:314-321.

Jeutter et al. 1993. Design of a radio-linked implantable cochlear prosthesis using surface acoustic wave devices. IEEE Transactions on ultrasonics, ferroelectrics and frequency control 40(5):469-477.

Jobst et al., Thin-Film Microbiosensors for Glucose-Lactate Monitoring, Anal Chem. (1996) 68(18): 3173-3179.

Johnson (1991). "Reproducible electrodeposition of biomolecules for the fabrication of miniature electroenzymatic biosensors," *Sensors and Actuators B*, 5:85-89.

Joung et al. 1998. An energy transmission system for an artificial heart using leakage inductance compensation of transcutaneous transformer. IEEE Transactions on Power Electronics 13(6):1013-1022.

Jovanovic, L. 2000. The role of continuous glucose monitoring in gestational diabetes mellitus. Diabetes Technology & Therapeutics, 2 Suppl 1, S67-71.

Kacaniklic May-Jun. 1994. Electroanalysis, 6(5-6):381-390.

Kang et al. 2003. In vitro and short-term in vivo characteristics of a Kel-F thin film modified glucose sensor. Anal Sci 19:1481-1486.

Kaufman et al. 2001. A pilot study of the continuous glucose monitoring system. Diabetes Care 24(12):2030-2034.

Kaufman. 2000. Role of the continuous glucose monitoring system in pediatric patients. Diabetes Technology & Therapeutics 2(1):S-49-S-52.

Keedy et al. 1991. Determination of urate in undiluted whole blood by enzyme electrode. *Biosensors & Bioelectronics*, 6: 491-499.

Kerner et al. 1988. A potentially implantable enzyme electrode for amperometric measurement of glucose, Horm Metab Res Suppl. 20:8-13.

Koschinsky et al. 2001. Sensors for glucose monitoring: Technical and clinical aspects. Diabetes Metab. Res. Rev. 17: 113-123.

Kost et al. 1985. Glucose-sensitive membranes containing glucose oxidase: activitiy, swelling, and permeability studies, Journal of Biomedical Materials Research 19:1117-1133.

Koudelka et al. 1989. In vivo response of microfabricated glucose sensors to glycemia changes in normal rats. Biomed Biochim Acta 48(11-12):953-956.

Koudelka et al. 1991. In-vivo behaviour of hypodermically implanted microfabricated glucose sensors. Biosensors & Bioelectronics 6:31-36.

Kovatchev et al. Aug. 2004. Evaluating the accuracy of continuous glucose-monitoring sensors: continuous glucose-error grid analysis illustrated by TheraSense Freestyle Navigator data. Diabetes Care 27(8):1922-1928.

Kraver et al. 2001. A mixed-signal sensor interface microinstrument. Sensors and Actuators A 91:266-277.

Krouwer, J. S. 2002. Setting performance goals and evaluating total analytical error for diagnostic assays. Clinical Chemistry 48(6):919-927.

Kruger et al. 2000. Psychological motivation and patient education: A role for continuous glucose monitoring. Diabetes Technology & Therapeutics, 2(Suppl 1):S93-97.

Kulys et al., 1994. Carbon-paste biosensors array for long-term glucose measurement, Biosensors& Beioelectronics, 9:491-500.

Kunjan et al., Automated blood sampling and glocuse sensing in critical care settings, Journal of Diabetes Science and Technology 2(3):194-200, Mar. 2008.

Kurtz et al. 2005. Recommendations for blood pressure measurement in humans and experimental animals, Part 2: Blood pressure measurement in experimental animals, A statement for professionals from the subcommittee of professional and public education of the American Heart Association Council on High Blood Pressure Research. Hypertension 45:299-310.

LaCourse et al. 1993. Optimization of waveforms for pulsed amperometric detection of carbohydrates based on pulsed voltammetry. Analytical Chemistry 65:50-52.

Ladd et al., Structure Determination by X-ray Crystallography, 3rd ed. Plenum, 1996, Ch. 1, pp. xxi-xxiv and 1-58.

Lee et al. 1999. Effects of pore size, void volume, and pore connectivity on tissue responses. Society for Biomaterials 25th Annual Meeting, 171.

Lehmann et al. May 1994. Retrospective valication of a physiological model of glucose-iunsulin interaaction in tyhpe 1 diabetes mellitus, Med. Eng. Phys. 16:193-202.

Lerner et al. 1984. An implantable electrochemical glucose sensor. Ann. N.Y. Acad. Sci. 428:263-278.

Lewandowski et al. 1988. Evaluation of a miniature blood glucose sensor. Trans Am Soc Artif Intern Organs 34:255-258.

Leypoldt et al. 1984. Model of a two-substrate enzyme electrode for glucose. Anal. Chem. 56:2896-2904.

Linke et al. 1994. Amperometric biosensor for in vivo glucose sensing based on glucose oxidase immobilized in a redox hydrogel. Biosensors & Bioelectronics 9:151-158.

Lowe, 1984. Biosensors, Trends in Biotechnology, 2(3):59-65.

Luong et al. 2004. Solubilization of Multiwall Carbon Nanotubes by 3-Aminopropyltriethoxysilane Towards the Fabrication of Electrochemical Biosensors with Promoted Electron Transfer. Electronanalysis 16(1-2):132-139.

Lynch et al. 2001. Estimation-based model predictive control of blood glucose in type I diabetics: A simulation study. Proceedings of the IEEE 27th Annual Northeast Bioengineering Conference, pp. 79-80.

Lynn, P. A. 1971. Recursive digital filters for biological signals. Med. & Biol. Engng. 9:37-43.

Makale et al. 2003. Tissue window chamber system for validation of implanted oxygen sensors. Am. J. Physiol. Heart Circ. Physiol. 284:H2288-2294.

Malin et al. 1999. Noninvasive Prediction of Glucose by Near-Infrared Diffuse Reflectance Spectroscopy. Clinical Chemistry 45:9, 1651-1658.

Mancy et al. 1962. A galvanic cell oxygen analyzer. Journal of Electroanalytical Chemistry 4:65-92.

Maran et al. 2002. Continuous subcutaneous glucose monitoring in diabetic patients: A multicenter analysis. Diabetes Care 25(2):347-352.

March, W. F. 2002. Dealing with the delay. Diabetes Technol Ther 4(1):49-50.

Marena et al. 1993. The artifical endocrine pancreas in clinical practice and research. Panminerva Medica 35(2):67-74.

Martin, R. F. 2000. General Deming regression for estimating systematic bias and its confidence interval in method-comparison studies. *Clinical Chemistry*, 46(1):100-104.

Mascini et al. 1989. Glucose electrochemical probe with extended linearity for whole blood. *J Pharm Biomed Anal* 7(12): 1507-1512.

Mastrototaro et al. 2003. Reproducibility of the continuous glucose monitoring system matches previous reports and the intended use of the product. Diabetes Care 26:256; author reply p. 257.

Mastrototaro, J. J. 2000. The MiniMed continuous glucose monitoring system. Diabetes Technol Ther 2(Suppl 1):S13-8.

Matsuki. 1994. Energy transfer system utilizing amorphous wires for implantable medical devices. IEEE Transactions on Magnetics 31(2):1276-1282.

Matthews et al. 1988. An amperometric needle-type glucose sensor testing in rats and man. Diabetic Medicine 5:248-252.

Mazze et al. 2008. Characterizing glucose exposure for individuals with normal glucose tolerance using continuous glucose monitoring and ambulatory glucose profile analysis. Diab. Thechnol. & Therapeut., 10:149-159.

Mazzola et al., Video Diabetes: A Teaching Tool for Children with Insulin-Dependent Diabetes, Proceedings—7th Annual Symposium on Computer Applications in Medical Care; Washington, D.C.; Dialog:, (Oct. 1983), File 8, Acc# 01624462.

McCartney et al. 2001. Near-infrared fluorescence lifetime assay for serum glucose based on allophycocyanin-labeled concanavalin A. Anal Biochem 292:216-221.

Merriam-Webster Online Dictionary. Definition of "acceleration". http://www.merriam-webster.com/dictionary/Acceleration Jan. 11, 2010.

Merriam-Webster Online Dictionary. Definition of "nominal". http://www.merriam-webster.com/dictionary/nominal Apr. 23, 2007.

Merriam-Webster Online Dictionary. Definition of "system". http://www.merriam-webster.com/dictionary/System Jan. 11, 2010.

Metzger et al. Jul. 2002. Reproducibility of glucose measurements using the glucose sensor. Diabetes Care 25(6):1185-1191.

Meyerhoff et al. 1992. On line continuous monitoring of subcutaneous tissue glucose in men by combining portable glucosensor with microdialysis. Diabetologia 35:1087-1092.

Miller et al. 1993. Development of an autotuned transcutaneous energy transfer system ASAIO Journal 39:M706-M710.

Moatti-Sirat et al. Jun. 1994. Reduction of acetaminophen interference in glucose sensors by a composite Nafion membrane: demonstration in rats and man, Diabetologia 37(6):610-616.

Monsod et al. 2002. Do sensor glucose levels accurately predict plasma glucose concentrations during hypoglycemia and hyperinsulinemia? Diabetes Care 25(5):889-893.

Morff et al. 1990. Microfabrication of reproducible, economical, electroenzymatic glucose sensors, Annual International Conference of the IEEE Engineering in Medicine and Biology Society, 12(2):0483-0484.

Mosbach et al. 1975. Determination of heat changes in the proximity of immobilized enzymes with an enzyme thermistor and its use for the assay of metabolites, Biochim. Biophys. Acta. 403:256-265.

Motonaka et al. 1993. Determination of cholesterol and cholesterol ester with novel enzyme microsensors, Anal. Chem. 65:3258-3261.

Moussy et al. 1993. Performance of subcutaneously implanted needle-type glucose sensors employing a novel trilayer coating, Anal Chem. 85: 2072-2077.

Moussy, Francis (Nov. 2002) Implantable Glucose Sensor: Progress and Problems, Sensors, 1:270-273.

Muslu. 1991. Trickling filter performance. Apllied Biochemistry and Biotechnology 37:211-224.

Neuburger et al. 1987. Pulsed amperometric detection of carbohydrates at gold electrodes with a two-step potential waveform. Anal. Chem. 59:150-154.

Nintendo Healthcare, Wired, Dec. 1993.

Okuda et al. 1971. Mutarotase effect on micro determinations of D-glucose and its anomers with β-D-glucose oxidase. Anal Biochem 43:312-315.

Oxford English Dictionary Online. Jan. 11, 2010. Definition of "impending". http://www.askoxford.com/results/?view=dev dict &field-12668446 Impending&branch=.

Panteleon et al. 2003. The role of the independent variable to glucose sensor calibration. Diabetes Technology & Therapeutics 5(3):401-410.

Parker et al. 1999. A model-based algorithm for blood glucose control in type I diabetic patients. IEEE Trans. Biomed. Eng. 46(2):148-157.

Patel et al. 2003. Amperometric glucose sensors based on ferrocene containing polymeric electron transfer systems—a preliminary report. Biosens Bioelectron 18:1073-6.

Peacock et al. 2008. Cardiac troponin and outcome in acute heart failure. N. Engl. J. Med., 358: 2117-2126.

Pfeiffer, E.F. 1990. The glucose sensor: the missing link in diabetes therapy, Horm Metab Res Suppl. 24:154-164.

Pfeiffer et al. 1992. On line continuous monitoring of subcutaneous tissue glucose is feasible by combining portable glucosensor with microdialysis. Horm. Metab. Res. 25:121-124.

Phillips. 1995. A high capacity transcutaneous energy transmission system. ASAIO Journal 41:M259-M262.

Pichert et al. 2000. Issues for the coming age of continuous glucose monitoring Diabetes Educ 26(6):969-980.

Pickup et al. 1989. Potentially-implantable, amperometric glucose sensors with mediated electron transfer: improving the operating stability. Biosensors 4:109-119.

Pickup et al. 1993. Responses and Calibration of Amperometric Glucose Sensors Implanted in the Subcutaneous Tissue of Man. ACTA Diabetol, pp. 143-148.

Pinner et al., Cross-linking of cellulose acetate by ionizing radiation, Nature, vol. 184, 1303-1304, Oct. 24, 1959.

Pitzer et al. 2001. Detection of hypoglycemia with the GlucoWatch biographer. Diabetes Care 24(5):881-885.

Poirier et al. 1998. Clinical and statistical evaluation of self-monitoring blood glucose meters. Diabetes Care 21(11):1919-1924.

Poitout et al. 1994. Development of a glucose sensor for glucose monitoring in man: the disposable implant concept. Clinical Materials 15:241-246.

Quinn et al. 1995. Kinetics of glucose delivery to subcutaneous tissue in rats measured with 0.3-mm amperometric microsensors. The American Physiological Society E155-E161.

Quinn et al. 1997. Biocompatible, glucose-permeable hydrogel for in situ coating of implantable biosensors. Biomaterials 18:1665-1670.

Rabah et al., 1991. Electrochemical wear of graphite anodes during electrolysis of brine, Carbon, 29(2):165-171.

Raya Systems Pioneers Healthy Video Games, PlayRight, Nov. 1993 (pp. 14-15).

Reach et al. 1986. A Method for Evaluating in vivo the Functional Characteristics of Glucose Sensors. Biosensors 2:211-220.

Reach, G. 2001. Which threshold to detect hypoglycemia? Value of receiver-operator curve analysis to find a compromise between sensitivity and specificity. Diabetes Care 24(5):803-804.

Reach, Gerard. 2001. Letters to the Editor Re: Diabetes Technology & Therapeutics, 2000;2:49-56. Diabetes Technology & Therapeutics 3(1):129-130.

Rebrin et al. 1992. Subcutaenous glucose monitoring by means of electrochemical sensors: fiction or reality? J. Biomed. Eng. 14:33-40.

Rebrin et al. 1999. Subcutaneous glucose predicts plasma glucose independent of insulin: Implications for continuous monitoring. Am. J. Physiol. 277:E561-71.

Reusch. 2004. Chemical Reactivity. Organometallic Compounds. Virtual Textbook of Organic Chem. pp. 1-16, http://www.cem.msu.edu/~reusch/VirtualText/orgmetal.htm.

Rigla et al. 2008. Real-time continuous glucose monitoring together with telemedical assitance improves glycemic control and glucose stability in pump-treated patients. Diab. Thechnol. & Therapeut., 10:194-199.

Rivers et al., Central venous oxygen saturation monitoring in the critically ill patient, Current Opinion in Critical Care, 7:204-211, 2001.

Sakakida et al. 1992. Development of Ferrocene-Mediated Needle-Type Glucose Sensor as a Measure of True Subcutaneous Tissue Glucose Concentrations. Artif. Organs Today 2(2):145-158.

Sakakida et al. 1993. Ferrocene-Mediated Needle Type Glucose Sensor Covered with Newly Designed Biocompatible Membran, Sensors and Actuators B 13-14:319-322.

Salardi et al. 2002. The glucose area under the profiles obtained with continuous glucose monitoring system relationships with HbA1c in pediatric type 1 diabetic patients. Diabetes Care 25(10):1840-1844.

San Diego Plastics, Inc. 2009. Polyethylene Data Sheet, http://www.sdplastics.com/polyeth.html.

Sansen et al. 1985. "Glucose sensor with telemetry system." In Ko, W. H. (Ed.). Implantable Sensors for Closed Loop Prosthetic Systems. Chap. 12, pp. 167-175, Mount Kisco, NY: Futura Publishing Co.

Sansen et al. 1990. A smart sensor for the voltammetric measurement of oxygen or glucose concentrations. Sensors and Actuators B 1:298-302.

Schmidt et al. 1992. Calibration of a wearable glucose sensor. The International Journal of Artificial Organs 15(1):55-61.

Schmidt et al. 1993. Glucose concentration in subcutaneous extracellular space. Diabetes Care 16(5):695-700.

Schmidtke et al. 1998. Accuracy of the one-point in vivo calibration of "wired" glucose oxidase electrodes implanted in jugular veins of rats in periods of rapid rise and decline of the glucose concentration. Anal Chem 70(10):2149-2155.

Schmidtke et al., Measurement and modeling of the transient difference between blood and subcutaneous glucose concentrations in the rat after injection of insulin. *Proc Natl Aced Sci U S A* 1998, 95, 294-299.

Schoemaker et al. 2003. The SCGM1 system: Subcutaneous continuous glucose monitoring based on microdialysis technique. Diabetes Technology & Therapeutics 5(4):599-608.

Schoonen et al. 1990. Development of a potentially wearable glucose sensor for patients with diabetes mellitus: design and in-vitro evaluation. Biosensors & Bioelectronics 5:37-46.

Service et al. 1987. Measurements of glucose control. Diabetes Care, 10: 225-237.

Service, R. F. 2002. Can sensors make a home in the body? Science 297:962-3.

Sharkawy et al. 1996. Engineering the tissue which encapsulates subcutaneous implants. I. Diffusion properties, J Biomed Mater Res, 37:401-412.

Shichiri et al. 1982. Wearable artificial endocrine pancrease with needle-type glucose sensor. Lancet 2:1129-1131.

Shichiri et al. 1983. Glycaemic Control in Pancreatectomized Dogs with a Wearable Artificial Endocrine Pancreas. Diabetologia 24:179-184.

Skyler, J. S. 2000. The economic burden of diabetes and the benefits of improved glycemic control: The potential role of a continuous glucose monitoring system. Diabetes Technology & Therapeutics 2 Suppl 1:S7-12.

Slater-Maclean et al. 2008. Accuracy of glycemic measurements in the critically ill. Diab. Thechnol. & Therapeut., 10:169-177.

Smith et al. 1998. An externally powered, multichannel, implantable stimulator-telemeter for control of paralyzed muscle. IEEE Transactions on Biomedical Engineering 45(4):463-475.

Sokolov et al. 1995. Metrological opportunities of the dynamic mode of operating an enzyme amperometric biosensor. Med. Eng. Phys. 17(6):471-476.

Sparacino et al., 2008. Continuous glucose monitoring time series and hypo/hyperglycemia prevention: requirements, methods, open problems, Current Diabetes Reviews, 4:181-192.

Sproule et al. 2002. Fuzzy pharmacology: Theory and applications. Trends in Pharmacological Sciences, 23(9):412-417.

Sriyudthsak et al. 1996. Enzyme-epoxy membrane based glucose analyzing system and medical applications. Biosens Bioelectron 11:735-742.

Steil et al. 2003. Determination of plasma glucose during rapid glucose excursions with a subcutaneous glucose sensor. Diabetes Technology & Therapeutics 5(1):27-31.

Stern et al., 1957. Electrochemical polarization: 1. A theoretical analysis of the shape of polarization curves, Journal of the Electrochemical Society, 104(1):56-63.

Street et al. 1988. A note on computing robust regression estimates via iteratively reweighted least squares. The American Statistician 42(2):152-154.

Sumino T. et al. 1998. Preliminary study of continuous glucose monitoring with a microdialysis technique. Proceedings of the IEEE, 20(4):1775-1778.

Takegami et al. 1992. Pervaporation of ethanol water mixtures using novel hydrophobic membranes containing polydimethylsiloxane, Journal of Membrane Science, 75: 93-105.

Tamura, T. et al. 2000. Preliminary study of continuous glucose monitoring with a microdialysis technique and a null method—a numerical analysis. Frontiers Med. Biol. Engng. 10(2):147-156.

Tanenberg et al. 2000. Continuous glucose monitoring system: A new approach to the diagnosis of diabetic gastroparesis. Diabetes Technology & Therapeutics, 2 Suppl 1:S73-80.

Tatsuma et al. 1991. Oxidase/peroxidase bilayer-modified electrodes as sensors for lactate, pyruvate, cholesteral and uric acid, Analytica Chimica Acta, 242:85-89.

Thome et al. 1995. Abstract: Can the decrease in subcutaneous glucose concentration precede the decrease in blood glucose level? Proposition for a push-pull kinetics hypothesis, Horm. Metab. Res. 27:53.

Thomé-Duret et al. 1996. Modification of the sensitivity of glucose sensor implanted into subcutaneous tissue. Diabetes Metabolism, 22:174-178.

Thome-Duret et al. 1996. Use of a subcutaneous glucose sensor to detect decreases in glucose concentration prior to observation in blood, Anal. Chem. 68:3822-3826.

Thomé-Duret et al. 1998. Continuous glucose monitoring in the free-moving rat. Metabolism, 47:799-803.

Thompson et al., In Vivo Probes: Problems and Perspectives, Department of Chemistry, University of Toronto, Canada, pp. 255-261, 1986.

Tierney et al. 2000. The GlucoWatch® biographer: A frequent, automatic and noninvasive glucose monitor. Ann. Med. 32:632-641.

Tilbury et al. 2000. Receiver operating characteristic analysis for intelligent medical systems—A new approach for finding confidence intervals. IEEE Transactions on Biomedical Engineering 47(7):952-963.

Torjman et al., Glucose monitoring in acute care: technologies on the horizon, Journal of Deabetes Science and Technology, 2(2):178-181, Mar. 2008.

Trajanoski et al. 1998. Neural predictive controller for insulin delivery using the subcutaneous route. IEEE Transactions on Biomedical Engineering 45(9):1122-1134.

Trecroci, D. 2002. A Glimpse into the Future—Continuous Monitoring of Glucose with a Microfiber. Diabetes Interview 42-43.

Tse and Gough. 1987. Time-Dependent Inactivation of Immobilized Glucose Oxidase and Catalase. Biotechnol. Bioeng. 29:705-713.

Turner et al. 1984. Carbon Monoxide: Acceptor Oxidoreductase from Pseudomonas Thermocarboxydovorans Strain C2 and its use in a Carbon Monoxide Sensor. Analytica Chimica Acta, 163: 161-174.

Unger et al. 2004. Glucose control in the hospitalized patient. Emerg Med 36(9):12-18.

Updike et al. 2000. A subcutaneous glucose sensor with improved longevity, dynamic range, and stability of calibration. Diabetes Care 23(2):208-214.

Utah Medical Products Inc., Blood Pressure Transducers product specifications. 6 pp. 2003-2006, 2003.

Vadgama, P. Nov. 1981. Enzyme electrodes as practical biosensors. Journal of Medical Engineering & Technology 5(6):293-298.

Vadgama. 1988. Diffusion limited enzyme electrodes. NATO ASI Series: Series C, Math and Phys. Sci. 226:359-377.

Valdes et al. 2000. In vitro and in vivo degradation of glucose oxidase enzyme used for an implantable glucose biosensor. Diabetes Technol. Ther. 2:367-376.

Van den Berghe 2004. Tight blood glucose control with insulin in "real-life" intensive care. Mayo Clin Proc 79(8):977-978.

Velho et al. 1989. In vitro and in vivo stability of electrode potentials in needle-type glucose sensors. Influence of needle material. Diabetes 38:164-171.

Wang et al. 1994. Highly Selective Membrane-Free, Mediator-Free Glucose Biosensor. Anal. Chem. 66:3600-3603.

Wang et al. 1997. Improved ruggedness for membrane-based amperometric sensors using a pulsed amperometric method. Anal Chem 69:4482-4489.

Ward et al. 2002. A new amperometric glucose microsensor: In vitro and short-term in vivo evaluation. Biosensors & Bioelectronics, 17:181-189.

Ward et al. 2004. A wire-based dual-analyte sensor for Glucose and Lactate: In Vitro and In Vivo Evaluation, Diab Tech Therapeut. 6(3): 389-401.

Wientjes, K. J. C. 2000. Development of a glucose sensor for diabetic patients (Ph.D. Thesis).

Wikipedia 2006. "Intravenous therapy," http://en.wikipedia.org/wiki/Intravenous_therapy, Aug. 15, 2006, 6 pp.

Wiley Electrical and Electronics Engineering Dictionary. 2004. John Wiley & Sons, Inc. pp. 141, 142, 548, 549.

Wilkins et al. 1988. The coated wire electrode glucose sensor, Horm Metab Res Suppl., 20:50-55.

Wilson et al. 2000. Enzyme-based biosensors for in vivo measurements. Chem. Rev., 100:2693-2704.

Wood, W. et al. Mar. 1990. Hermetic Sealing with Epoxy. Mechanical Engineering 1-3.

Woodward. 1982. How Fibroblasts and Giant Cells Encapsulate Implants: Considerations in Design of Glucose Sensor. Diabetes Care 5:278-281.

Worsley et al., Measurement of glucose in blood with a phenylboronic acid optical sensor, Journal of Diabetes Science and Technology, 2(2):213-220, Mar. 2008.

Wright et al., Bioelectrochemical dehalogenations via direct electrochemistry of poly(ethylene oxide)-modified myoglobin, Electrochemistry Communications 1 (1999) 603-611.

Wu et al. 1999. In situ electrochemical oxygen generation with an immunoisolation device. Annals New York Academy of Sciences, pp. 105-125.

Yamasaki et al. 1989. Direct measurement of whole blood glucose by a needle-type sensor. Clinica Chimica Acta. 93:93-98.

Yamasaki, Yoshimitsu. Sep. 1984. The development of a needle-type glucose sensor for wearable artificial endocrine pancreas. Medical Journal of Osaka University 35(1-2):25-34.

Yang et al. 1998. Development of needle-type glucose sensor with high selectivity. Science and Actuators B 46:249-256.

Yang, et al. 2004. A Comparison of Physical Properties and Fuel Cell Performance of Nafion and Zirconium Phosphate/Nafion Composite Membranes. Journal Of Membrane Science 237:145-161.

Ye et al. 1993. High Current Density 'Wired' Quinoprotein Glucose Dehydrogenase Electrode. Anal. Chem. 65:238-241.

Zamzow et al. 1990. Development and evaluation of a wearable blood glucose monitor, ASAIO Transactions; 36(3): pp. M588-M591.

Zavalkoff et al. 2002. Evaluation of conventional blood glucose monitoring as an indicator of integrated glucose values using a continuous subcutaneous sensor. Diabetes Care 25(9):1603-1606.

Zethelius et al. 2008. Use of multiple biomarkers to improve the prediction of death from cardiovascular causes. N. Engl. J. Med., 358: 2107-2116.

Zhang et al (1993). Electrochemical oxidation of $H_2O_2$ on Pt and Pt + Ir electrodes in physiological buffer and its applicability to $H_2O_2$-based biosensors. *J. Electroanal. Chem.*, 345:253-271.

Zhang et al. 1993. In vitro and in vivo evaluation of oxygen effects on a glucose oxidase based implantable glucose sensor. Analytica Chimica Acta, 281:513-520.

Zhu et al. (1994). "Fabrication and characterization of glucose sensors based on a microarray H$_2$O$_2$ electrode." *Biosensors & Bioelectronics*, 9: 295-300.

Ziaie et al. 1997. A single-channel implantable microstimulator for functional neuromuscular stimulation. IEEE Transactions on Biomedical Engineering 44(10):909-920.

EPO Communication dated May 5, 2009 in Application No. 04812899.5, filed Dec. 3, 2004.

EPO Communication dated Oct. 13, 2010 in EP Application No. 10168369.6 filed Dec. 3, 2004.

EPO Communication dated Oct. 14, 2010 in EP Application No. 10168368.8 filed Dec. 3, 2004.

EPO Communication dated Oct. 14, 2010 in EP Application No. 10168371.2 filed Dec. 3, 2004.

EPO communication dated Oct. 8, 2010 in EP Application No. 07853741.2 filed Oct. 2, 2007.

EPO Notice of Opposition dated May 11, 2011 by Abbott Diabetes Care, Inc. against EP Patent No. 1711790, issued Oct. 18, 2006.

ISR and WO dated Aug. 8, 2008 for PCT/US2007/007612, filed Mar. 27, 2007.

IPRP dated Oct. 23, 2008 for PCT/US2007/007612, filed Mar. 27, 2007.

Electronic File History of U.S. Appl. No. 12/619,502, filed Nov. 16, 2009 (now U.S. Patent No. 7,917,186, issued Mar. 29, 2011) containing Office Action(s) mailed Sep. 7, 2010, Dec. 8, 2010 and Jan. 26, 2011 and Applicant Response(s) filed Nov. 16, 2010, Jan. 11, 2011 and Feb. 2, 2011.

Electronic File History of Reexamination Control No. 90/011671, filed May 5, 2011 containing Office Action(s) mailed May 13, 2011 and 3$^{rd}$ Party submissions dated May 5, 2011 as of Jun. 3, 2011.

US 7,530,950, 05/2009, Brister et al. (withdrawn)

\* cited by examiner

CALIBRATION TECHNIQUES FOR A CONTINUOUS ANALYTE SENSOR

RELATED APPLICATIONS

This application is a continuation of U.S. application Ser. No. 12/619,502 filed Nov. 16, 2009, which is a continuation of U.S. application Ser. No. 11/004,561 filed Dec. 3, 2004, now U.S. Pat. No. 7,715,893, which claims the benefit of U.S. Provisional Application No. 60/527,323 filed Dec. 5, 2003, U.S. Provisional Application No. 60/587,787 filed Jul. 13, 2004, and U.S. Provisional Application No. 60/614,683 filed Sep. 30, 2004, the disclosures of which are hereby expressly incorporated by reference in their entirety and are hereby expressly made a portion of this application.

FIELD OF THE INVENTION

The present invention relates generally to systems and methods for processing analyte sensor data.

BACKGROUND OF THE INVENTION

Diabetes mellitus is a disorder in which the pancreas cannot create sufficient insulin (Type I or insulin dependent) and/or in which insulin is not effective (Type 2 or non-insulin dependent). In the diabetic state, the victim suffers from high blood sugar, which may cause an array of physiological derangements (for example, kidney failure, skin ulcers, or bleeding into the vitreous of the eye) associated with the deterioration of small blood vessels. A hypoglycemic reaction (low blood sugar) may be induced by an inadvertent overdose of insulin, or after a normal dose of insulin or glucose-lowering agent accompanied by extraordinary exercise or insufficient food intake.

Conventionally, a diabetic person carries a self-monitoring blood glucose (SMBG) monitor, which typically comprises uncomfortable finger pricking methods. Due to the lack of comfort and convenience, a diabetic will normally only measure his or her glucose level two to four times per day. Unfortunately, these time intervals are so far spread apart that the diabetic will likely find out too late, sometimes incurring dangerous side effects, of a hyper- or hypo-glycemic condition. In fact, it is not only unlikely that a diabetic will take a timely SMBG value, but the diabetic will not know if their blood glucose value is going up (higher) or down (lower) based on conventional methods, inhibiting their ability to make educated insulin therapy decisions.

SUMMARY OF THE INVENTION

A variety of continuous glucose sensors have been developed for detecting and/or quantifying glucose concentration in a host. These sensors have typically required one or more blood glucose measurements, or the like, from which to calibrate the continuous glucose sensor to calculate the relationship between the current output of the sensor and blood glucose measurements, to provide meaningful values to a patient or doctor. Unfortunately, continuous glucose sensors are conventionally also sensitive to non-glucose related changes in the baseline current and sensitivity over time, for example, due to changes in a host's metabolism, maturation of the tissue at the biointerface of the sensor, interfering species which cause a measurable increase or decrease in the signal, or the like. Therefore, in addition to initial calibration, continuous glucose sensors should be responsive to baseline and/or sensitivity changes over time, which requires recalibration of the sensor. Consequently, users of continuous glucose sensors have typically been required to obtain numerous blood glucose measurements daily and/or weekly in order to maintain calibration of the sensor over time.

The preferred embodiments provide improved calibration techniques that utilize electrode systems and signal processing that provides measurements useful in simplifying and updating calibration that allows the patient increased convenience (for example, by requiring fewer reference glucose values) and confidence (for example, by increasing accuracy of the device).

One aspect of the present invention is a method for measuring a sensitivity change of a glucose sensor implanted in a host over a time period comprising: 1) measuring a first signal in the host by obtaining at least one glucose-related sensor data point, wherein the first signal is measured at a glucose-measuring electrode disposed beneath an enzymatic portion of a membrane system on the sensor; 2) measuring a second signal in the host by obtaining at least one non-glucose constant data point, wherein the second signal is measured beneath the membrane system on the sensor; and 3) monitoring the second signal over a time period, whereby a sensitivity change associated with solute transport through the membrane system is measured. In one embodiment, the second signal is indicative of a presence or absence of a water-soluble analyte. The water-soluble analyte may comprise urea. In one embodiment, the second signal is measured at an oxygen-measuring electrode disposed beneath a non-enzymatic portion of the membrane system. In one embodiment, the glucose-measuring electrode incrementally measures oxygen, whereby the second signal is measured. In one embodiment, the second signal is measured at an oxygen sensor disposed beneath the membrane system. In one embodiment, the sensitivity change is calculated as a glucose-to-oxygen ratio, whereby an oxygen threshold is determined that is indicative of a stability of the glucose sensor. One embodiment further comprises filtering the first signal responsive to the stability of the glucose sensor. One embodiment further comprises displaying a glucose value derived from the first signal, wherein the display is suspended depending on the stability of the glucose sensor. One embodiment further comprises calibrating the first signal, wherein the calibrating step is suspended when the glucose sensor is determined to be stable. One embodiment further comprises calibrating the glucose sensor when the sensitivity change exceeds a preselected value. The step of calibrating may comprise receiving a reference signal from a reference analyte monitor, the reference signal comprising at least one reference data point. The step of calibrating may comprise using the sensitivity change to calibrate the glucose sensor. The step of calibrating may be performed repeatedly at a frequency responsive to the sensitivity change. One embodiment further comprises determining a stability of glucose transport through the membrane system, wherein the stability of glucose transport is determined by measuring the sensitivity change over a time period. One embodiment further comprises a step of prohibiting calibration of the glucose sensor when glucose transport is determined to be unstable. One embodiment further comprises a step of filtering at least one glucose-related sensor data point when glucose transport is determined to be unstable.

Another aspect of the present invention is a system for measuring glucose in a host, comprising a glucose-measuring electrode configured to generate a first signal comprising at least one glucose-related sensor data point, wherein the glucose-measuring electrode is disposed beneath an enzymatic portion of a membrane system on a glucose sensor and a transport-measuring electrode configured to generate a second signal comprising at least one non-glucose constant analyte data point, wherein the transport-measuring electrode is situated beneath the membrane system on the glucose sensor. One embodiment further comprises a processor module configured to monitor the second signal whereby a sensitivity change associated with transport of the non-glucose constant analyte through the membrane system over a time period is measured. In one embodiment, the transport-measuring electrode is configured to measure oxygen. In one embodiment, the processor module is configured to determine whether a glucose-to-oxygen ratio exceeds a threshold level, wherein a value is calculated from the first signal and the second signal, wherein the value is indicative of the glucose-to-oxygen ratio. In one embodiment, the processor module is configured to calibrate the glucose-related sensor data point in response to the sensitivity change. In one embodiment, the processor module is configured to receive reference data from a reference analyte monitor, the reference data comprising at least one reference data point, wherein the processor module is configured to use the reference data point for calibrating the glucose-related sensor data point. In one embodiment, the processor module is configured to use the sensitivity change for calibrating the glucose-related sensor data point. In one embodiment, the processor module is configured to calibrate the glucose-related sensor data point repeatedly at a frequency, wherein the frequency is selected based on the sensitivity change. One embodiment further comprises a stability module configured to determine a stability of glucose transport through the membrane system, wherein the stability of glucose transport is correlated with the sensitivity change. In one embodiment, the processor module is configured to prohibit calibration of the glucose-related sensor data point when the stability of glucose transport falls below a threshold. In one embodiment, the processor module is configured to initiate filtering of the glucose-related sensor data point when the stability of glucose transport falls below a threshold.

Another aspect of the present invention is a method for processing data from a glucose sensor in a host, comprising: 1) measuring a first signal associated with glucose and non-glucose related electroactive compounds, wherein the first signal is measured at a first electrode disposed beneath an active enzymatic portion of a membrane system; 2) measuring a second signal associated with a non-glucose related electroactive compound, wherein the second signal is measured at a second electrode that is disposed beneath a non-enzymatic portion of the membrane system; and 3) monitoring the second signal over a time period, whereby a change in the non-glucose related electroactive compound in the host is measured. One embodiment further comprises a step of subtracting the second signal from the first signal, whereby a differential signal comprising at least one glucose sensor data point is determined. The step of subtracting may be performed electronically in the sensor. Alternatively, the step of subtracting may be performed digitally in the sensor or an associated receiver. One embodiment further comprises calibrating the glucose sensor, wherein the step of calibrating comprises: 1) receiving reference data from a reference analyte monitor, the reference data comprising at least two reference data points; 2) providing at least two matched data pairs by matching the reference data to substantially time corresponding sensor data; and 3) calibrating the glucose sensor using the two or more matched data pairs and the differential signal. One embodiment further comprises a step of calibrating the glucose sensor in response to a change in the non-glucose related electroactive compound over the time period. The step of calibrating may comprise receiving reference data from a reference analyte monitor, the reference data comprising at least one reference data point. The step of calibrating may comprise using the change in the non-glucose related electroactive compound over the time period to calibrate the glucose sensor. The step of calibrating may be performed repeatedly at a frequency, wherein the frequency is selected based on the change in the non-glucose related electroactive compound over the time period. One embodiment further comprises prohibiting calibration of the glucose sensor when the change in the non-glucose related electroactive compound rises above a threshold during the time period. One embodiment further comprises filtering the glucose sensor data point when the change in the non-glucose related electroactive compound rises above a threshold during the time period. One embodiment further comprises measuring a third signal in the host by obtaining at least one non-glucose constant data point, wherein the third signal is measured beneath the membrane system. One embodiment further comprises monitoring the third signal over a time period, whereby a sensitivity change associated with solute transport through the membrane system is measured. In one embodiment, an oxygen-measuring electrode disposed beneath the non-enzymatic portion of the membrane system measures the third signal. In one embodiment, the first electrode measures the third signal by incrementally measuring oxygen. In one embodiment, an oxygen sensor disposed beneath the membrane system measures the third signal. One embodiment further comprises determining whether a glucose-to-oxygen ratio exceeds a threshold level by calculating a value from the first signal and the second signal, wherein the value is indicative of the glucose-to-oxygen ratio. One embodiment further comprises calibrating the glucose sensor in response to the sensitivity change measured over a time period. The step of calibrating may comprise receiving reference data from a reference analyte monitor, the reference data comprising at least one reference data point. The step of calibrating may comprise using the sensitivity change. The step of calibrating may be performed repeatedly at a frequency, wherein the frequency is selected based on the sensitivity change. One embodiment further comprises determining a glucose transport stability through the membrane system, wherein the glucose transport stability corresponds to the sensitivity change over a period of time. One embodiment further comprises prohibiting calibration of the glucose sensor when the glucose transport stability falls below a threshold. One embodiment further comprises filtering the glucose-related sensor data point when the glucose transport stability falls below a threshold.

Still another aspect of the present invention is a system for measuring glucose in a host, comprising a first working electrode configured to generate a first signal associated with a glucose related electroactive compound and a non-glucose related electroactive compound, wherein the first electrode is disposed beneath an active enzymatic portion of a membrane system on a glucose sensor; a second working electrode configured to generate a second signal associated with the non-glucose related electroactive compound, wherein the second electrode is disposed beneath a non-enzymatic portion of the membrane system on the glucose sensor; and a processor module configured to monitor the second signal over a time period, whereby a change in the non-glucose related electroactive compound is measured. One embodiment further comprises a subtraction module configured to subtract the second signal from the first signal, whereby a differential signal comprising at least one glucose sensor data point is determined. The subtraction module may comprise a differential amplifier configured to electronically subtract the second signal from the first signal. The subtraction module may comprise at least one of hardware and software configured to digitally subtract the second signal from the first signal. One embodiment further comprises a reference electrode, wherein the first working electrode and the second working electrode are operatively associated with the reference electrode. One embodiment further comprises a counter electrode, wherein the first working electrode and the second working electrode are operatively associated with the counter electrode. One embodiment further comprises a first reference electrode and a second reference electrode, wherein the first reference electrode is operatively associated with the first working electrode, and wherein the second reference electrode is operatively associated with the second working electrode. One embodiment further comprises a first counter electrode and a second counter electrode, wherein the first counter electrode is operatively associated with the first working electrode, and wherein the second counter electrode is operatively associated with the second working electrode. One embodiment further comprises a reference input module adapted to obtain reference data from a reference analyte monitor, the reference data comprising at least one reference data point, wherein the processor module is configured to format at least one matched data pair by matching the reference data to substantially time corresponding glucose sensor data and subsequently calibrating the system using at least two matched data pairs and the differential signal. In one embodiment, the processor module is configured to calibrate the system in response to the change in the non-glucose related electroactive compound in the host over the time period. In one embodiment, the processor module is configured to request reference data from a reference analyte monitor, the reference data comprising at least one reference data point, wherein the processor module is configured to recalibrate the system using the reference data. In one embodiment, the processor module is configured to recalibrate the system using the change in the non-glucose related electroactive compound measured over the time period. In one embodiment, the processor module is configured to repeatedly recalibrate at a frequency, wherein the frequency is selected based on the change in the non-glucose related electroactive compound over the time period. In one embodiment, the processor module is configured to prohibit calibration of the system when a change in the non-glucose related electroactive compound rises above a threshold during the time period. In one embodiment, the processor module is configured to filter the glucose sensor data point when the change in the non-glucose related electroactive compound rises above a threshold during the time period. One embodiment further comprises a third electrode configured to generate a third signal, the third signal comprising at least one non-glucose constant analyte data point, wherein the third electrode is disposed beneath the membrane system on the sensor. The third electrode may be configured to measure oxygen. In one embodiment, the processor module is configured to determine whether a glucose-to-oxygen ratio exceeds a threshold level, wherein a value indicative of the glucose-to-oxygen ratio is calculated from the first signal and the second signal. In one embodiment, the processor module is configured to monitor the third signal over a time period, whereby a sensitivity change associated with solute transport through the membrane system is measured. In one embodiment, the processor module is configured to calibrate the glucose-related sensor data point in response to the sensitivity change. In one embodiment, the processor module is configured to receive reference data from a reference analyte monitor, the reference data comprising at least one reference data point, wherein the processor module is configured to calibrate the glucose sensor data point using the reference data point. In one embodiment, the processor module is configured to calibrate the glucose-related sensor data point repeatedly at a frequency, wherein the frequency is selected based on the sensitivity change. One embodiment further comprises a stability module configured to determine a stability of glucose transport through the membrane system, wherein the stability of glucose transport is correlated with the sensitivity change. In one embodiment, the processor module is configured to prohibit calibration of the glucose-related sensor data point when the stability of glucose transport falls below a threshold. In one embodiment, the processor module is configured to filter the glucose-related sensor data point when the stability of glucose transport falls below a threshold.

DETAILED DESCRIPTION OF THE PREFERRED EMBODIMENT

Figure 1A:
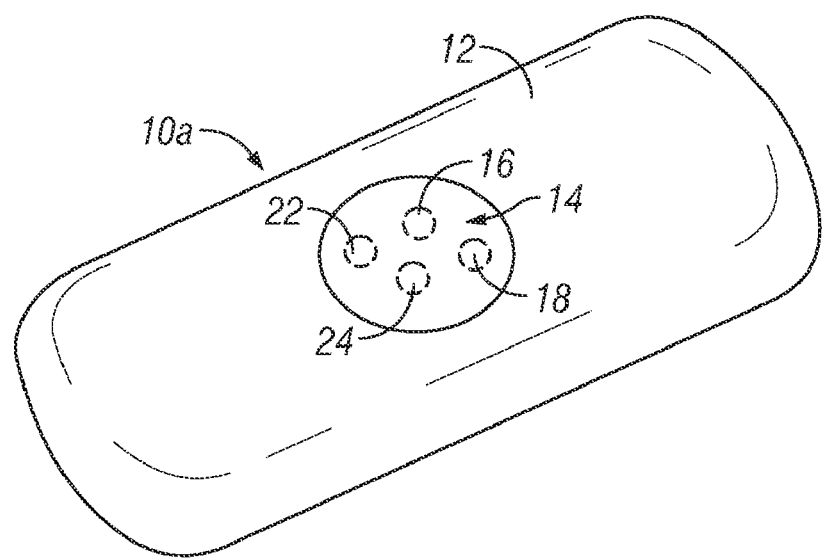
FIG. 1A is a perspective view of a continuous analyte sensor, including an implantable body with a membrane system disposed thereon

The following description and examples illustrate some exemplary embodiments of the disclosed invention in detail. Those of skill in the art will recognize that there are numerous variations and modifications of this invention that are encompassed by its scope. Accordingly, the description of a certain exemplary embodiment should not be deemed to limit the scope of the present invention.

Definitions

In order to facilitate an understanding of the disclosed invention, a number of terms are defined below.

The term "analyte," as used herein, is a broad term and is used in its ordinary sense, including, but not limited to, to refer to a substance or chemical constituent in a biological fluid (for example, blood, interstitial fluid, cerebral spinal fluid, lymph fluid or urine) that can be analyzed. Analytes may include naturally occurring substances, artificial substances, metabolites, and/or reaction products. In some embodiments, the analyte for measurement by the sensor heads, devices, and methods disclosed herein is glucose.

However, other analytes are contemplated as well, including but not limited to acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobinopathies, A,S,C,E, D-Punjab, beta-thalassemia, hepatitis B virus, HCMV, HIV-1, HTLV-1, Leber hereditary optic neuropathy, MCAD, RNA, PKU, Plasmodium vivax, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17 alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella, *Mycobacterium leprae*, *Mycoplasma pneumoniae*, *Myoglobin*, *Onchocerca volvulus*, parainfluenza virus, *Plasmodium falciparum*, poliovirus, *Pseudomonas aeruginosa*, respiratory syncytial virus, rickettsia (scrub typhus), *Schistosoma mansoni*, *Toxoplasma gondii*, *Trepenoma pallidium*, *Trypanosoma cruzi/rangeli*, vesicular stomatis virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin. Salts, sugar, protein, fat, vitamins and hormones naturally occurring in blood or interstitial fluids may also constitute analytes in certain embodiments. The analyte may be naturally present in the biological fluid, for example, a metabolic product, a hormone, an antigen, an antibody, and the like. Alternatively, the analyte may be introduced into the body, for example, a contrast agent for imaging, a radioisotope, a chemical agent, a fluorocarbon-based synthetic blood, or a drug or pharmaceutical composition, including but not limited to insulin; ethanol; cannabis (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbituates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The metabolic products of drugs and pharmaceutical compositions are also contemplated analytes. Analytes such as neurochemicals and other chemicals generated within the body may also be analyzed, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

The term "continuous glucose sensor," as used herein, is a broad term and is used in its ordinary sense, including, but not limited to, a device that continuously or continually measures glucose concentration, for example, at time intervals ranging from fractions of a second up to, for example, 1, 2, or 5 minutes, or longer. It should be understood that continuous glucose sensors can continually measure glucose concentration without requiring user initiation and/or interaction for each measurement, such as described with reference to U.S. Pat. No. 6,001,067, for example.

The phrase "continuous glucose sensing," as used herein, is a broad term and is used in its ordinary sense, including, but not limited to, the period in which monitoring of plasma glucose concentration is continuously or continually performed, for example, at time intervals ranging from fractions of a second up to, for example, 1, 2, or 5 minutes, or longer.

The term "biological sample," as used herein, is a broad term and is used in its ordinary sense, including, but not limited to, sample of a host body, for example, blood, interstitial fluid, spinal fluid, saliva, urine, tears, sweat, or the like.

The term "host," as used herein, is a broad term and is used in its ordinary sense, including, but not limited to, mammals such as humans.

The term "biointerface membrane," as used herein, is a broad term and is used in its ordinary sense, including, but not limited to, a permeable or semi-permeable membrane that can include two or more domains and is typically constructed of materials of a few microns thickness or more, which can be placed over the sensing region to keep host cells (for example, macrophages) from gaining proximity to, and thereby damaging the membrane system or forming a barrier cell layer and interfering with the transport of glucose across the tissue-device interface.

The term "membrane system," as used herein, is a broad term and is used in its ordinary sense, including, but not limited to, a permeable or semi-permeable membrane that can be comprised of two or more domains and is typically constructed of materials of a few microns thickness or more, which may be permeable to oxygen and are optionally permeable to glucose. In one example, the membrane system comprises an immobilized glucose oxidase enzyme, which enables an electrochemical reaction to occur to measure a concentration of glucose.

The term "domain," as used herein is a broad term and is used in its ordinary sense, including, but not limited to, regions of a membrane that can be layers, uniform or non-uniform gradients (for example, anisotropic), functional aspects of a material, or provided as portions of the membrane.

The term "copolymer," as used herein, is a broad term and is used in its ordinary sense, including, but not limited to, polymers having two or more different repeat units and includes copolymers, terpolymers, tetrapolymers, or the like.

The term "sensing region," as used herein, is a broad term and is used in its ordinary sense, including, but not limited to, the region of a monitoring device responsible for the detection of a particular analyte. In one embodiment, the sensing region generally comprises a non-conductive body, at least one electrode, a reference electrode and a optionally a counter electrode passing through and secured within the body forming an electrochemically reactive surface at one location on the body and an electronic connection at another location on the body, and a membrane system affixed to the body and covering the electrochemically reactive surface.

The term "electrochemically reactive surface," as used herein, is a broad term and is used in its ordinary sense, including, but not limited to, the surface of an electrode where an electrochemical reaction takes place. In one embodiment, a working electrode measures hydrogen peroxide creating a measurable electronic current.

The term "electrochemical cell," as used herein, is a broad term and is used in its ordinary sense, including, but not limited to, a device in which chemical energy is converted to electrical energy. Such a cell typically consists of two or more electrodes held apart from each other and in contact with an electrolyte solution. Connection of the electrodes to a source of direct electric current renders one of them negatively charged and the other positively charged. Positive ions in the electrolyte migrate to the negative electrode (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction.

The term "enzyme" as used herein, is a broad term and is used in its ordinary sense, including, but not limited to, a protein or protein-based molecule that speeds up a chemical reaction occurring in a living thing. Enzymes may act as catalysts for a single reaction, converting a reactant (also called an analyte herein) into a specific product. In one exemplary embodiment of a glucose oxidase-based glucose sensor, an enzyme, glucose oxidase (GOX) is provided to react with glucose (the analyte) and oxygen to form hydrogen peroxide.

The term "co-analyte" as used herein, is a broad term and is used in its ordinary sense, including, but not limited to, a molecule required in an enzymatic reaction to react with the analyte and the enzyme to form the specific product being measured. In one exemplary embodiment of a glucose sensor, an enzyme, glucose oxidase (GOX) is provided to react with glucose and oxygen (the co-analyte) to form hydrogen peroxide.

The term "constant analyte" as used herein, is a broad term and is used in its ordinary sense, including, but not limited to, an analyte that remains relatively constant over a time period, for example over an hour to a day as compared to other variable analytes. For example, in a person with diabetes, oxygen and urea may be relatively constant analytes in particular tissue compartments relative to glucose, which is known to oscillate between about 40 and 400 mg/dL during a 24-hour cycle. Although analytes such as oxygen and urea are known to oscillate to a lesser degree, for example due to physiological processes in a host, they are substantially constant, relative to glucose, and can be digitally filtered, for example low pass filtered, to minimize or eliminate any relatively low amplitude oscillations. Constant analytes other than oxygen and urea are also contemplated.

The term "proximal" as used herein, is a broad term and is used in its ordinary sense, including, but not limited to, near to a point of reference such as an origin or a point of attachment. For example, in some embodiments of a membrane system that covers an electrochemically reactive surface, the electrolyte domain is located more proximal to the electrochemically reactive surface than the resistance domain.

The term "distal" as used herein, is a broad term and is used in its ordinary sense, including, but not limited to, spaced relatively far from a point of reference, such as an origin or a point of attachment. For example, in some embodiments of a membrane system that covers an electrochemically reactive surface, a resistance domain is located more distal to the electrochemically reactive surfaces than the electrolyte domain.

The term "substantially" as used herein, is a broad term and is used in its ordinary sense, including, but not limited to, being largely but not necessarily wholly that which is specified.

The term "computer," as used herein, is broad term and is used in its ordinary sense, including, but not limited to, machine that can be programmed to manipulate data.

The term "modem," as used herein, is a broad term and is used in its ordinary sense, including, but not limited to, an electronic device for converting between serial data from a computer and an audio signal suitable for transmission over a telecommunications connection to another modem.

The terms "processor module" and "microprocessor," as used herein, are broad terms and are used in their ordinary sense, including, but not limited to, a computer system, state machine, processor, or the like designed to perform arithmetic and logic operations using logic circuitry that responds to and processes the basic instructions that drive a computer.

The term "ROM," as used herein, is a broad term and is used in its ordinary sense, including, but not limited to, read-only memory, which is a type of data storage device manufactured with fixed contents. ROM is broad enough to include EEPROM, for example, which is electrically erasable programmable read-only memory (ROM).

The term "RAM," as used herein, is a broad term and is used in its ordinary sense, including, but not limited to, a data storage device for which the order of access to different locations does not affect the speed of access. RAM is broad enough to include SRAM, for example, which is static random access memory that retains data bits in its memory as long as power is being supplied.

The term "A/D Converter," as used herein, is a broad term and is used in its ordinary sense, including, but not limited to, hardware and/or software that converts analog electrical signals into corresponding digital signals.

The term "RF transceiver," as used herein, is a broad term and is used in its ordinary sense, including, but not limited to, a radio frequency transmitter and/or receiver for transmitting and/or receiving signals.

The terms "raw data stream" and "data stream," as used herein, are broad terms and are used in their ordinary sense, including, but not limited to, an analog or digital signal directly related to the analyte concentration measured by the analyte sensor. In one example, the raw data stream is digital data in "counts" converted by an A/D converter from an analog signal (for example, voltage or amps) representative of an analyte concentration. The terms broadly encompass a plurality of time spaced data points from a substantially continuous analyte sensor, which comprises individual measurements taken at time intervals ranging from fractions of a second up to, for example, 1, 2, or 5 minutes or longer.

The term "counts," as used herein, is a broad term and is used in its ordinary sense, including, but not limited to, a unit of measurement of a digital signal. In one example, a raw data stream measured in counts is directly related to a voltage (for example, converted by an A/D converter), which is directly related to current from a working electrode.

The term "electronic circuitry," as used herein, is a broad term and is used in its ordinary sense, including, but not limited to, the components (for example, hardware and/or software) of a device configured to process data. In the case of an analyte sensor, the data includes biological information obtained by a sensor regarding the concentration of the analyte in a biological fluid. U.S. Pat. Nos. 4,757,022, 5,497,772 and 4,787,398, which are hereby incorporated by reference in their entirety, describe suitable electronic circuits that can be utilized with devices of certain embodiments.

The term "potentiostat," as used herein, is a broad term and is used in its ordinary sense, including, but not limited to, an electrical system that applies a potential between the working and reference electrodes of a two- or three-electrode cell at a preset value and measures the current flow through the working electrode. The potentiostat forces whatever current is necessary to flow between the working and counter electrodes to keep the desired potential, as long as the needed cell voltage and current do not exceed the compliance limits of the potentiostat.

The terms "operably connected" and "operably linked," as used herein, are broad terms and are used in their ordinary sense, including, but not limited to, one or more components being linked to another component(s) in a manner that allows transmission of signals between the components. For example, one or more electrodes can be used to detect the amount of glucose in a sample and convert that information into a signal; the signal can then be transmitted to an electronic circuit. In this case, the electrode is "operably linked" to the electronic circuit. These terms are broad enough to include wired and wireless connectivity.

The term "smoothing" and "filtering," as used herein, are broad terms and are used in their ordinary sense, including, but not limited to, modification of a set of data to make it smoother and more continuous and remove or diminish outlying points, for example, by performing a moving average of the raw data stream.

The term "algorithm," as used herein, is a broad term and is used in its ordinary sense, including, but not limited to, the computational processes (for example, programs) involved in transforming information from one state to another, for example using computer processing.

The term "regression," as used herein, is a broad term and is used in its ordinary sense, including, but not limited to, finding a line in which a set of data has a minimal measurement (for example, deviation) from that line. Regression can be linear, non-linear, first order, second order, and so forth. One example of regression is least squares regression.

The term "pulsed amperometric detection," as used herein, is a broad term and is used in its ordinary sense, including, but not limited to, an electrochemical flow cell and a controller, which applies the potentials and monitors current generated by the electrochemical reactions. The cell can include one or multiple working electrodes at different applied potentials. Multiple electrodes can be arranged so that they face the chromatographic flow independently (parallel configuration), or sequentially (series configuration).

The term "calibration," as used herein, is a broad term and is used in its ordinary sense, including, but not limited to, the process of determining the relationship between the sensor data and corresponding reference data, which may be used to convert sensor data into meaningful values substantially equivalent to the reference. In some embodiments, namely in continuous analyte sensors, calibration may be updated or recalibrated over time as changes in the relationship between the sensor and reference data occur, for example due to changes in sensitivity, baseline, transport, metabolism, or the like.

The term "sensor analyte values" and "sensor data," as used herein, are broad terms and are used in their ordinary sense, including, but not limited to, data received from a continuous analyte sensor, including one or more time-spaced sensor data points.

The term "reference analyte values" and "reference data," as used herein, are broad terms and are used in their ordinary sense, including, but not limited to, data from a reference analyte monitor, such as a blood glucose meter, or the like, including one or more reference data points. In some embodiments, the reference glucose values are obtained from a self-monitored blood glucose (SMBG) test (for example, from a finger or forearm blood test) or a YSI (Yellow Springs Instruments) test, for example.

The term "matched data pairs," as used herein, is a broad term and is used in its ordinary sense, including, but not limited to, reference data (for example, one or more reference analyte data points) matched with substantially time corresponding sensor data (for example, one or more sensor data points).

The terms "interferants" and "interfering species," as used herein, are broad terms and are used in their ordinary sense, including, but not limited to, effects and/or species that interfere with the measurement of an analyte of interest in a sensor to produce a signal that does not accurately represent the analyte measurement. In one example of an electrochemical sensor, interfering species are compounds with an oxidation potential that overlaps with the analyte to be measured, producing a false positive signal.

Overview

The preferred embodiments provide a continuous analyte sensor that measures a concentration of the analyte of interest or a substance indicative of the concentration or presence of the analyte. In some embodiments, the analyte sensor is an invasive, minimally invasive, or non-invasive device, for example a subcutaneous, transdermal, or intravascular device. In some embodiments, the analyte sensor may analyze a plurality of intermittent biological samples. The analyte sensor may use any method of analyte-measurement, including enzymatic, chemical, physical, electrochemical, spectrophotometric, polarimetric, calorimetric, radiometric, or the like.

In general, analyte sensors provide at least one working electrode and at least one reference electrode, which are configured to measure a signal associated with a concentration of the analyte in the host, such as described in more detail below, and as appreciated by one skilled in the art. The output signal is typically a raw data stream that is used to provide a useful value of the measured analyte concentration in a host to the patient or doctor, for example. However, the analyte sensors of the preferred embodiments may further measure at least one additional signal associated with the baseline and/or sensitivity of the analyte sensor, thereby enabling monitoring of baseline and/or sensitivity changes that may occur in a continuous analyte sensor over time.

In general, continuous analyte sensors define a relationship between sensor-generated measurements (for example, current in nA or digital counts after A/D conversion) and a reference measurement (for example, mg/dL or mmol/L) that are meaningful to a user (for example, patient or doctor). In the case of an implantable enzyme-based electrochemical glucose sensors, the sensing mechanism generally depends on phenomena that are linear with glucose concentration, for example: (1) diffusion of glucose through a membrane system (for example, biointerface membrane and membrane system) situated between implantation site and the electrode surface, (2) an enzymatic reaction within the membrane system (for example, membrane system), and (3) diffusion of the $H_2O_2$ to the sensor. Because of this linearity, calibration of the sensor can be understood by solving an equation:

$$y=mx+b$$

where y represents the sensor signal (counts), x represents the estimated glucose concentration (mg/dL), m represents the sensor sensitivity to glucose (counts/mg/dL), and b represents the baseline signal (counts). Because both sensitivity m and baseline b change over time in vivo, calibration has conventionally required at least two independent, matched data pairs ($x_1$, $y_1$; $x_2$, $y_2$) to solve for m and b and thus allow glucose estimation when only the sensor signal, y is available. Matched data pairs can be created by matching reference data (for example, one or more reference glucose data points from a blood glucose meter, or the like) with substantially time corresponding sensor data (for example, one or more glucose sensor data points) to provide one or more matched data pairs, such as described in co-pending U.S. patent application Ser. No. 10/633,367, which is incorporated herein by reference in its entirety.

Accordingly, in some embodiments, the sensing region is configured to measure changes in sensitivity of the analyte sensor over time, which can be used to trigger calibration, update calibration, avoid inaccurate calibration (for example, calibration during unstable periods), and/or trigger filtering of the sensor data. Namely, the analyte sensor is configured to measure a signal associated with a non-analyte constant in the host. Preferably, the non-analyte constant signal is measured beneath the membrane system on the sensor. In one example of a glucose sensor, a non-glucose constant that can be measured is oxygen, wherein a measured change in oxygen transport is indicative of a change in the sensitivity of the glucose signal, which can be measured by switching the bias potential of the working electrode, an auxiliary oxygen-measuring electrode, an oxygen sensor, or the like, as described in more detail elsewhere herein.

Alternatively or additionally, in some embodiments, the sensing region is configured to measure changes in the amount of background noise (baseline) in the signal, which can be used to trigger calibration, update calibration, avoid inaccurate calibration (for example, calibration during unstable periods), and/or trigger filtering of the sensor data. In one example of a glucose sensor, the baseline is composed substantially of signal contribution due to factors other than glucose (for example, interfering species, non-reaction-related hydrogen peroxide, or other electroactive species with an oxidation potential that overlaps with hydrogen peroxide). Namely, the glucose sensor is configured to measure a signal associated with the baseline (all non-glucose related current generated) measured by sensor in the host. In some embodiments, an auxiliary electrode located beneath a non-enzymatic portion of the membrane system is used to measure the baseline signal. In some embodiments, the baseline signal is subtracted from the glucose signal (which includes the baseline) to obtain the signal contribution substantially only due to glucose. Subtraction may be accomplished electronically in the sensor using a differential amplifier, digitally in the receiver, and/or otherwise in the hardware or software of the sensor or receiver as is appreciated by one skilled in the art, and as described in more detail elsewhere herein.

One skilled in the art appreciates that the above-described sensitivity and baseline signal measurements can be combined to benefit from both measurements in a single analyte sensor.

Exemplary Continuous Glucose Sensor Configurations

Although two exemplary glucose sensor configurations are described in detail below, it should be understood that the systems and methods described herein can be applied to any device capable of continually or continuously detecting a concentration of analyte of interest and providing an output signal that represents the concentration of that analyte, for example oxygen, lactose, hormones, cholesterol, medicaments, viruses, or the like.

FIG. 1A is a perspective view of an analyte sensor, including an implantable body with a sensing region including a membrane system disposed thereon. In the illustrated embodiment, the analyte sensor 10a includes a body 12 and a sensing region 14 including membrane and electrode systems configured to measure the analyte. In this embodiment, the sensor 10a is preferably wholly implanted into the subcutaneous tissue of a host, such as described in co-pending. U.S. patent application Ser. No. 10/885,476 filed Jul. 6, 2004 and entitled "SYSTEMS AND METHODS FOR MANUFACTURE OF AN ANALYTE SENSOR INCLUDING A MEMBRANE SYSTEM"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/633,367 filed Aug. 1, 2003 entitled, "SYSTEM AND METHODS FOR PROCESSING ANALYTE SENSOR DATA"; and U.S. Pat. No. 6,001,067 issued Dec. 14, 1999 and entitled "DEVICE AND METHOD FOR DETERMINING ANALYTE LEVELS", each of which are incorporated herein by reference in their entirety The body 12 of the sensor 10a can be formed from a variety of materials, including metals, ceramics, plastics, or composites thereof. In one embodiment, the sensor is formed from thermoset molded around the sensor electronics. Co-pending U.S. patent application Ser. No. 10/646,333, entitled, "OPTIMIZED DEVICE GEOMETRY FOR AN IMPLANTABLE GLUCOSE DEVICE" discloses suitable configurations for the body, and is incorporated by reference in its entirety.

In some embodiments, the sensing region 14 includes a glucose-measuring working electrode 16, an optional auxiliary working electrode 18, a reference electrode 20, and a counter electrode 22. Generally, the sensing region 14 includes means to measure two different signals, 1) a first signal associated with glucose and non-glucose related electroactive compounds having a first oxidation potential, wherein the first signal is measured at the glucose-measuring working electrode disposed beneath an active enzymatic portion of a membrane system, and 2) a second signal associated with the baseline and/or sensitivity of the glucose sensor. In some embodiments, wherein the second signal measures sensitivity, the signal is associated with at least one non-glucose constant data point, for example, wherein the auxiliary working electrode 18 is configured to measure oxygen. In some embodiments, wherein the second signal measures baseline, the signal is associated with at non-glucose related electroactive compounds having the first oxidation potential, wherein the second signal is measured at an auxiliary working electrode 18 and is disposed beneath a non-enzymatic portion of the membrane system, such as described in more detail elsewhere herein.

Preferably, a membrane system (see FIG. 2A) is deposited over the electroactive surfaces of the sensor 10*a* and includes a plurality of domains or layers, such as described in more detail below, with reference to FIGS. 2A and 2B. In general, the membrane system may be disposed over (deposited on) the electroactive surfaces using methods appreciated by one skilled in the art. See co-pending U.S. patent application Ser. No. 10/885,476, filed Jul. 6, 2004 and entitled "SYSTEMS AND METHODS FOR MANUFACTURE OF AN ANALYTE SENSOR INCLUDING A MEMBRANE SYSTEM," which is incorporated herein by reference in its entirety.

The sensing region 14 comprises electroactive surfaces, which are in contact with an electrolyte phase (not shown), which is a free-flowing fluid phase disposed between the membrane system 22 and the electroactive surfaces. In this embodiment, the counter electrode is provided to balance the current generated by the species being measured at the working electrode. In the case of glucose oxidase based analyte sensors, the species being measured at the working electrode is $H_2O_2$. Glucose oxidase catalyzes the conversion of oxygen and glucose to hydrogen peroxide and gluconate according to the following reaction:

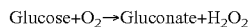

$$Glucose + O_2 \rightarrow Gluconate + H_2O_2$$

The change in $H_2O_2$ can be monitored to determine glucose concentration because for each glucose molecule metabolized, there is a proportional change in the product $H_2O_2$. Oxidation of $H_2O_2$ by the working electrode is balanced by reduction of ambient oxygen, enzyme generated $H_2O_2$, or other reducible species at the counter electrode. The $H_2O_2$ produced from the glucose oxidase reaction further reacts at the surface of the working electrode and produces two protons ($2H^+$), two electrons ($2e^-$), and one oxygen molecule ($O_2$). Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that is used to provide a useful value of the measured analyte concentration in a host to the patient or doctor, for example.

Figure 1B:
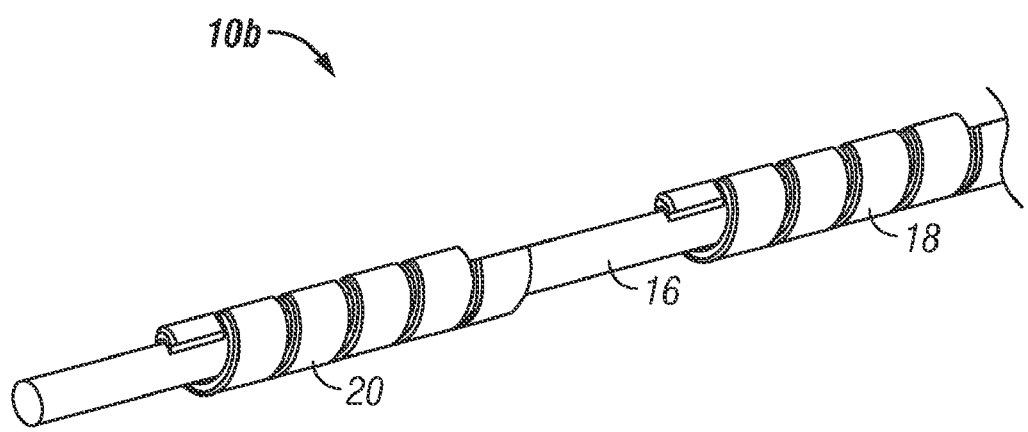
FIG. 1B is an expanded view of an alternative embodiment of a continuous analyte sensor, illustrating the in vivo portion of the sensor.

FIG. 1B is an expanded view of an alternative exemplary embodiment of a continuous analyte sensor 10*b*, also referred to as a transcutaneous analyte sensor, particularly illustrating the in vivo portion of the sensor. In this embodiment, the in vivo portion of the sensor 10*b* is the portion adapted for insertion under the host's skin, while an ex vivo portion of the sensor (not shown) is the portion that remains above the host's skin after sensor insertion and operably connects to an electronics unit. In the illustrated embodiment, the analyte sensor 10*b*, includes three electrodes: a glucose-measuring working electrode 16, an optional auxiliary working electrode 18, and at least one additional electrode 20, which may function as a counter and/or reference electrode, hereinafter referred to as the reference electrode 20. Generally, the sensor 10*b* may include the ability to measure two different signals, 1) a first signal associated with glucose and non-glucose related electroactive compounds having a first oxidation potential, wherein the first signal is measured at the glucose-measuring working electrode disposed beneath an active enzymatic portion of a membrane system, and 2) a second signal associated with the baseline and/or sensitivity of the glucose sensor, such as described in more detail above with reference to FIG. 1A.

Preferably, each electrode is formed from a fine wire, with a diameter in the range of 0.001 to 0.010 inches, for example, and may be formed from plated wire or bulk material, however the electrodes may be deposited on a substrate or other known configurations as is appreciated by one skilled in the art.

In one embodiment, the glucose-measuring working electrode 16 comprises a wire formed from a conductive material, such as platinum, palladium, graphite, gold, carbon, conductive polymer, or the like. The glucose-measuring working electrode 16 is configured and arranged to measure the concentration of glucose. The glucose-measuring working electrode 16 is covered with an insulating material, for example a non-conductive polymer. Dip-coating, spray-coating, or other coating or deposition techniques can be used to deposit the insulating material on the working electrode, for example. In one preferred embodiment, the insulating material comprises Parylene, which can be an advantageous conformal coating for its strength, lubricity, and electrical insulation properties, however, a variety of other insulating materials can be used, for example, fluorinated polymers, polyethyleneterephthalate, polyurethane, polyimide, or the like.

In this embodiment, the auxiliary working electrode 18 comprises a wire formed from a conductive material, such as described with reference to the glucose-measuring working electrode 16 above. Preferably, the reference electrode 20, which may function as a reference electrode alone, or as a dual reference and counter electrode, is formed from silver, Silver/Silver chloride, or the like.

Preferably, the electrodes are juxtapositioned and/or twisted with or around each other, however other configurations are also possible. In one example, the auxiliary working electrode 18 and reference electrode 20 may be helically wound around the glucose-measuring working electrode 16 as illustrated in FIG. 1B. Alternatively, the auxiliary working electrode 18 and reference electrode 20 may be formed as a double helix around a length of the glucose-measuring working electrode 16 (not shown). The assembly of wires may then be optionally coated together with an insulating material, similar to that described above, in order to provide an insulating attachment. Some portion of the coated assembly structure is then stripped, for example using an excimer laser, chemical etching, or the like, to expose the necessary electroactive surfaces. In some alternative embodiments, additional electrodes may be included within the assembly, for example, a three-electrode system (including separate reference and counter electrodes) as is appreciated by one skilled in the art.

Preferably, a membrane system (see FIG. 2B) is deposited over the electroactive surfaces of the sensor 10*b* and includes a plurality of domains or layers, such as described in more detail below, with reference to FIGS. 2A and 2B. The membrane system may be deposited on the exposed electroactive surfaces using known thin film techniques (for example, spraying, electro-depositing, dipping, or the like). In one exemplary embodiment, each domain is deposited by dipping the sensor into a solution and drawing out the sensor at a speed that provides the appropriate domain thickness. In general, the membrane system may be disposed over (deposited on) the electroactive surfaces using methods appreciated by one skilled in the art.

In the illustrated embodiment, the sensor is an enzyme-based electrochemical sensor, wherein the glucose-measuring working electrode 16 measures the hydrogen peroxide produced by the enzyme catalyzed reaction of glucose being detected and creates a measurable electronic current (for example, detection of glucose utilizing glucose oxidase produces $H_2O_2$ peroxide as a by product, $H_2O_2$ reacts with the surface of the working electrode producing two protons ($2H^+$), two electrons ($2e^-$) and one molecule of oxygen ($O_2$) which produces the electronic current being detected), such as described in more detail above and as is appreciated by one skilled in the art. Preferably, one or more potentiostat is employed to monitor the electrochemical reaction at the electroactive surface of the working electrode(s). The potentiostat applies a constant potential to the working electrode and its associated reference electrode to determine the current produced at the working electrode. The current that is produced at the working electrode (and flows through the circuitry to the counter electrode) is substantially proportional to the amount of $H_2O_2$ that diffuses to the working electrodes. The output signal is typically a raw data stream that is used to provide a useful value of the measured analyte concentration in a host to the patient or doctor, for example.

Some alternative analyte sensors that can benefit from the systems and methods of the preferred embodiments include U.S. Pat. No. 5,711,861 to Ward et al., U.S. Pat. No. 6,642,015 to Vachon et al., U.S. Pat. No. 6,654,625 to Say et al., U.S. Pat. No. 6,565,509 to Say et al., U.S. Pat. No. 6,514,718 to Heller, U.S. Pat. No. 6,465,066 to Essenpreis et al., U.S. Pat. No. 6,214,185 to Offenbacher et al., U.S. Pat. No. 5,310,469 to Cunningham et al., and U.S. Pat. No. 5,683,562 to Shaffer et al., U.S. Pat. No. 6,579,690 to Bonnecaze et al., U.S. Pat. No. 6,484,046 to Say et al., U.S. Pat. No. 6,512,939 to Colvin et al., U.S. Pat. No. 6,424,847 to Mastrototaro et al., U.S. Pat. No. 6,424,847 to Mastrototaro et al, for example. All of the above patents are incorporated in their entirety herein by reference and are not inclusive of all applicable analyte sensors; in general, it should be understood that the disclosed embodiments are applicable to a variety of analyte sensor configurations.

Membrane System

In general, analyte sensors include a membrane system that functions to control the flux of a biological fluid therethrough and/or to protect sensitive regions of the sensor from contamination by the biological fluid, for example. Some conventional electrochemical enzyme-based analyte sensors generally include a membrane system that controls the flux of the analyte being measured, protects the electrodes from contamination of the biological fluid, and/or provides an enzyme that catalyzes the reaction of the analyte with a co-factor, for example. See, e.g., co-pending U.S. patent application Ser. No. 10/838,912, filed May 3, 2004 entitled "IMPLANTABLE ANALYTE SENSOR," which is incorporated herein by reference in its entirety.

The membrane system 22 can include any membrane configuration suitable for use with any analyte sensor (such as described with reference to FIGS. 1A and 1B). In the illustrated embodiments, the membrane system 22 includes a plurality of domains, all or some of which can be adhered to the analyte sensor 10 as is appreciated by one skilled in the art. In one embodiment, the membrane system generally provides one or more of the following functions: 1) protection of the exposed electrode surface from the biological environment, 2) diffusion resistance (limitation) of the analyte, 3) a catalyst for enabling an enzymatic reaction, 4) limitation or blocking of interfering species, and 5) hydrophilicity at the electrochemically reactive surfaces of the sensor interface, such as described in co-pending U.S. patent application Ser. No. 10/838,912, filed May 3, 2004 and entitled "IMPLANTABLE ANALYTE SENSOR," which is incorporated herein by reference in its entirety. Accordingly, the membrane system 22 preferably includes a plurality of domains or layers, for example, resistance domain 30, an interference domain 28, an enzyme domain 26 (for example, glucose oxidase), an electrolyte domain 24, and may additionally include a cell disruptive domain, a cell impermeable domain, and/or an oxygen domain (not shown), such as described in more detail in the above-cited U.S. patent application Ser. No. 10/838, 912. However, it is understood that a membrane system modified for other sensors, for example, by including fewer or additional domains is within the scope of the preferred embodiments.

In some embodiments, the domains of the biointerface and membrane systems are formed from materials such as silicone, polytetrafluoroethylene, polyethylene-co-tetrafluoroethylene, polyolefin, polyester, polycarbonate, biostable polytetrafluoroethylene, homopolymers, copolymers, terpolymers of polyurethanes, polypropylene (PP), polyvinylchloride (PVC), polyvinylidene fluoride (PVDF), polybutylene terephthalate (PBT), polymethylmethacrylate (PMMA), polyether ether ketone (PEEK), polyurethanes, cellulosic polymers, polysulfones and block copolymers thereof including, for example, di-block, tri-block, alternating, random and graft copolymers. Co-pending U.S. patent application Ser. No. 10/838,912, which is incorporated herein by reference in its entirety, describes biointerface and membrane system configurations and materials that may be applied to the preferred embodiments.

Figure 2A:
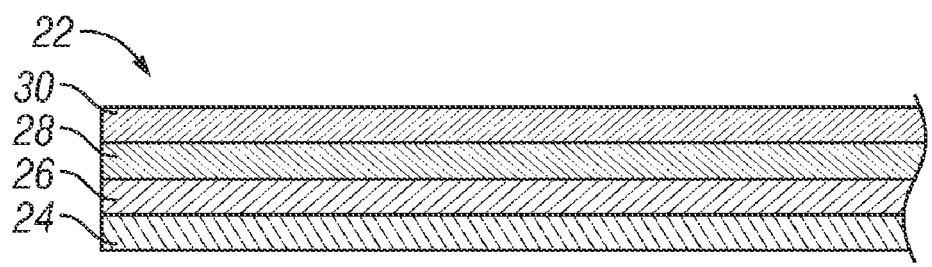
FIG. 2A is a schematic view of a membrane system in one embodiment, configured for deposition over the electroactive surfaces of the analyte sensor of FIG. 1A.
Figure 2B:
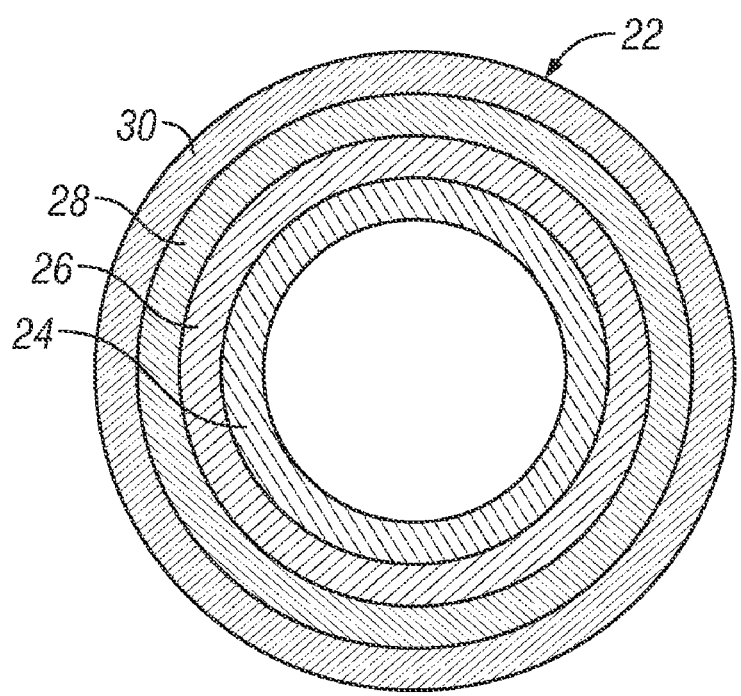
FIG. 2B is a schematic view of a membrane system in an alternative embodiment, configured for deposition over the electroactive surfaces of the analyte sensor of FIG. 1B.

FIGS. 2A and 2B are schematic views membrane systems in some embodiments that may be disposed over the electroactive surfaces of an analyte sensors of FIG. 1A and 1B, respectively, wherein the membrane system includes one or more of the following domains: a resistance domain 30, an enzyme domain 28, an interference domain 26, and an electrolyte domain 24, such as described in more detail below. However, it is understood that the membrane system 22 can be modified for use in other sensors, by including only one or more of the domains, additional domains not recited above, or for other sensor configurations. For example, the interference domain can be removed when other methods for removing interferants are utilized, such as an auxiliary electrode for measuring and subtracting out signal due to interferants. As another example, an "oxygen antenna domain" composed of a material that has higher oxygen solubility than aqueous media so that it concentrates oxygen from the biological fluid surrounding the biointerface membrane can be added. The oxygen antenna domain can then act as an oxygen source during times of minimal oxygen availability and has the capacity to provide on demand a higher rate of oxygen delivery to facilitate oxygen transport to the membrane. This enhances function in the enzyme reaction domain and at the counter electrode surface when glucose conversion to hydrogen peroxide in the enzyme domain consumes oxygen from the surrounding domains. Thus, this ability of the oxygen antenna domain to apply a higher flux of oxygen to critical domains when needed improves overall sensor function.

Electrolyte Domain

In some preferred embodiments, an electrolyte domain 24 is provided to ensure an electrochemical reaction occurs at the electroactive surfaces. Preferably, the electrolyte domain includes a semipermeable coating that maintains hydrophilicity at the electrochemically reactive surfaces of the sensor interface. The electrolyte domain enhances the stability of the interference domain 26 by protecting and supporting the material that makes up the interference domain. The electrolyte domain also assists in stabilizing the operation of the sensor by overcoming electrode start-up problems and drifting problems caused by inadequate electrolyte. The buffered electrolyte solution contained in the electrolyte domain also protects against pH-mediated damage that can result from the formation of a large pH gradient between the substantially hydrophobic interference domain and the electrodes due to the electrochemical activity of the electrodes. In one embodiment, the electrolyte domain 24 includes a flexible, water-swellable, substantially solid gel-like film.

Interference Domain

Interferants are molecules or other species that are electro-reduced or electro-oxidized at the electrochemically reactive surfaces, either directly or via an electron transfer agent, to produce a false signal. In one embodiment, the interference domain 26 prevents the penetration of one or more interferants (for example, ureate, ascorbate, or acetaminophen) into the electrolyte phase around the electrochemically reactive surfaces. Preferably, this type of interference domain is much less permeable to one or more of the interferants than to the analyte.

In one embodiment, the interference domain 26 can include ionic components incorporated into a polymeric matrix to reduce the permeability of the interference domain to ionic interferants having the same charge as the ionic components. In another embodiment, the interference domain 26 includes a catalyst (for example, peroxidase) for catalyzing a reaction that removes interferants. U.S. Pat. Nos. 6,413,396 and 6,565,509 disclose methods and materials for eliminating interfering species. However, in the preferred embodiments any suitable method or material can be employed.

In one embodiment, the interference domain 26 includes a thin membrane that is designed to limit diffusion of species, e.g., those greater than 34 g/mol in molecular weight, for example. The interference domain permits analytes and other substances (for example, hydrogen peroxide) that are to be measured by the electrodes to pass through, while preventing passage of other substances, such as potentially interfering substances. In one embodiment, the interference domain 26 is constructed of polyurethane.

Enzyme Domain

In the preferred embodiments, the enzyme domain 28 provides a catalyst to catalyze the reaction of the analyte and its co-reactant, as described in greater detail above. In preferred embodiments, the enzyme domain includes glucose oxidase. However other oxidases, for example, galactose oxidase or uricase, can be used.

For example, enzyme-based electrochemical analyte sensor performance at least partially depends on a response that is neither limited by enzyme activity nor cofactor concentration. Because enzymes, including glucose oxidase, are subject to deactivation as a function of ambient conditions, this behavior needs to be accounted for in constructing analyte sensors. Preferably, the domain is constructed of aqueous dispersions of colloidal polyurethane polymers including the enzyme. However, some alternative embodiments construct the enzyme domain from an oxygen antenna material, for example, silicone or fluorocarbons, in order to provide a supply of excess oxygen during transient ischemia. Preferably, the enzyme is immobilized within the domain, as is appreciated by one skilled in the art.

Resistance Domain

The resistance domain 30 includes a semipermeable membrane that controls the flux of analytes of interest (for example, glucose and oxygen) to the underlying enzyme domain 28. As a result, the upper limit of linearity of an analyte measurement can be extended to a much higher value than what can be achieved without the resistance domain. In one embodiment of a glucose sensor, the resistance domain 38 exhibits an oxygen-to-glucose permeability ratio of approximately 200:1. As a result, one-dimensional reactant diffusion is adequate to provide excess oxygen at all reasonable glucose and oxygen concentrations found in the subcutaneous matrix (See Rhodes et al., Anal. Chem., 66:1520-1529 (1994)).

In some alternative embodiments, a lower ratio of oxygen-to-glucose can be sufficient to provide excess oxygen by using an oxygen antenna domain (for example, a silicone or fluorocarbon based material or domain) to enhance the supply/transport of oxygen to the enzyme domain. In other words, if more oxygen is supplied to the enzyme, then more glucose can also be supplied to the enzyme without the rate of this reaction being limited by a lack of glucose. In some alternative embodiments, the resistance domain is formed from a silicone composition, such as described in copending U.S. application Ser. No. 10/685,636 filed Oct. 28, 2003, and entitled, "SILICONE COMPOSITION FOR BIOCOMPATIBLE MEMBRANE," which is incorporated herein by reference in its entirety.

In one preferred embodiment, the resistance layer includes a homogenous polyurethane membrane with both hydrophilic and hydrophobic regions to control the diffusion of glucose and oxygen to an analyte sensor, the membrane being fabricated easily and reproducibly from commercially available materials. In preferred embodiments, the thickness of the resistance domain is from about 10 microns or less to about 200 microns or more.

The above-described domains are exemplary and are not meant to be limiting to the following description, for example, their systems and methods are designed for the exemplary enzyme-based electrochemical sensor embodiment.

Membrane Configurations

Figure 3A:
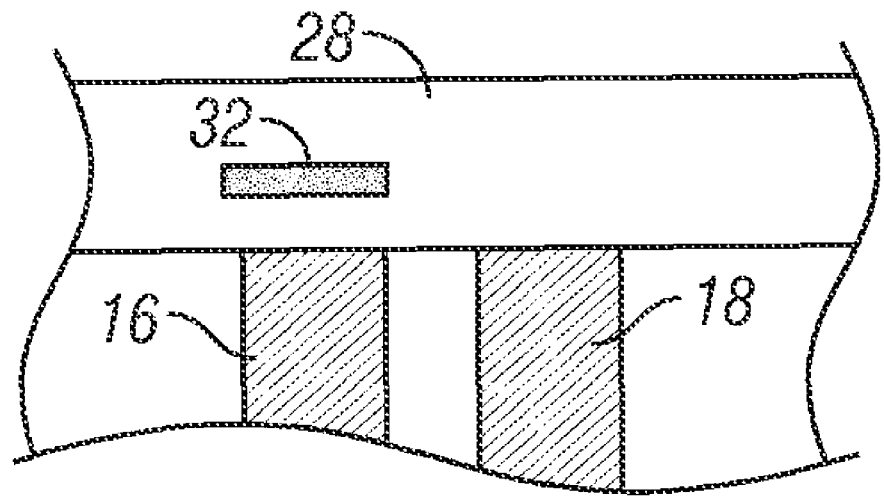
FIG. 3A which is a cross-sectional exploded schematic view of a sensing region of a continuous glucose sensor in one embodiment wherein an active enzyme of an enzyme domain is positioned only over the glucose-measuring working electrode.
Figure 3B:
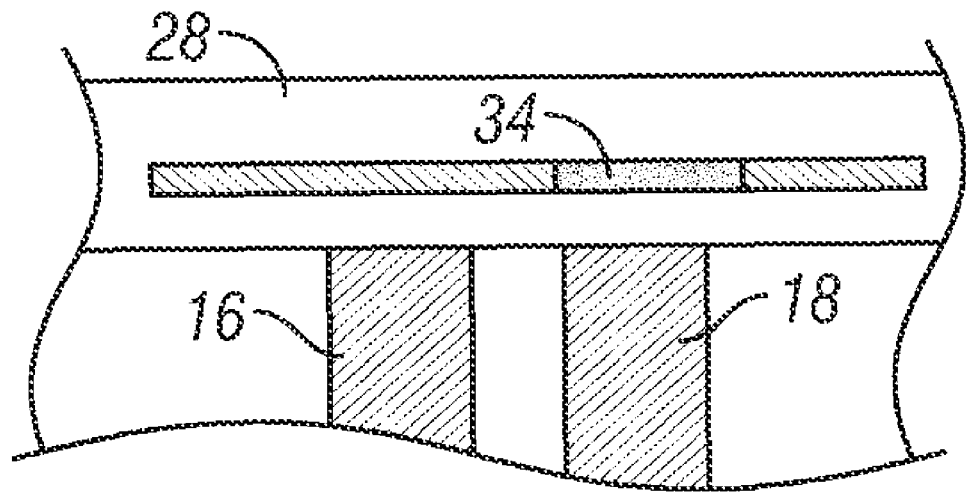
FIG. 3B is a cross-sectional exploded schematic view of a sensing region of a continuous glucose sensor in another embodiment, wherein an active portion of the enzyme within the enzyme domain positioned over the auxiliary working electrode has been deactivated.

FIGS. 3A to 3B are cross-sectional exploded schematic views of the sensing region of a glucose sensor 10, which show architectures of the membrane system 22 disposed over electroactive surfaces of glucose sensors in some embodiments. In the illustrated embodiments of FIGS. 3A and 3B, the membrane system 22 is positioned at least over the glucose-measuring working electrode 16 and the optional auxiliary working electrode 18, however the membrane system may be positioned over the reference and/or counter electrodes 20,22 in some embodiments.

Reference is now made to FIG. 3A, which is a cross-sectional exploded schematic view of the sensing region in one embodiment wherein an active enzyme 32 of the enzyme domain is positioned only over the glucose-measuring working electrode 16. In this embodiment, the membrane system is formed such that the glucose oxidase 32 only exists above the glucose-measuring working electrode 16. In one embodiment, during the preparation of the membrane system 22, the enzyme domain coating solution can be applied as a circular region similar to the diameter of the glucose-measuring working electrode 16. This fabrication can be accomplished in a variety of ways such as screen-printing or pad printing. Preferably, the enzyme domain is pad printed during the enzyme domain fabrication with equipment as available from Pad Print Machinery of Vermont (Manchester, Vt.). This embodiment provides the active enzyme 32 above the glucose-measuring working electrode 16 only, so that the glucose-measuring working electrode 16 (and not the auxiliary working electrode 18) measures glucose concentration. Additionally, this embodiment provides an added advantage of eliminating the consumption of $O_2$ above the counter electrode (if applicable) by the oxidation of glucose with glucose oxidase.

FIG. 3B is a cross-sectional exploded schematic view of a sensing region of the preferred embodiments, and wherein the portion of the active enzyme within the membrane system 22 positioned over the auxiliary working electrode 18 has been deactivated 34. In one alternative embodiment, the enzyme of the membrane system 22 may be deactivated 34 everywhere except for the area covering the glucose-measuring working electrode 16 or may be selectively deactivated only over certain areas (for example, auxiliary working electrode 18, counter electrode 22, and/or reference electrode 20) by irradiation, or the like. In such a case, a mask (for example, such as those used for photolithography) can be placed above the membrane that covers the glucose-measuring working electrode 16. In this way, exposure of the masked membrane to ultraviolet light deactivates the glucose oxidase in all regions except that covered by the mask.

In some alternative embodiments, the membrane system is disposed on the surface of the electrode(s) using known deposition techniques. The electrode-exposed surfaces can be inseted within the sensor body, planar with the sensor body, or extending from the sensor body. Although some examples of membrane systems have been provided above, the concepts described herein can be applied to numerous known architectures not described herein.

Sensor Electronics

In some embodiments, the sensing region may include reference and/or electrodes associated with the glucose-measuring working electrode and separate reference and/or counter electrodes associated with the optional auxiliary working electrode(s). In yet another embodiment, the sensing region may include a glucose-measuring working electrode, an auxiliary working electrode, two counter electrodes (one for each working electrode), and one shared reference electrode. In yet another embodiment, the sensing region may include a glucose-measuring working electrode, an auxiliary working electrode, two reference electrodes, and one shared counter electrode. However, a variety of electrode materials and configurations can be used with the implantable analyte sensor of the preferred embodiments.

In some alternative embodiments, the working electrodes are interdigitated. In some alternative embodiments, the working electrodes each comprise multiple exposed electrode surfaces; one advantage of these architectures is to distribute the measurements across a greater surface area to overcome localized problems that may occur in vivo, for example, with the host's immune response at the biointerface. Preferably, the glucose-measuring and auxiliary working electrodes are provided within the same local environment, such as described in more detail elsewhere herein.

Figure 4:
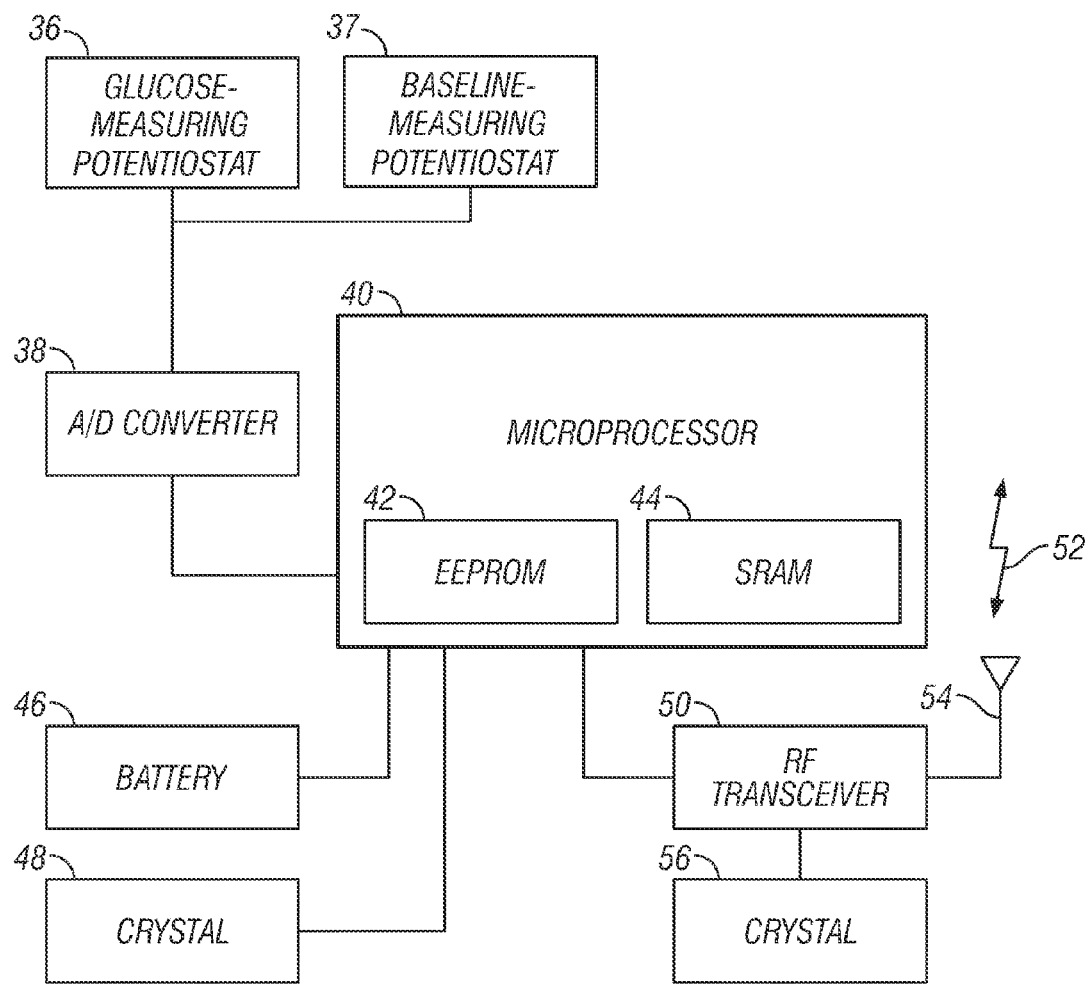
FIG. 4 is a block diagram that illustrates continuous glucose sensor electronics in one embodiment.

FIG. 4 is a block diagram that illustrates the continuous glucose sensor electronics in one embodiment. In this embodiment, a first potentiostat 36 is provided that is operatively associated with the glucose-measuring working electrode 16. The first potentiostat 36 measures a current value at the glucose-measuring working electrode and preferably includes a resistor (not shown) that translates the current into voltage. An optional second potentiostat 37 is provided that is operatively associated with the optional auxiliary working electrode 18. The second potentiostat 37 measures a current value at the auxiliary working electrode 18 and preferably includes a resistor (not shown) that translates the current into voltage. It is noted that in some embodiments, the optional auxiliary electrode can be configured to share the first potentiostat with the glucose-measuring working electrode. An A/D converter 38 digitizes the analog signals from the potentiostats 36, 37 into counts for processing. Accordingly, resulting raw data streams (in counts) can be provided that are directly related to the current measured by each of the potentiostats 36 and 37.

A microprocessor 40, also referred to as the processor module, is the central control unit that houses EEPROM 42 and SRAM 44, and controls the processing of the sensor electronics. It is noted that certain alternative embodiments can utilize a computer system other than a microprocessor to process data as described herein. In other alternative embodiments, an application-specific integrated circuit (ASIC) can be used for some or all the sensor's central processing. The EEPROM 42 provides semi-permanent storage of data, for example, storing data such as sensor identifier (ID) and programming to process data streams (for example, such as described in copending U.S. patent application Ser. No. 10/633,367, which is incorporated by reference herein in its entirety. The SRAM 44 can be used for the system's cache memory, for example for temporarily storing recent sensor data. In some alternative embodiments, memory storage components comparable to EEPROM and SRAM may be used instead of or in addition to the preferred hardware, such as dynamic RAM, non-static RAM, rewritable ROMs, flash memory, or the like.

A battery 46 is operably connected to the microprocessor 40 and provides the necessary power for the sensor 10a. In one embodiment, the battery is a Lithium Manganese Dioxide battery, however any appropriately sized and powered battery can be used (for example, AAA, Nickel-cadmium, Zinc-carbon, Alkaline, Lithium, Nickel-metal hydride, Lithium-ion, Zinc-air, Zinc-mercury oxide, Silver-zinc, and/or hermetically-sealed). In some embodiments the battery is rechargeable. In some embodiments, a plurality of batteries can be used to power the system. In some embodiments, one or more capacitors can be used to power the system. A Quartz Crystal 48 may be operably connected to the microprocessor 40 to maintain system time for the computer system as a whole.

An RF Transceiver 50 may be operably connected to the microprocessor 40 to transmit the sensor data from the sensor 10 to a receiver (see FIGS. 4 and 5) within a wireless transmission 52 via antenna 54. Although an RF transceiver is shown here, some other embodiments can include a wired rather than wireless connection to the receiver. In yet other embodiments, the receiver can be transcutaneously powered via an inductive coupling, for example. A second quartz crystal 56 can provide the system time for synchronizing the data transmissions from the RF transceiver. It is noted that the transceiver 50 can be substituted with a transmitter in other embodiments. In some alternative embodiments other mechanisms such as optical, infrared radiation (IR), ultrasonic, or the like may be used to transmit and/or receive data.

Receiver

Figure 5:
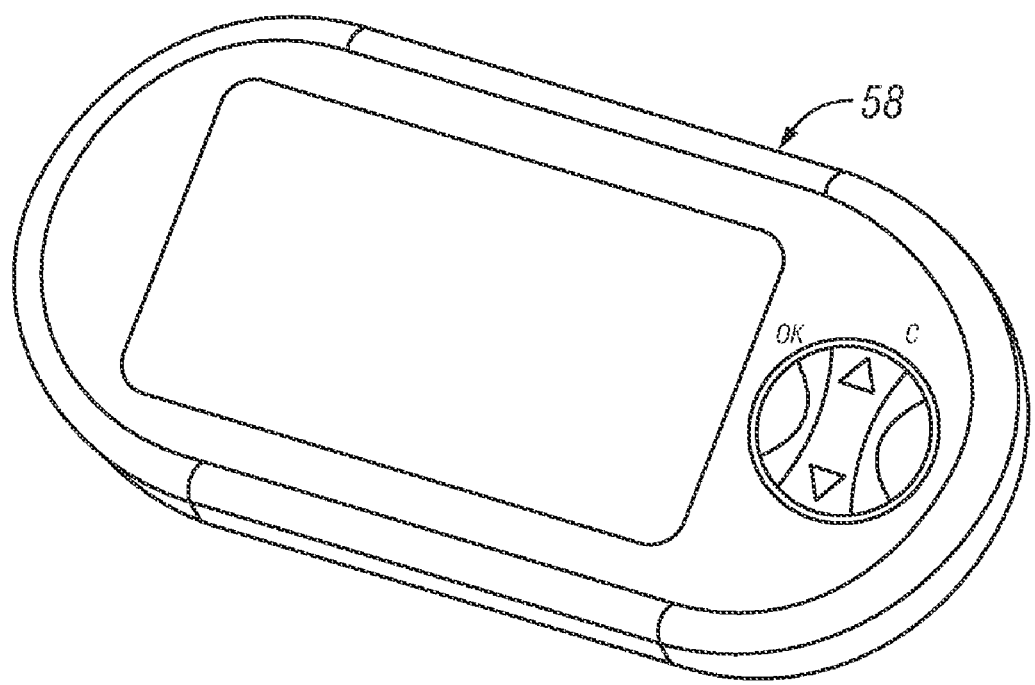
FIG. 5 is a drawing of a receiver for the continuous glucose sensor in one embodiment.

FIG. 5 is a schematic drawing of a receiver for the continuous glucose sensor in one embodiment. The receiver 58 comprises systems necessary to receive, process, and display sensor data from the analyte sensor, such as described in more detail elsewhere herein. Particularly, the receiver 58 may be a pager-sized device, for example, and house a user interface that has a plurality of buttons and/or keypad and a liquid crystal display (LCD) screen, and which may include a backlight. In some embodiments the user interface may also include a speaker, and a vibrator such as described with reference to FIG. 6.

Figure 6:
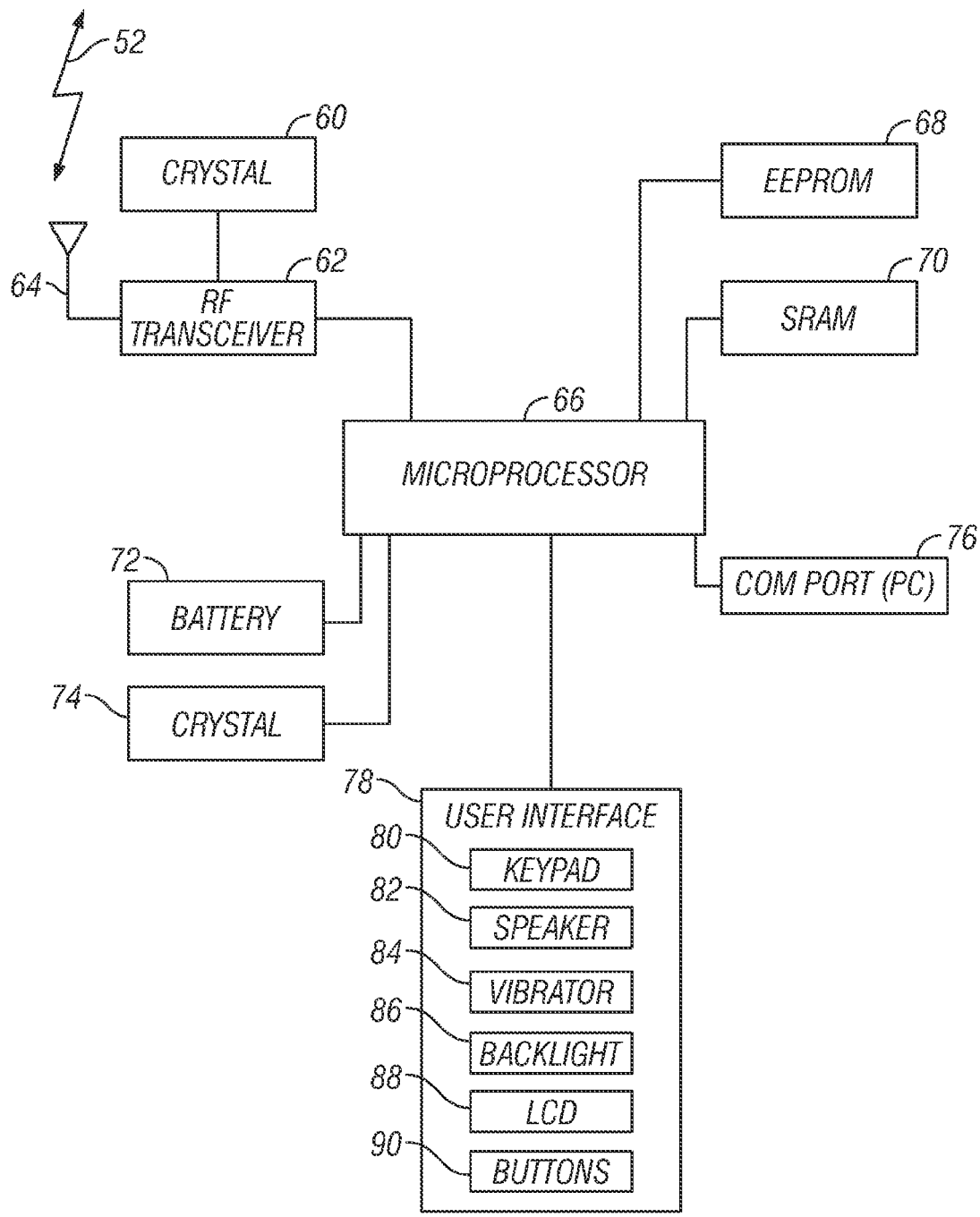
FIG. 6 is a block diagram of the receiver electronics in one embodiment.

FIG. 6 is a block diagram of the receiver electronics in one embodiment. In some embodiments, the receiver comprises a configuration such as described with reference to FIG. 5, above. However, the receiver may comprise any reasonable configuration, including a desktop computer, laptop computer, a personal digital assistant (PDA), a server (local or remote to the receiver), or the like. In some embodiments, a receiver may be adapted to connect (via wired or wireless connection) to a desktop computer, laptop computer, a PDA, a server (local or remote to the receiver), or the like in order to download data from the receiver. In some alternative embodiments, the receiver may be housed within or directly connected to the sensor in a manner that allows sensor and receiver electronics to work directly together and/or share data processing resources. Accordingly, the receiver, including its electronics, may be generally described as a "computer system."

A quartz crystal 60 may be operably connected to an RF transceiver 62 that together function to receive and synchronize data streams via an antenna 64 (for example, transmission 52 from the RF transceiver 50 shown in FIG. 4). Once received, a microprocessor 66 can process the signals, such as described below.

The microprocessor 66, also referred to as the processor module, is the central control unit that provides the processing, such as storing data, calibrating sensor data, downloading data, controlling the user interface by providing prompts, messages, warnings and alarms, or the like. The EEPROM 68 may be operably connected to the microprocessor 66 and provides semi-permanent storage of data, storing data such as receiver ID and programming to process data streams (for example, programming for performing calibration and other algorithms described elsewhere herein). SRAM 70 may be used for the system's cache memory and is helpful in data processing. For example, the SRAM stores information from the continuous glucose sensor for later recall by the patient or a doctor; a patient or doctor can transcribe the stored information at a later time to determine compliance with the medical regimen or a comparison of glucose concentration to medication administration (for example, this can be accomplished by downloading the information through the pc com port 76). In addition, the SRAM 70 can also store updated program instructions and/or patient specific information. In some alternative embodiments, memory storage components comparable to EEPROM and SRAM can be used instead of or in addition to the preferred hardware, such as dynamic RAM, non-static RAM, rewritable ROMs, flash memory, or the like.

A battery 72 may be operably connected to the microprocessor 66 and provides power for the receiver. In one embodiment, the battery is a standard AAA alkaline battery, however any appropriately sized and powered battery can be used. In some embodiments, a plurality of batteries can be used to power the system. In some embodiments, a power port (not shown) is provided permit recharging of rechargeable batteries. A quartz crystal 84 may be operably connected to the microprocessor 66 and maintains system time for the system as a whole.

A PC communication (com) port 76 can be provided to enable communication with systems, for example, a serial communications port, allows for communicating with another computer system (for example, PC, PDA, server, or the like). In one exemplary embodiment, the receiver is able to download historical data to a physician's PC for retrospective analysis by the physician. The PC communication port 76 can also be used to interface with other medical devices, for example pacemakers, implanted analyte sensor patches, infusion devices, telemetry devices, or the like.

A user interface 78 comprises a keypad 80, speaker 82, vibrator 84, backlight 86, liquid crystal display (LCD) 88, and one or more buttons 90. The components that comprise the user interface 78 provide controls to interact with the user.

The keypad 80 can allow, for example, input of user information about himself/herself, such as mealtime, exercise, insulin administration, and reference glucose values. The speaker 82 can provide, for example, audible signals or alerts for conditions such as present and/or predicted hyper- and hypoglycemic conditions. The vibrator 84 can provide, for example, tactile signals or alerts for reasons such as described with reference to the speaker, above. The backlight 94 can be provided, for example, to aid the user in reading the LCD in low light conditions. The LCD 88 can be provided, for example, to provide the user with visual data output. In some embodiments, the LCD is a touch-activated screen. The buttons 90 can provide for toggle, menu selection, option selection, mode selection, and reset, for example. In some alternative embodiments, a microphone can be provided to allow for voice-activated control.

The user interface 78, which is operably connected to the microprocessor 70 serves to provide data input and output for the continuous analyte sensor. In some embodiments, prompts can be displayed to inform the user about necessary maintenance procedures, such as "Calibrate Sensor" or "Replace Battery." In some embodiments, prompts or messages can be displayed on the user interface to convey information to the user, such as malfunction, outlier values, missed data transmissions, or the like. Additionally, prompts can be displayed to guide the user through calibration of the continuous glucose sensor, for example when to obtain a reference glucose value.

Keypad, buttons, touch-screen, and microphone are all examples of mechanisms by which a user can input data directly into the receiver. A server, personal computer, personal digital assistant, insulin pump, and insulin pen are examples of external devices that can be connected to the receiver via PC com port 76 to provide useful information to the receiver. Other devices internal or external to the sensor that measure other aspects of a patient's body (for example, temperature sensor, accelerometer, heart rate monitor, oxygen monitor, or the like) can be used to provide input helpful in data processing. In one embodiment, the user interface can prompt the patient to select an activity most closely related to their present activity, which can be helpful in linking to an individual's physiological patterns, or other data processing. In another embodiment, a temperature sensor and/or heart rate monitor can provide information helpful in linking activity, metabolism, and glucose excursions of an individual. While a few examples of data input have been provided here, a variety of information can be input and can be helpful in data processing as will be understood by one skilled in the art.

Calibration Systems and Methods

As described above in the Overview Section, continuous analyte sensors define a relationship between sensor-generated measurements and a reference measurement that is meaningful to a user (for example, blood glucose in mg/dL). This defined relationship must be monitored to ensure that the continuous analyte sensor maintains a substantially accurate calibration and thereby continually provides meaningful values to a user. Unfortunately, both sensitivity m and baseline b of the calibration are subject to changes that occur in vivo over time (for example, hours to months), requiring updates to the calibration. Generally, any physical property that influences diffusion or transport of molecules through the membrane can alter the sensitivity (and/or baseline) of the calibration. Physical properties that can alter the transport of molecules include, but are not limited to, blockage of surface area due to foreign body giant cells and other barrier cells at the bioactive, distance of capillaries from the membrane, foreign body response/capsule, disease, tissue ingrowth, thickness of membrane system, or the like.

In one example of a change in transport of molecules, an implantable glucose sensor is implanted in the subcutaneous space of a human, which is at least partially covered with a biointerface membrane, such as described in co-pending U.S. patent application Ser. No. 10/647,065, which is incorporated by reference herein in its entirety. Although the body's natural response to a foreign object is to encapsulate the sensor, the architecture of this biointerface membrane encourages tissue ingrowth and neo-vascularization over time, providing transport of solutes (for example, glucose and oxygen) close to the membrane that covers the electrodes. While not wishing to be bound by theory, it is believed that ingrowth of vascularized tissue matures (changes) over time, beginning with a short period of high solute transport during the first few days after implantation, continuing through a time period of significant tissue ingrowth a few days to a week or more after implantation during which low solute transport to the membrane has been observed, and into a mature state of vascularized tissue during which the bed of vascularized tissue provides moderate to high solute transport, which can last for months and even longer after implantation. In some embodiments, this maturation process accounts for a substantial portion of the change in sensitivity and/or baseline of the calibration over time due to changes in solute transport to the membrane.

Accordingly, in one aspect of the preferred embodiments, systems and methods are provided for measuring changes in sensitivity, also referred to as changes in solute transport or biointerface changes, of an analyte sensor 10 implanted in a host over a time period. Preferably, the sensitivity measurement is a signal obtained by measuring a constant analyte other than the analyte being measured by the analyte sensor. For example, in a glucose sensor, a non-glucose constant analyte is measured, wherein the signal is measured beneath the membrane system 22 on the glucose sensor 10. While not wishing to be bound by theory, it is believed that by monitoring the sensitivity over a time period, a change associated with solute transport through the membrane system 22 can be measured and used as an indication of a sensitivity change in the analyte measurement. In other words, a biointerface monitor is provided, which is capable of monitoring changes in the biointerface surrounding an implantable device, thereby enabling the measurement of sensitivity changes of an analyte sensor over time.

In some embodiments, the analyte sensor 10 is provided with an auxiliary electrode 18 configured as a transport-measuring electrode disposed beneath the membrane system 22. The transport-measuring electrode can be configured to measure any of a number of substantially constant analytes or factors, such that a change measured by the transport-measuring electrode can be used to indicate a change in solute (for example, glucose) transport to the membrane system 22. Some examples of substantially constant analytes or factors that can be measured include, but are not limited to, oxygen, carboxylic acids (such as urea), amino acids, hydrogen, pH, chloride, baseline, or the like. Thus, the transport-measuring electrode provides an independent measure of changes in solute transport to the membrane, and thus sensitivity changes over time.

In some embodiments, the transport-measuring electrode measures analytes similar to the analyte being measured by the analyte sensor. For example, in some embodiments of a glucose sensor, water soluble analytes are believed to better represent the changes in sensitivity to glucose over time than non-water soluble analytes (due to the water-solubility of glucose), however relevant information may be ascertained from a variety of molecules. Although some specific examples are described herein, one skilled in the art appreciates a variety of implementations of sensitivity measurements that can be used as to qualify or quantify solute transport through the biointerface of the analyte sensor.

In one embodiment of a glucose sensor, the transport-measuring electrode is configured to measure urea, which is a water-soluble constant analyte that is known to react directly or indirectly at a hydrogen peroxide sensing electrode (similar to the working electrode of the glucose sensor example described in more detail above). In one exemplary implementation wherein urea is directly measured by the transport-measuring electrode, the glucose sensor comprises a membrane system as described in more detail above, however, does not include an active interference domain or active enzyme directly above the transport-measuring electrode, thereby allowing the urea to pass through the membrane system to the electroactive surface for measurement thereon. In one alternative exemplary implementation wherein urea is indirectly measured by the transport-measuring electrode, the glucose sensor comprises a membrane system as described in more detail above, and further includes an active uricase oxidase domain located directly above the transport-measuring electrode, thereby allowing the urea to react at the enzyme and produce hydrogen peroxide, which can be measured at the electroactive surface thereon.

In some embodiments, the change in sensitivity is measured by measuring a change in oxygen concentration, which can be used to provide an independent measurement of the maturation of the biointerface, and to indicate when recalibration of the system may be advantageous. In one alternative embodiment, oxygen is measured using pulsed amperometric detection on the glucose-measuring working electrode 16 (eliminating the need for a separate auxiliary electrode). In another embodiment, the auxiliary electrode is configured as an oxygen-measuring electrode. In another embodiment, an oxygen sensor (not shown) is added to the glucose sensor, as is appreciated by one skilled in the art, eliminating the need for an auxiliary electrode.

In some embodiments, a stability module is provided, wherein the sensitivity measurement changes can be quantified such that a co-analyte concentration threshold is determined. A co-analyte threshold is generally defined as a minimum amount of co-analyte required to fully react with the analyte in an enzyme-based analyte sensor in a non-limiting manner. The minimum co-analyte threshold is preferably expressed as a ratio (for example, a glucose-to-oxygen ratio) that defines a concentration of co-analyte required based on a concentration of analyte available to ensure that the enzyme reaction is limited only by the analyte. While not wishing to be bound by theory, it is believed that by determining a stability of the analyte sensor based on a co-analyte threshold, the processor module can be configured to compensate for instabilities in the glucose sensor accordingly, for example by filtering the unstable data, suspending calibration or display, or the like.

In one such embodiment, a data stream from an analyte signal is monitored and a co-analyte threshold set, whereby the co-analyte threshold is determined based on a signal-to-noise ratio exceeding a predetermined threshold. In one embodiment, the signal-to-noise threshold is based on measurements of variability and the sensor signal over a time period, however one skilled in the art appreciates the variety of systems and methods available for measuring signal-to-noise ratios. Accordingly, the stability module can be configured to set determine the stability of the analyte sensor based on the co-analyte threshold, or the like.

In some embodiments, the stability module is configured to prohibit calibration of the sensor responsive to the stability (or instability) of the sensor. In some embodiments, the stability module can be configured to trigger filtering of the glucose signal responsive to a stability (or instability) of the sensor.

In some embodiments, sensitivity changes can be used to trigger a request for one or more new reference glucose values from the host, which can be used to recalibrate the sensor. In some embodiments, the sensor is re-calibrated responsive to a sensitivity change exceeding a preselected threshold value. In some embodiments, the sensor is calibrated repeatedly at a frequency responsive to the measured sensitivity change. Using these techniques, patient inconvenience can be minimized because reference glucose values are generally only requested when timely and appropriate (namely, when a sensitivity or baseline shift is diagnosed).

In some alternative embodiments, sensitivity changes can be used to update calibration. For example, the measured change in transport can be used to update the sensitivity m in the calibration equation. While not wishing to be bound by theory, it is believed that in some embodiments, the sensitivity m of the calibration of the glucose sensor is substantially proportional to the change in solute transport measured by the transport-measuring electrode.

It should be appreciated by one skilled in the art that in some embodiments, the implementation of sensitivity measurements of the preferred embodiments typically necessitate an addition to, or modification of, the existing electronics (for example, potentiostat configuration or settings) of the glucose sensor and/or receiver.

In some embodiments, the signal from the oxygen measuring electrode may be digitally low-pass filtered (for example, with a passband of $0\text{-}10^{-5}$ Hz, dc-24 hour cycle lengths) to remove transient fluctuations in oxygen, due to local ischemia, postural effects, periods of apnea, or the like. Since oxygen delivery to tissues is held in tight homeostatic control, this filtered oxygen signal should oscillate about a relatively constant. In the interstitial fluid, it is thought that the levels are about equivalent with venous blood (40 mmHg). Once implanted, changes in the mean of the oxygen signal (for example, >5%) may be indicative of change in transport through the biointerface (change in sensor sensitivity and/or baseline due to changes in solute transport) and the need for system recalibration.

The oxygen signal may also be used in its unfiltered or a minimally filtered form to detect or predict oxygen deprivation-induced artifact in the glucose signal, and to control display of data to the user, or the method of smoothing, digital filtering, or otherwise replacement of glucose signal artifact. In some embodiments, the oxygen sensor may be implemented in conjunction with any signal artifact detection or prediction that may be performed on the counter electrode or working electrode voltage signals of the electrode system. Co-pending U.S. patent application Ser. No. 10/648,849, which is incorporated by reference in its entirety herein, describes some methods of signal artifact detection and replacement that may be useful such as described herein.

Preferably, the transport-measuring electrode is located within the same local environment as the electrode system associated with the measurement of glucose, such that the transport properties at the transport-measuring electrode are substantially similar to the transport properties at the glucose-measuring electrode.

In a second aspect the preferred embodiments, systems and methods are provided for measuring changes baseline, namely non-glucose related electroactive compounds in the host. Preferably the auxiliary working electrode is configured to measure the baseline of the analyte sensor over time. In some embodiments, the glucose-measuring working electrode 16 is a hydrogen peroxide sensor coupled to a membrane system 22 containing an active enzyme 32 located above the electrode (such as described in more detail with reference to FIGS. 1 to 4, above). In some embodiments, the auxiliary working electrode 18 is another hydrogen peroxide sensor that is configured similar to the glucose-measuring working electrode however a portion 34 of the membrane system 22 above the base-measuring electrode does not have active enzyme therein, such as described in more detail with reference to FIGS. 3A and 3B. The auxiliary working electrode 18 provides a signal substantially comprising the baseline signal, b, which can be (for example, electronically or digitally) subtracted from the glucose signal obtained from the glucose-measuring working electrode to obtain the signal contribution due to glucose only according to the following equation:

$$\text{Signal}_{glucose\ only} = \text{Signal}_{glucose\text{-}measuring\ working\ electrode} - \text{Signal}_{baseline\text{-}measuring\ working\ electrode}$$

In some embodiments, electronic subtraction of the baseline signal from the glucose signal can be performed in the hardware of the sensor, for example using a differential amplifier. In some alternative embodiments, digital subtraction of the baseline signal from the glucose signal can be performed in the software or hardware of the sensor or an associated receiver, for example in the microprocessor.

One aspect the preferred embodiments provides for a simplified calibration technique, wherein the variability of the baseline has been eliminated (namely, subtracted). Namely, calibration of the resultant differential signal ($\text{Signal}_{glucose\ only}$) can be performed with a single matched data pair by solving the following equation:

$$y = mx$$

While not wishing to be bound by theory, it is believed that by calibrating using this simplified technique, the sensor is made less dependent on the range of values of the matched data pairs, which can be sensitive to human error in manual blood glucose measurements, for example. Additionally, by subtracting the baseline at the sensor (rather than solving for the baseline b as in conventional calibration schemes), accuracy of the sensor may increase by altering control of this variable (baseline b) from the user to the sensor. It is additionally believed that variability introduced by sensor calibration may be reduced.

In some embodiments, the glucose-measuring working electrode 16 is a hydrogen peroxide sensor coupled to a membrane system 22 containing an active enzyme 32 located above the electrode, such as described in more detail above; however the baseline signal is not subtracted from the glucose signal for calibration of the sensor. Rather, multiple matched data pairs are obtained in order to calibrate the sensor (for example using y=mx+b) in a conventional manner, and the auxiliary working electrode 18 is used as an indicator of baseline shifts in the sensor signal. Namely, the auxiliary working electrode 18 is monitored for changes above a certain threshold. When a significant change is detected, the system can trigger a request (for example, from the patient or caregiver) for a new reference glucose value (for example, SMBG), which can be used to recalibrate the sensor. By using the auxiliary working electrode signal as an indicator of baseline shifts, recalibration requiring user interaction (namely, new reference glucose values) can be minimized due to timeliness and appropriateness of the requests. In some embodiments, the sensor is re-calibrated responsive to a baseline shifts exceeding a preselected threshold value. In some embodiments, the sensor is calibrated repeatedly at a frequency responsive to the rate-of-change of the baseline.

In yet another alternative embodiment, the electrode system of the preferred embodiments is employed as described above, including determining the differential signal of glucose less baseline current in order to calibrate using the simplified equation (y=mx), and the auxiliary working electrode 18 is further utilized as an indicator of baseline shifts in the sensor signal. While not wishing to be bound by theory, it is believed that shifts in baseline may also correlate and/or be related to changes in the sensitivity m of the glucose signal. Consequently, a shift in baseline may be indicative of a change in sensitivity m. Therefore, the auxiliary working electrode 18 is monitored for changes above a certain threshold. When a significant change is detected, the system can trigger a request (for example, from the patient or caregiver) for a new reference glucose value (for example, SMBG), which can be used to recalibrate the sensor. By using the auxiliary signal as an indicator of possible sensitivity changes, recalibration requiring user interaction (new reference glucose values) can be minimized due to timeliness and appropriateness of the requests.

It is noted that infrequent new matching data pairs may be useful over time to recalibrate the sensor because the sensitivity m of the sensor may change over time (for example, due to maturation of the biointerface that may increase or decrease the glucose and/or oxygen availability to the sensor). However, the baseline shifts that have conventionally required numerous and/or regular blood glucose reference measurements for updating calibration (for example, due to interfering species, metabolism changes, or the like) can be consistently and accurately eliminated using the systems and methods of the preferred embodiments, allowing reduced interaction from the patient (for example, requesting less frequent reference glucose values such as daily or even as infrequently as monthly).

An additional advantage of the sensor of the preferred embodiments includes providing a method of eliminating signal effects of interfering species, which have conventionally been problematic in electrochemical glucose sensors. Namely, electrochemical sensors are subject to electrochemical reaction not only with the hydrogen peroxide (or other analyte to be measured), but additionally may react with other electroactive species that are not intentionally being measured (for example, interfering species), which cause an increase in signal strength due to this interference. In other words, interfering species are compounds with an oxidation potential that overlap with the analyte being measured. Interfering species such as acetaminophen, ascorbate, and urate, are notorious in the art of glucose sensors for producing inaccurate signal strength when they are not properly controlled. Some glucose sensors utilize a membrane system that blocks at least some interfering species, such as ascorbate and urate. Unfortunately, it is difficult to find membranes that are satisfactory or reliable in use, especially in vivo, which effectively block all interferants and/or interfering species. The prior art is crowded with literature dedicated to efforts toward reducing or eliminating interfering species (for example, see U.S. Pat. Nos. 4,776,944, 5,356,786, 5,593,852, 5,776,324B1, and 6,356,776).

The preferred embodiments are particularly advantageous in their inherent ability to eliminate the erroneous transient and non-transient signal effects normally caused by interfering species. For example, if an interferant such as acetaminophen is ingested by a host implanted with a conventional implantable electrochemical glucose sensor (namely, one without means for eliminating acetaminophen), a transient non-glucose related increase in signal output would occur. However, by utilizing the electrode system of the preferred embodiments, both working electrodes respond with substantially equivalent increased current generation due to oxidation of the acetaminophen, which would be eliminated by subtraction of the auxiliary electrode signal from the glucose-measuring electrode signal.

In summary, the system and methods of the preferred embodiments simplify the computation processes of calibration, decreases the susceptibility introduced by user error in calibration, and eliminates the effects of interfering species. Accordingly, the sensor requires less interaction by the patient (for example, less frequent calibration), increases patient convenience (for example, few reference glucose values), and improves accuracy (via simple and reliable calibration).

In another aspect of the preferred embodiments, the analyte sensor is configured to measure any combination of changes in baseline and/or in sensitivity, simultaneously and/or iteratively, using any of the above-described systems and methods. While not wishing to be bound by theory, the preferred embodiments provide for improved calibration of the sensor, increased patient convenience through less frequent patient interaction with the sensor, less dependence on the values/range of the paired measurements, less sensitivity to error normally found in manual reference glucose measurements, adaptation to the maturation of the biointerface over time, elimination of erroneous signal due to interfering species, and/or self-diagnosis of the calibration for more intelligent recalibration of the sensor.

Methods and devices that are suitable for use in conjunction with aspects of the preferred embodiments are disclosed in co-pending U.S. patent application Ser. No. 10/885,476 filed Jul. 6, 2004 and entitled "SYSTEMS AND METHODS FOR MANUFACTURE OF AN ANALYTE SENSOR INCLUDING A MEMBRANE SYSTEM"; U.S. patent application Ser. No. 10/842,716, filed May 10, 2004 and entitled, "MEMBRANE SYSTEMS INCORPORATING BIOACTIVE AGENTS"; co-pending U.S. patent application Ser. No. 10/838,912 filed May 3, 2004 and entitled, "IMPLANTABLE ANALYTE SENSOR"; U.S. patent application Ser. No. 10/789,359 filed Feb. 26, 2004 and entitled, "INTEGRATED DELIVERY DEVICE FOR A CONTINUOUS GLUCOSE SENSOR"; U.S. application Ser. No. 10/685,636 filed Oct. 28, 2003 and entitled, "SILICONE COMPOSITION FOR MEMBRANE SYSTEM"; U.S. application Ser. No. 10/648,849 filed Aug. 22, 2003 and entitled, "SYSTEMS AND METHODS FOR REPLACING SIGNAL ARTIFACTS IN A GLUCOSE SENSOR DATA STREAM"; U.S. application Ser. No. 10/646,333 filed Aug. 22, 2003 entitled, "OPTIMIZED SENSOR GEOMETRY FOR AN IMPLANTABLE GLUCOSE SENSOR"; U.S. application Ser. No. 10/647,065 filed Aug. 22, 2003 entitled, "POROUS MEMBRANES FOR USE WITH IMPLANTABLE DEVICES"; U.S. application Ser. No. 10/633,367 filed Aug. 1, 2003 entitled, "SYSTEM AND METHODS FOR PROCESSING ANALYTE SENSOR DATA"; U.S. Pat. No. 6,702,857 entitled "MEMBRANE FOR USE WITH IMPLANTABLE DEVICES"; U.S. application Ser. No. 09/916,711 filed Jul. 27, 2001 and entitled "SENSOR HEAD FOR USE WITH IMPLANTABLE DEVICE"; U.S. application Ser. No. 09/447,227 filed Nov. 22, 1999 and entitled "DEVICE AND METHOD FOR DETERMINING ANALYTE LEVELS"; U.S. application Ser. No. 10/153,356 filed May 22, 2002 and entitled "TECHNIQUES TO IMPROVE POLYURETHANE MEMBRANES FOR IMPLANTABLE GLUCOSE SENSORS"; U.S. application Ser. No. 09/489,588 filed Jan. 21, 2000 and entitled "DEVICE AND METHOD FOR DETERMINING ANALYTE LEVELS"; U.S. application Ser. No. 09/636,369 filed Aug. 11, 2000 and entitled "SYSTEMS AND METHODS FOR REMOTE MONITORING AND MODULATION OF MEDICAL DEVICES"; and U.S. application Ser. No. 09/916,858 filed Jul. 27, 2001 and entitled "DEVICE AND METHOD FOR DETERMINING ANALYTE LEVELS," as well as issued patents including U.S. Pat. No. 6,001,067 issued Dec. 14, 1999 and entitled "DEVICE AND METHOD FOR DETERMINING ANALYTE LEVELS"; U.S. Pat. No. 4,994,167 issued Feb. 19, 1991 and entitled "BIOLOGICAL FLUID MEASURING DEVICE"; and U.S. Pat. No. 4,757,022 filed Jul. 12, 1988 and entitled "BIOLOGICAL FLUID MEASURING DEVICE"; U.S. Appl. No. 60/489,615 filed Jul. 23, 2003 and entitled "ROLLED ELECTRODE ARRAY AND ITS METHOD FOR MANUFACTURE"; U.S. Appl. No. 60/490,010 filed Jul. 25, 2003 and entitled "INCREASING BIAS FOR OXYGEN PRODUCTION IN AN ELECTRODE ASSEMBLY"; U.S. Appl. No. 60/490,009 filed Jul. 25, 2003 and entitled "OXYGEN ENHANCING ENZYME MEMBRANE FOR ELECTROCHEMICAL SENSORS"; U.S. application Ser. No. 10/896,312 filed Jul. 21, 2004 and entitled "OXYGEN-GENERATING ELECTRODE FOR USE IN ELECTROCHEMICAL SENSORS"; U.S. application Ser. No. 10/896,637 filed Jul. 21, 2004 and entitled "ROLLED ELECTRODE ARRAY AND ITS METHOD FOR MANUFACTURE"; U.S. application Ser. No. 10/896,772 filed Jul. 21, 2004 and entitled "INCREASING BIAS FOR OXYGEN PRODUCTION IN AN ELECTRODE ASSEMBLY"; U.S. application Ser. No. 10/896,639 filed Jul. 21, 2004 and entitled "OXYGEN ENHANCING ENZYME MEMBRANE FOR ELECTROCHEMICAL SENSORS"; U.S. application Ser. No. 10/897,377 filed Jul. 21, 2004 and entitled "ELECTROCHEMICAL SENSORS INCLUDING ELECTRODE SYSTEMS WITH INCREASED OXYGEN GENERATION". The foregoing patent applications and patents are incorporated herein by reference in their entireties.

All references cited herein are incorporated herein by reference in their entireties. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A method for continuous glucose sensing, the method comprising:
   generating a glucose signal associated with a glucose concentration in a host using a continuous glucose sensor;
   detecting oxygen deprivation; and
   determining, using a processor module, a stability of the continuous glucose sensor based on the oxygen deprivation detection.

2. The method of claim 1, wherein detecting oxygen deprivation comprises examining a signal for oxygen deprivation-induced artifacts.

3. The method of claim 1, wherein the continuous glucose sensor comprises an electrode, and wherein detecting oxygen deprivation comprises switching, cycling or pulsing a voltage applied to the electrode and evaluating, using a processor module, a response to the applied voltage.

4. The method of claim 1, wherein determining a stability further comprises determining a sensitivity change over a time period.

5. The method of claim 4, wherein the sensitivity change is not based on a reference glucose measurement from a reference glucose monitor.

6. The method of claim 1, wherein the glucose signal is generated in vivo.

7. The method of claim 1, further comprising controlling a display of the glucose signal responsive to the stability determination.

8. The method of claim 1, further comprising suspending a display of the glucose signal responsive to the stability determination.

9. A system for continuous glucose sensing, the system comprising:
   a continuous glucose sensor configured to generate a glucose signal associated with a glucose concentration in a host; and
   electronic circuitry configured to determine a stability of the continuous glucose sensor by detecting oxygen deprivation.

10. The system of claim 9, wherein the electronic circuitry is configured to detect oxygen deprivation by examining a signal for oxygen deprivation-induced artifacts.

11. The system of claim 9, wherein the continuous glucose sensor comprises an electrode, and wherein the electronic circuitry is configured to detect oxygen deprivation by switching, cycling or pulsing a voltage applied to the electrode and to evaluate a response to the applied voltage.

12. The system of claim 9, wherein the electronic circuitry is further configured to determine a sensitivity change over a time period.

13. The system of claim 12, wherein the electronic circuitry is configured to determine the sensitivity change without a reference glucose measurement from a reference glucose monitor.

14. The system of claim 9, wherein the electronic circuitry is configured to control a display of the glucose signal responsive to the stability determination.

15. The system of claim 9, wherein the electronic circuitry is configured to suspend a display of the glucose signal responsive to the stability determination.

16. A system for continuous glucose sensing, the system comprising:

means for generating a glucose signal associated with a glucose concentration in a host using a continuous glucose sensor;

means for detecting oxygen deprivation; and means for determining a stability of the continuous glucose sensor based on the oxygen deprivation detection.

* * * * *

UNITED STATES PATENT AND TRADEMARK OFFICE
CERTIFICATE OF CORRECTION

PATENT NO. : 8,160,671 B2
APPLICATION NO. : 12/874031
DATED : April 17, 2012
INVENTOR(S) : Kamath et al.

It is certified that error appears in the above-identified patent and that said Letters Patent is hereby corrected as shown below:

| Issued Patent | | Description of Discrepancy |
|---|---|---|
| Column | Line | |
| On the Title Page: (Item 56) Col. 2 | 18 | Under Other Publications, change "Immoblized" to --Immobilized--. |
| (Item 56) Page 8 Col. 1 | 14 | Under Other Publications, change "Membr" to --Membrane--. |
| (Item 56) Page 8 Col. 1 | 16 | Under Other Publications, change "Decarbozylase" to --Decarboxylase--. |
| (Item 56) Page 8 Col. 1 | 23 | Under Other Publications, change "Sens" to --Sensors--. |
| (Item 56) Page 8 Col. 1 | 41 | Under Other Publications, change "hypoglycaemic" to --hypoglycemic--. |
| (Item 56) Page 8 Col. 1 | 52 | Under Other Publications, change "Senso" to --Sensor--. |
| (Item 56) Page 8 Col. 1 | 63 | Under Other Publications, change "basedon" to --based--. |
| (Item 56) Page 8 Col. 2 | 20 | Under Other Publications, change "dynamcs" to --dynamics--. |
| (Item 56) Page 8 Col. 2 | 36 | Under Other Publications, change "inactiviation" to --inactivation--. |

Signed and Sealed this
Eleventh Day of September, 2012

David J. Kappos
*Director of the United States Patent and Trademark Office*

CERTIFICATE OF CORRECTION (continued)
U.S. Pat. No. 8,160,671 B2

| | | |
|---|---|---|
| (Item 56) Page 8 Col. 2 | 39 | Under Other Publications, change "patents" to --patients--. |
| (Item 56) Page 9 Col. 1 | 15 | Under Other Publications, change "amperometeric" to --amperometric--. |
| (Item 56) Page 9 Col. 2 | 10 | Under Other Publications, change "Membran," to --Membrane,--. |
| (Item 56) Page 11 Col. 1 | 17 | Under Other Publications, change "Thechnol." to --Technol.--. |
| (Item 56) Page 11 Col. 2 | 14 | Under Other Publications, change "reliablity" to --reliability--. |
| (Item 56) Page 11 Col. 2 | 20 | Under Other Publications, change "Clarke et al." to --Clark et al.--. |
| (Item 56) Page 11 Col. 2 | 28 | Under Other Publications, change "Enzymlology," to --Enzymology,--. |
| (Item 56) Page 11 Col. 2 | 36 | Under Other Publications, change "systme" to --system--. |
| (Item 56) Page 11 Col. 2 | 65 | Under Other Publications, change "your and your" to --you and your--. |
| (Item 56) Page 11 Col. 2 | 73 | Under Other Publications, change "Diabetese" to --Diabetes--. |
| (Item 56) Page 12 Col. 1 | 9 | Under Other Publications, change "Rese." to --Res.--. |
| (Item 56) Page 12 Col. 1 | 20 | Under Other Publications, change "Thechnol." to --Technol.--. |
| (Item 56) Page 12 Col. 1 | 25 | Under Other Publications, change "Diabetese" to --Diabetes--. |
| (Item 56) Page 12 Col. 2 | 29 | Under Other Publications, change "Aniodic" to --Anodic--. |
| (Item 56) Page 13 Col. 1 | 12 | Under Other Publications, change "activitiy," to --activity,--. |

| | | |
|---|---|---|
| (Item 56) Page 13 Col. 1 | 33 | Under Other Publications, change "Beioelectronics," to --Bioelectronics,--. |
| (Item 56) Page 13 Col. 1 | 34 | Under Other Publications, change "glocuse" to --glucose--. |
| (Item 56) Page 13 Col. 1 | 51 | Under Other Publications, change "valication" to --validation--. |
| (Item 56) Page 13 Col. 1 | 52 | Under Other Publications, change "iunsulin interaaction in tyhpe 1" to --insulin interaction in type 1--. |
| (Item 56) Page 13 Col. 1 | 67 | Under Other Publications, change "Electronanalysis" to --Electroanalysis--. |
| (Item 56) Page 13 Col. 2 | 14 | Under Other Publications, change "artifical" to --artificial--. |
| (Item 56) Page 13 Col. 2 | 33 | Under Other Publications, change "Thechnol." to --Technol.--. |
| (Item 56) Page 14 Col. 1 | 3 | Under Other Publications, change "Apllied" to --Applied--. |
| (Item 56) Page 14 Col. 1 | 67 | Under Other Publications, change "Subcutaenous" to --Subcutaneous--. |
| (Item 56) Page 14 Col. 2 | 5 | Under Other Publications, change "assitance" to --assistance--. |
| (Item 56) Page 14 Col. 2 | 6 | Under Other Publications, change "Thechnol." to --Technol.--. |
| (Item 56) Page 14 Col. 2 | 15 | Under Other Publications, change "Membran," to --Membrane,--. |
| (Item 56) Page 14 Col. 2 | 38 | Under Other Publications, change "Aced" to --Acad--. |
| (Item 56) Page 14 Col. 2 | 53 | Under Other Publications, change "pancrease" to --pancreas--. |
| (Item 56) Page 14 Col. 2 | 63 | Under Other Publications, change "Thechnol." to --Technol.--. |

CERTIFICATE OF CORRECTION (continued)
U.S. Pat. No. 8,160,671 B2

| | | |
|---|---|---|
| (Item 56) Page 15 Col. 1 | 28 | Under Other Publications, change "cholesteral" to --cholesterol--. |
| (Item 56) Page 15 Col. 1 | 52 | Under Other Publications, change "Deabetes" to --Diabetes--. |

IN THE SPECIFICATIONS:

| | | |
|---|---|---|
| 6 | 19 | Change "thereon" to --thereon.--. |
| 7 | 6 | Change "andrenostenedione;" to --androstenedione;--. |
| 7 | 21 | Change "diptheria/" to --diphtheria/--. |
| 7 | 28 | Change "perioxidase;" to --peroxidase;--. |
| 7 | 37 | Change "sissomicin;" to --sisomicin;--. |
| 7 | 41 | Change "duodenalisa," to --duodenalis,--. |
| 7 | 49 | Change "Trepenoma pallidium," to --Treponema pallidum,--. |
| 7 | 50 | Change "stomatis" to --stomatitis--. |
| 8 | 3 | Change "(barbituates," to --(barbiturates,--. |
| 14 | 42 | Change "entirety" to --entirety.--. |
| 17 | 5 | Change "by product," to --byproduct,--. |
| 18 | 32 | Change "FIG." to --FIGS.--. |
| 19 | 16 | Change "ureate," to --urate,--. |
| 20 | 47 | Change "20,22" to --20, 22--. |
| 21 | 22 | Change "inseted" to --inserted--. |
| 29 | 67 | Change "interferant" to --interferent--. |